United States Patent
During et al.

(10) Patent No.: US 9,265,843 B2
(45) Date of Patent: Feb. 23, 2016

(54) TREATMENT OF METABOLIC-RELATED DISORDERS USING HYPOTHALAMIC GENE TRANSFER OF BDNF AND COMPOSITIONS THEREFOR

(75) Inventors: Matthew J. During, Columbus, OH (US); Lei Cao, Columbus, OH (US)

(73) Assignee: The Ohio State University, Columbus, OH (US)

( * ) Notice: Subject to any disclaimer, the term of this patent is extended or adjusted under 35 U.S.C. 154(b) by 742 days.

(21) Appl. No.: 12/934,735

(22) PCT Filed: Mar. 27, 2009

(86) PCT No.: PCT/US2009/038593
§ 371 (c)(1),
(2), (4) Date: Feb. 21, 2011

(87) PCT Pub. No.: WO2009/120978
PCT Pub. Date: Oct. 1, 2009

(65) Prior Publication Data
US 2011/0288160 A1 Nov. 24, 2011

Related U.S. Application Data

(60) Provisional application No. 61/072,146, filed on Mar. 27, 2008.

(51) Int. Cl.
| | | |
|---|---|---|
| A61K 48/00 | (2006.01) | |
| A61P 3/00 | (2006.01) | |
| A61P 3/04 | (2006.01) | |
| A61P 3/08 | (2006.01) | |
| A61P 3/10 | (2006.01) | |
| C12N 15/63 | (2006.01) | |
| C12N 15/85 | (2006.01) | |
| C12N 15/86 | (2006.01) | |
| C12N 15/861 | (2006.01) | |
| C12N 15/113 | (2010.01) | |

(52) U.S. Cl.
CPC ........... *A61K 48/005* (2013.01); *A61K 48/0075* (2013.01); *C12N 15/1136* (2013.01); *C12N 15/86* (2013.01); *C12N 2310/14* (2013.01); *C12N 2330/51* (2013.01); *C12N 2750/14143* (2013.01); *C12N 2830/48* (2013.01); *C12N 2830/50* (2013.01)

(58) Field of Classification Search
None
See application file for complete search history.

(56) References Cited

U.S. PATENT DOCUMENTS

| 6,096,716 A | 8/2000 | Hayes et al. |
|---|---|---|
| 2002/0058325 A1* | 5/2002 | Hardy .................... 435/235.1 |
| 2004/0110711 A1 | 6/2004 | Krueger et al. |
| 2004/0224409 A1 | 11/2004 | Pradier et al. |
| 2005/0234000 A1 | 10/2005 | Mitchell et al. |
| 2006/0030538 A1 | 2/2006 | Hendriks |
| 2006/0292117 A1 | 12/2006 | Loiler et al. |
| 2007/0244520 A1 | 10/2007 | Ferren et al. |

FOREIGN PATENT DOCUMENTS

WO WO2007088201 A1 8/2007

OTHER PUBLICATIONS

Li, et al. (Feb. 2008) "Construction and expression of recombinant adeno-associated virus expressing brain-derived neurotrophic factor", Sheng Wu Gong Cheng Xue Bao, 24(2): 328-32 (Abstract Only).*
Cao, et al. (2009) "Molecular therapy of obesity and diabetes by a physiological autoregulatory approach", Nature Medicine, 15(4): 447-54.*
Kells, et al. (2006) "Protection Against Huntington's Disease Progression: AAV-Mediated Delivery of Biotherapeutics", Molecular Therapy, 13(suppl 1):S95-S96.*
Paterna, et al. (2000) "Influence of promoter and WHV post-transcriptional regulatory element on AAV-mediated transgene expression in the rat brain", Gene Therapy, 7(15): 1304-11.*
PCT International Search Report and the Written Opinion, PCT/US2009/038593 filed Mar. 27, 2009, dated Dec. 4, 2009.
PCT/US2009/038593 International Preliminary Report on Patentability, PCT/US2009/038593 filed Mar. 27, 2009, dated Oct. 7, 2010.
Brown, A.M. et al., "The Gene Structure and Minimal Promoter of the Human Agouti Related Protein," Gene, 2001, vol. 277, pp. 231-238.
Hammer, G.D. et al., "Transsphenoidal Microsurgery for Cushing's Disease: Initial Outcome and Long-Term Results," The Journal of Clinical Endocrinology & Metabolism, 2004, vol. 89, No. 12, pp. 6348-6357.
Tsao, D. et al., "TrkB Agonists Amerliorate Obesity and Associated Metabolic Conditions in Mice," Endocrinology, 2008, vol. 149, No. 3, pp. 1038-1048.

* cited by examiner

*Primary Examiner* — Robert M Kelly
(74) *Attorney, Agent, or Firm* — MacMillan, Sobanski & Todd, LLC

(57) ABSTRACT

Described herein is a system which uses a gene therapy particle that includes at least one gene, cDNA, fragment or analogue of at least one neurotropin that binds to the trkB receptor or the trkB receptor itself. The gene therapy particle is capable of being delivered to a subject in need thereof for therapy of a metabolic disorder. In a particular aspect, this invention is directed to an inventive method that demonstrates a remarkable efficacy on lowering body weight.

17 Claims, 44 Drawing Sheets
(21 of 44 Drawing Sheet(s) Filed in Color)

| Parameter | Standard diet# | | High fat diet§ | |
|---|---|---|---|---|
| | GFP | BDNF | YFP | BDNF |
| | (n = 10) | (n = 14) | (n = 8) | (n = 8) |
| IGF-1 (ng ml$^{-1}$) | 58.47 ± 3.38 | 15.05 ± 0.69* | 62.02 ± 7.10 | 20.25 ± 3.51* |
| Leptin (ng ml$^{-1}$) | 0.613 ± 0.089 | 0.075 ± 0.002* | 16.46 ± 2.27 | 0.989 ± 0.151* |
| Adiponectin (µg ml$^{-1}$) | 3.22 ± 0.13 | 5.15 ± 0.35* | 3.07 ± 0.1 | 5.13 ± 0.15* |
| Leptin R (ng ml$^{-1}$) | 1.84 ± 0.08 | 3.59 ± 0.30* | 3.10 ± 0.37 | 7.02 ± 0.83* |
| Insulin (ng ml$^{-1}$) | 1.27 ± 0.43 | 0.23 ± 0.03* | 5.11 ± 1.14 | 0.74 ± 0.11* |
| Glucose (mg dl$^{-1}$) | 225.88 ± 13.24 | 189.18 ± 12.76⁺ | 408.81 ± 30.86 | 212.03 ± 10.87* |
| Cholesterol (mg dl$^{-1}$) | 77.71 ± 2.14 | 65.29 ± 3.96* | 174.09 ± 16.02 | 75.37 ± 3.36* |
| Triglyceride (mg dl$^{-1}$) | 70.05 ± 7.42 | 33.30 ± 3.39* | 63.45 ± 8.00 | 49.25 ± 7.85 |

3 weeks after AAV injection; § 10 weeks after AAV injection

* $P < 0.05$ BDNF mice vs controls on respective diet; + $P = 0.062$

Figure 12 pAM/CBA-NPY-WPRE-BGH Nucleotide Sequence

```
   1 tagctgcgcg ctcgctcgct cactgaggcc gcccgggcaa agcccgggcg tcgggcgacc
  61 tttggtcgcc cggcctcagt gagcgagcga gcgcgcagag agggagtggc caactccatc
 121 actaggggtt ccttgtagtt aatgattaac ccgccatgct acttatctac gtagccatgc
 181 tctaggtacc attgacgtca ataatgacgt atgttcccat agtaacgcca tagggacttt
 241 tccattgacg tcaatgggtg gactatttac ggtaaactgc ccacttggca gtacatcaag
 301 tgtatcatat gccaagtacg cccctattg acgtcaatga cggtaaatgg cccgcctggc
 361 attatgccca gtacatgacc ttatgggact ttcctacttg gcagtacatc tacgtattag
 421 tcatcgctat taccatggtc gaggtgagcc ccacgttctg cttcactctc cccatctccc
 481 cccctcccc accccaatt ttgtatttat ttatttttta attattttgt gcagcgatgg
 541 gggcgggggg ggggggggg cgcgcgccag gcggggcggg gcggggcgag gggcggggcg
 601 gggcgaggcg gagaggtgcg gcggcagcca atcagagcgg cgcgctccga aagtttcctt
 661 ttatggcgag gcggcggcgg cggcggccct ataaaaagcg aagcgcgcgg cgggcgggag
 721 tcgctgcgac gctgccttcg ccccgtgccc cgctccgccg ccgcctcgcg ccgcccgccc
 781 cggctctgac tgaccgcgtt actcccacag gtgagcgggc gggacggccc ttctcctccg
 841 ggctgtaatt agcgcttggt ttaatgacgg cttgtttctt ttctgtggct gcgtgaaagc
 901 cttgaggggc tccgggaggg ccctttgtgc ggggggagcg gctcggggct gtccgcgggg
 961 ggacggctgc cttcgggggg gacggggcag ggcggggttc ggcttctggc gtgtgaccgg
1021 cggctctaga gcctctgcta accatgttca tgccttcttc ttttcctac agctcctggg
1081 caacgtgctg gttattgtgc tgtctcatca ttttggcaaa gaattggatc cgccatgcta
1141 ggtaacaagc gactggggct gtccggactg accctcgccc tgtccctgct cgtgtgcctg
1201 ggtgcgctgg ccgaggcgta cccctccaag ccggacaacc cgggcgagga cgcaccagcg
1261 gaggacatgg ccagatacta ctcagcgctg cgacactaca tcaacctcat caccaggcag
1321 agatatggaa acgatctag cccagagaca ctgatttcag acctcttgat gagagaaagc
1381 acagaaaatg ttcccagaac tcggcttgaa gaccctgcaa tgtggtgaga attcgatatc
1441 aagcttatcg ataatcaacc tctggattac aaaatttgtg aaagattgac tggtattctt
1501 aactatgttg ctccttttac gctatgtgga tacgctgctt taatgccttt gtatcatgct
```

Figure 13b

1561 attgcttccc gtatggcttt cattttctcc tccttgtata aatcctggtt gctgtctctt 1621 tatgaggagt tgtggcccgt tgtcaggcaa cgtggcgtgg tgtgcactgt gtttgctgac 1681 gcaaccccca ctggttgggg cattgccacc acctgtcagc tcctttccgg gactttcgct 1741 ttccccctcc ctattgccac ggcggaactc atcgccgcct gccttgcccg ctgctggaca 1801 ggggctcggc tgttgggcac tgacaattcc gtggtgttgt cggggaaatc atcgtccttt 1861 ccttggctgc tcgcctgtgt tgccacctgg attctgcgcg gacgtccttt ctgctacgtc 1921 ccttcggccc tcaatccagc ggaccttcct tcccgcggcc tgctgccggc tctgcggcct 1981 cttccgcgtc ttcgccttcg ccctcagacg agtcggatct cctttgggc cgcctccccg 2041 catcgatacc gtcgactcgc tgatcagcct cgactgtgcc ttctagttgc cagccatctg 2101 ttgtttgccc ctcccccgtg ccttccttga ccctggaagg tgccactccc actgtccttt 2161 cctaataaaa tgaggaaatt gcatcgcatt gtctgagtag gtgtcattct attctggggg 2221 gtggggtggg gcaggacagc aaggggggagg attgggaaga caatagcagg catgctgggg 2281 atgcggtggg ctctatggct tctgaggcgg aaagaaccag ctggggctcg actagagcat 2341 ggctacgtag ataagtagca tggcgggtta atcattaact acaaggaacc cctagtgatg 2401 gagttggcca ctccctctct gcgcgctcgc tcgctcactg aggccgggcg accaaaggtc 2461 gcccgacgcc cgggctttgc ccgggcggcc tcagtgagcg agcgagcgcg cagagctttt 2521 tgcaaaagcc taggcctcca aaaaagcctc ctcactactt ctggaatagc tcagaggccg 2581 aggcggcctc ggcctctgca taaataaaaa aaattagtca gccatggggc ggagaatggg 2641 cggaactggg cggagttagg ggcgggatgg gcggagttag gggcgggact atggttgctg 2701 actaattgag atgcatgctt tgcatacttc tgcctgctgg ggagcctggg gactttccac 2761 acctggttgc tgactaattg agatgcatgc tttgcatact tctgcctgct ggggagcctg 2821 gggactttcc acaccctaac tgacacacat tccacagctg cattaatgaa tcggccaacg 2881 cgcggggaga ggcggtttgc gtattgggcg ctcttccgct tcctcgctca ctgactcgct 2941 gcgctcggtc gttcggctgc ggcgagcggt atcagctcac tcaaaggcgg taatacggtt 3001 atccacagaa tcaggggata acgcaggaaa gaacatgtga gcaaaaggcc agcaaaaggc 3061 caggaaccgt aaaaaggccg cgttgctggc gttttccat aggctccgcc cccctgacga

Figure 13b cont.

3121 gcatcacaaa aatcgacgct caagtcagag gtggcgaaac ccgacaggac tataaagata 3181 ccaggcgttt ccccctggaa gctccctcgt gcgctctcct gttccgaccc tgccgcttac 3241 cggatacctg tccgcctttc tcccttcggg aagcgtggcg ctttctcata gctcacgctg 3301 taggtatctc agttcggtgt aggtcgttcg ctccaagctg ggctgtgtgc acgaaccccc 3361 cgttcagccc gaccgctgcg ccttatccgg taactatcgt cttgagtcca acccggtaag 3421 acacgactta tcgccactgg cagcagccac tggtaacagg attagcagag cgaggtatgt 3481 aggcggtgct acagagttct tgaagtggtg gcctaactac ggctacacta agaacagt 3541 atttggtatc tgcgctctgc tgaagccagt taccttcgga aaaagagttg gtagctcttg 3601 atccggcaaa caaaccaccg ctggtagcgg tggtttttt gtttgcaagc agcagattac 3661 gcgcagaaaa aaaggatctc aagaagatcc tttgatcttt tctacggggt ctgacgctca 3721 gtggaacgaa aactcacgtt aagggatttt ggtcatgaga ttatcaaaaa ggatcttcac 3781 ctagatcctt ttaaattaaa aatgaagttt taaatcaatc taaagtatat atgagtaaac 3841 ttggtctgac agttaccaat gcttaatcag tgaggcacct atctcagcga tctgtctatt 3901 tcgttcatcc atagttgcct gactccccgt cgtgtagata actacgatac gggagggctt 3961 accatctggc cccagtgctg caatgatacc gcgagaccca cgctcaccgg ctccagattt 4021 atcagcaata aaccagccag ccggaagggc cgagcgcaga agtggtcctg caactttatc 4081 cgcctccatc cagtctatta attgttgccg ggaagctaga gtaagtagtt cgccagttaa 4141 tagtttgcgc aacgttgttg ccattgctac aggcatcgtg gtgtcacgct cgtcgtttgg 4201 tatggcttca ttcagctccg gttcccaacg atcaaggcga gttacatgat cccccatgtt 4261 gtgcaaaaaa gcggttagct ccttcggtcc tccgatcgtt gtcagaagta agttggccgc 4321 agtgttatca ctcatggtta tggcagcact gcataattct cttactgtca tgccatccgt 4381 aagatgcttt tctgtgactg gtgagtactc aaccaagtca ttctgagaat agtgtatgcg 4441 gcgaccgagt tgctcttgcc cggcgtcaat acgggataat accgcgccac atagcagaac 4501 tttaaaagtg ctcatcattg gaaaacgttc ttcggggcga aaactctcaa ggatcttacc 4561 gctgttgaga tccagttcga tgtaacccac tcgtgcaccc aactgatctt cagcatcttt 4621 tactttcacc agcgtttctg ggtgagcaaa aacaggaagg caaaatgccg caaaaaaggg

Figure 13b cont.

4681 aataagggcg acacggaaat gttgaatact catactcttc cttttcaat attattgaag 4741 catttatcag ggttattgtc tcatgagcgg atacatattt gaatgtattt agaaaaataa 4801 acaaataggg gttccgcgca catttccccg aaaagtgcca cctgacgtct aagaaaccat 4861 tattatcatg acattaacct ataaaaatag gcgtatcacg aggcccttc gtctcgcgcg 4921 tttcggtgat gacggtgaaa acctctgaca catgcagctc ccggagacgg tcacagcttg 4981 tctgtaagcg gatgccggga gcagacaagc ccgtcagggc gcgtcagcgg gtgttggcgg 5041 gtgtcggggc tggcttaact atgcggcatc agagcagatt gtactgagag tgcaccattc 5101 gacgctctcc cttatgcgac tcctgcatta ggaagcagcc cagtagtagg ttgaggccgt 5161 tgagcaccgc cgccgcaagg aatggtgcat gcaaggagat ggcgcccaac agtcccccgg 5221 ccacggggcc tgccaccata cccacgccga aacaagcgct catgagcccg aagtggcgag 5281 cccgatcttc cccatcggtg atgtcggcga tataggcgcc agcaaccgca cctgtggcgc 5341 cggtgatgcc ggccacgatg cgtccggcgt agaggatctg gctagcgatg accctgctga 5401 ttggttcgct gaccatttcc gggtgcggga cggcgttacc agaaactcag aaggttcgtc 5461 caaccaaacc gactctgacg gcagtttacg agagagatga tagggtctgc ttcagtaagc 5521 cagatgctac acaattaggc ttgtacatat tgtcgttaga acgcggctac aattaataca 5581 taaccttatg tatcatacac atacgattta ggtgacacta tagaatacac ggaattaatt 5641 c

Figure 13b cont.

CAG-BDNF-HA-WPRE

```
cattgacgtcaataatgacgtatgttcccatagtaacgccaatagggactttccattgacgtcaatgggtggactatttac
ggtaaactgcccacttggcagtacatcaagtgtatcatatgccaagtacgccccctattgacgtcaatgacggtaaatg
gcccgcctggcattatgcccagtacatgaccttatgggactttcctacttggcagtacatctacgtattagtcatcgctatt
accatggtcgaggtgagccccacgttctgcttcactctccccatctcccccccctccccacccccaatttgtatttattta
tttttaattattttgtgcagcgatggggcggggggggggggggggcgcgcgccaggcggggcggggcggggcg
aggggcggggcggggcgaggcggagaggtgcggcggcagccaatcagagcggcgcgctccgaaagtttccttt
atggcgaggcggcggcggcggcccctataaaaagcgaagcgcgcggcgggcgggagtcgctgcgacgctg
cctttcgccccgtgccccgctccgccgcgcctcgcgccgcccgccccggctctgactgaccgcgttactcccacag
gtgagcgggcgggacggcccttctcctccgggctgtaattagcgcttggtttaatgacggcttgtttctttctgtggctg
cgtgaaagccttgaggggctccggggaggccctttgtgcgggggagcggctcggggctgtccgcgggggggacg
gctgccttcgggggggacggggcagggcggggttcggcttctggcgtgtgaccggcggctctagagcctctgctaa
ccatgttcatgccttcttctttttcctacagctcctgggcaacgtgctggttattgtgctgtctcatcattttggcaaagaattg
gatccactcgagtggagctcgcgactagtcgattcgaattcggcttgtgatgaccatcctttccttactatggttatttcat
acttggttgcatgaaggctgccccccatgaaagaagcaaacatccgaggacaaggtggcttggcctacccaggtgtg
cggacccatgggactctggagagcgtgaatgggcccaaggcaggttcaagaggcttgacatcattggctgacacttt
cgaacacgtgatagaagagctgttggatgaggaccagaaagttcggcccaatgaagaaaacaataaggacgcaga
cttgtacacgtccagggtgatgctcagtagtcaagtgcctttggagcctcctcttctcttctgctggaggaatacaaaaa
ttacctagatgctgcaaacatgtccatgagggtccggcgccactctgaccctgcccgccgaggggagctgagcgtgt
gtgacagtattagtgagtgggtaacggcggcagacaaaaagactgcagtggacatgtcgggcgggacggtcacagt
ccttgaaaaggtccctgtatcaaaaggccaactgaagcaatacttctacgagaccaagtgcaatcccatgggttacac
aaaagaaggctgcaggggcatagacaaaaggcattggaactcccagtgccgaactacccagtcgtacgtgcgggc
ccttaccatggatagcaaaaagagaattggctggcgattcataaggatagacacttcttgtgtatgtacattgaccattaa
aaggggaagatatccgtatgatgttcctgattattgagaattcgatatcaagcttatcgataatcaacctctggattacaaa
atttgtgaaagattgactggtattcttaactatgttgctcctttttacgctatgtggatacgctgctttaatgcctttgtatcatgc
tattgcttcccgtatggctttcattttctcctccttgtataaatcctggttgctgtctctttatgaggagttgtggcccgttgtca
ggcaacgtggcgtggtgtgcactgtgtttgctgacgcaacccccactggttggggcattgccaccacctgtcagctcct
tccgggactttcgctttccccctccctattgccacggcggaactcatcgccgcctgccttgcccgctgctggacaggg
gctcggctgttgggcactgacaattccgtggtgttgtcggggaaatcatcgtcctttccttggctgctcgcctgtgttgcc
acctggattctgcgcgggacgtccttctgctacgtcccttcggccctcaatccagcggaccttccttcccgcggcctgc
tgccggctctgcggcctcttccgcgtcttcgccttcgccctcagacgagtcggatctccctttgggccgcctcccc
```

Figure 13C

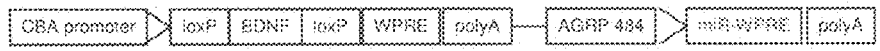

Figure 14

```
                NM_170735 human BDNF seq references deleted.txt
LOCUS       NM_170735               4755 bp    mRNA    linear   PRI 15-FEB-2009
DEFINITION  Homo sapiens brain-derived neurotrophic factor (BDNF), transcript
            variant 1, mRNA.
ACCESSION   NM_170735
VERSION     NM_170735.5  GI:219842286
KEYWORDS    .
SOURCE      Homo sapiens (human)
  ORGANISM  Homo sapiens
            Eukaryota; Metazoa; Chordata; Craniata; Vertebrata; Euteleostomi;
            Mammalia; Eutheria; Euarchontoglires; Primates; Haplorrhini;
            Catarrhini; Hominidae; Homo.
COMMENT     REVIEWED REFSEQ: This record has been curated by NCBI staff. The
            reference sequence was derived from EF689009.1.
            On Jan 9, 2009 this sequence version replaced gi:60218885.

Summary: The protein encoded by this gene is a member of the nerve
            growth factor family. It is induced by cortical neurons, and is
            necessary for survival of striatal neurons in the brain. Expression
            of this gene is reduced in both Alzheimer's and Huntington disease
            patients. This gene may play a role in the regulation of stress
            response and in the biology of mood disorders. Multiple transcript
            variants encoding distinct isoforms have been described for this
            gene. [provided by RefSeq].

Transcript Variant: This variant (1), also known as IX, represents
            the longest transcript. Variants 1, 2, 4, 5, and 7-16 encode the
            same isoform (a).

Publication Note:  This RefSeq record includes a subset of the
            publications that are available for this gene. Please see the
            Entrez Gene record to access additional publications.
            COMPLETENESS: complete on the 3' end.
PRIMARY     REFSEQ_SPAN         PRIMARY_IDENTIFIER PRIMARY_SPAN        COMP
            1-4755              EF689009.1         15-4769
FEATURES             Location/Qualifiers
     source          1..4755
                     /organism="Homo sapiens"
                     /mol_type="mRNA"
                     /db_xref="taxon:9606"
                     /chromosome="11"
                     /map="11p13"
     gene            1..4755
                     /gene="BDNF"
                     /gene_synonym="MGC34632"
                     /note="brain-derived neurotrophic factor"
                     /db_xref="GeneID:627"
                     /db_xref="HGNC:1033"
                     /db_xref="HPRD:00214"
                     /db_xref="MIM:113505"
     exon            1..2178
                     /gene="BDNF"
                     /gene_synonym="MGC34632"
                     /inference="alignment:Splign"
                     /number=11b
     STS             597..1175
                     /gene="BDNF"
                     /gene_synonym="MGC34632"
                     /standard_name="GDB:197571"
                     /db_xref="UniSTS:155950"
     CDS             1086..1829
                     /gene="BDNF"
                     /gene_synonym="MGC34632"
                                Page 1
```

Figure 15

```
                NM_170735 human BDNF seq references deleted.txt
                    /note="isoform a preproprotein is encoded by transcript
                    variant 1; neurotrophin"
                    /codon_start=1
                    /product="brain-derived neurotrophic factor isoform a
                    preproprotein"
                    /protein_id="NP_733931.1"
                    /db_xref="GI:25306264"
                    /db_xref="CCDS:CCDS7866.1"
                    /db_xref="GeneID:627"
                    /db_xref="HGNC:1033"
                    /db_xref="HPRD:00214"
                    /db_xref="MIM:113505"
                    /translation="MTILFLTMVISYFGCMKAAPMKEANIRGQGGLAYPGVRTHGTLE
                    SVNGPKAGSRGLTSLADTFEHVIEELLDEDQKVRPNEENNKDADLYTSRVMLSSQVPL
                    EPPLLFLLEEYKNYLDAANMSMRVRRHSDPARRGELSVCDSISEWVTAADKKTAVDMS
                    GGTVTVLEKVPVSKGQLKQYFYETKCNPMGYTKEGCRGIDKRHWNSQCRTTQSYVRAL
                    TMDSKKRIGWRFIRIDTSCVCTLTIKRGR"
sig_peptide     1086..1139
                    /gene="BDNF"
                    /gene_synonym="MGC34632"
proprotein      1140..1826
                    /gene="BDNF"
                    /gene_synonym="MGC34632"
                    /product="brain-derived neurotrophic factor isoform a
                    proprotein"
mat_peptide     1470..1826
                    /gene="BDNF"
                    /gene_synonym="MGC34632"
                    /product="brain-derived neurotrophic factor isoform a"
STS             1091..1699
                    /gene="BDNF"
                    /gene_synonym="MGC34632"
                    /standard_name="BDNF"
                    /db_xref="UniSTS:266531"
STS             1442..1724
                    /gene="BDNF"
                    /gene_synonym="MGC34632"
                    /standard_name="BDNF-1"
                    /db_xref="UniSTS:253960"
STS             1506..2388
                    /gene="BDNF"
                    /gene_synonym="MGC34632"
                    /standard_name="BDNF_2411"
                    /db_xref="UniSTS:280459"
STS             1990..2091
                    /gene="BDNF"
                    /gene_synonym="MGC34632"
                    /standard_name="D11S4429"
                    /db_xref="UniSTS:43225"
polyA_signal    2118..2123
                    /gene="BDNF"
                    /gene_synonym="MGC34632"
polyA_site      2145
                    /gene="BDNF"
                    /gene_synonym="MGC34632"
exon            2179..4755
                    /gene="BDNF"
                    /gene_synonym="MGC34632"
                    /inference="alignment:Splign"
                    /number=11j
polyA_signal    4627..4632
                    /gene="BDNF"
                    /gene_synonym="MGC34632"
                                        Page 2
```

Figure 15 cont.

```
                    NM_170735 human BDNF seq references deleted.txt
    polyA_site      4649
                    /gene="BDNF"
                    /gene_synonym="MGC34632"
    polyA_site      4755
                    /gene="BDNF"
                    /gene_synonym="MGC34632"
ORIGIN
        1 cacacacaca cacacacaca gagagaacat ctctagtaaa aagaaaagtt gagctttctt
       61 agctagatgt gtgtattagc cagaaaaagc caaggagtga agggttttag agaactggag
      121 gagataaagt ggagtctgca tatgggaggc atttgaaatg gacttaaatg tcttttaat
      181 gctgactttt tcagtttct ccttaccaga cacattgttt tcatgacatt agccccaggc
      241 atagacacat cattaaaatg aacatgtcaa aaaatgattt ctgtttagaa ataagcaaaa
      301 cattttcagt tgtgaccacc caggtgtaga ataaagaaca gtggaattgg gagccctgag
      361 ttctaacata aactttcttc atgacataag gcaagtcttc tatggccttt ggtttcctta
      421 cctgtaaaac aggatggctc aatgaaatta tctttcttct ttgctataat agagtatctc
      481 tgtgggaaga ggaaaaaaaa agtcaattta aaggctcctt atagttcccc aactgctgtt
      541 ttattgtgct attcatgcct agacatcaca tagctagaaa ggcccatcag acccctcagg
      601 ccactgctgt tcctgtcaca cattcctgca aaggaccatg ttgctaactt gaaaaaaatt
      661 actattaatt acacttgcag ttgttgctta gtaacattta tgattttgtg tttctcgtga
      721 cagcatgagc agagatcatt aaaaattaaa cttacaaagc tgctaaagtg ggaagaagga
      781 gaacttgaag ccacaatttt tgcacttgct tagaagccat ctaatctcag gttatatgct
      841 agatgcctgt ggcaaacact gcatgtctct ggtttatatt aaaccacata cagcacacta
      901 ctgacactga tttgtgtctg gtgcagctga agtttatcac caagacataa aaaaaccttg
      961 accctgcaga atggcctgga attacaatca gatgggccac atggcatccc ggtgaaagaa
     1021 agccctaacc agttttctgt cttgtttctg ctttctccct acagttccac caggtgagaa
     1081 gagtgatgac catccttttc cttactatgg ttatttcata ctttggttgc atgaaggctg
     1141 cccccatgaa agaagcaaac atccgaggac aaggtggctt ggcctaccca ggtgtgcgga
     1201 cccatggac tctggagagc gtgaatgggc ccaaggcagg ttcaagaggc ttgacatcat
     1261 tggctgacac tttcgaacac gtgatagaag agctgttgga tgaggaccag aaagttcggc
     1321 ccaatgaaga aaacaataag gacgcagact tgtacgtc cagggtgatg ctcagtagtc
     1381 aagtgccttt ggagcctcct cttctctttc tgctggagga atacaaaaat tacctagatg
     1441 ctgcaaacat gtccatgagg gtccggcgc actctgaccc tgcccgccga ggggagctga
     1501 gcgtgtgtga cagtattagt gagtgggtaa cggcggcaga caaaaagact gcagtggaca
     1561 tgtcgggcgg gacggtcaca gtccttgaaa aggtccctgt atcaaaggc caactgaagc
     1621 aatacttcta cgagaccaag tgcaatccca tgggttacac aaaagaaggc tgcaggggca
     1681 tagacaaaag gcattggaac tcccagtgcc gaactaccca gtcgtacgtg cgggcccttta
     1741 ccatggatag caaaaagaga attggctggc gattcataag gatagacact tcttgtgtat
     1801 gtacattgac cattaaaagg ggaagatagt ggatttatgt tgtatagatt agattatatt
     1861 gagacaaaaa ttatctattt gtatatatac ataacagggt aaattattca gttaagaaaa
     1921 aaataatttt atgaactgca tgtataaatg aagtttatac agtacagtgg ttctacaatc
     1981 tatttattgg acatgtccat gaccagaagg gaaacagtca tttgcgcaca acttaaaaag
     2041 tctgcattac attccttgat aatgttgtgg tttgttgccg ttgccaagaa ctgaaaacat
     2101 aaaaagttaa aaaaaataat aaattgcatg ctgcttttaat tgtgaattga taataaactg
     2161 tcctctttca gaaaacagaa aaaaacacac acacacacaa caaaaatttg aaccaaaaca
     2221 ttccgttac attttagaca gtaagtatct tcgttcttgt tagtactata tctgttttac
     2281 tgcttttaac ttctgatagc gttggaatta aaacaatgtc aaggtgctgt tgtcattgct
     2341 ttactgcctt aggggatggg ggatgggga tatttttg ttttgttttgc gtttttttt
     2401 cgtttgtttg ttttgttttt tagttcccac agggagtaga gatggggaaa gaattcctac
     2461 aatatatatt ctggctgata aagatacat ttgtatgttg tgaagatgtt tgcaatatcg
     2521 atcagatgac tagaaagtga ataaaatta aggcaactga acaaaaaaat gctcacactc
     2581 cacatccgt gatgcactc ccaggccccg ctcactttct gggcgttggt cagagtaagc
     2641 tgcttttgac ggaaggacct atgtttgctc agaacacatt cttttcccc ctccccctct
     2701 ggtctcctct ttgttttgtt ttaaggaaga aaaatcagtt gcgcgttctg aaatatttta
     2761 ccactgctgt gaacaagtga acacattgtg tcacatcatg acactcgtat aagcatggag
     2821 aacagtgatt ttttttaga acagaaaaca aggaaaaaata accccaaaat gaagattatt
     2881 ttttatgagg agtgaacatt tgggtaaatc atggctaagc ttaaaaaaaa ctcatggtga
     2941 ggcttaacaa tgtcttgtaa gcaaaaggta gagccctgta tcaacccaga aacacctaga
     3001 tcagaacagg aatccacatt gccagtgaca tgagactgaa cagccaaatg gaggctatgt
     3061 ggagttggca ttgcatttac cggcagtgcg ggaggaattt ctgagtggcc atcccaaggt
     3121 ctaggtggag gtggggcatg gtatttgaga cattccaaaa cgaaggcctc tgaaggaccc
     3181 ttcagaggtg gctctggaat gacatgtgtc aagctgcttg gacctcgtgc tttaagtgcc
     3241 tacattatct aactgtgctc aagaggttct cgactggagg accacactca agccgactta
     3301 tgcccaccat cccacctctg gataatttg cataaaattg gattagcctg gagcaggttg
                                      Page 3
```

Figure 15 cont.

```
     NM_170735 human BDNF seq references deleted.txt
3361 ggagccaaat gtggcatttg tgatcatgag attgatgcaa tgagatagaa gatgtttgct
3421 acctgaacac ttattgcttt gaaactagac ttgaggaaac cagggtttat cttttgagaa
3481 cttttggtaa gggaaaaggg aacaggaaaa gaaacccccaa actcaggccg aatgatcaag
3541 gggacccata ggaaatcttg tccagagaca agacttcggg aaggtgtctg gacattcaga
3601 acaccaagac ttgaaggtgc cttgctcaat ggaagaggcc aggacagagc tgacaaaatt
3661 ttgctcccca gtgaaggcca cagcaacctt ctgcccatcc tgtctgttca tggagagggt
3721 ccctgcctca cctctgccat tttgggttag gagaagtcaa gttgggagcc tgaaatagtg
3781 gttcttggaa aaatggatcc ccagtgaaaa ctagagctct aagcccattc agcccatttc
3841 acacctgaaa atgttagtga tcaccacttg gaccagcatc cttaagtatc agaaagcccc
3901 aagcaattgc tgcatcttag tagggtgagg gataagcaaa agaggatgtt caccataacc
3961 caggaatgaa gataccatca gcaaagaatt tcaatttgtt cagtctttca tttagagcta
4021 gtctttcaca gtaccatctg aatacctctt tgaaagaagg aagactttac gtagtgtaga
4081 tttgttttgt gttgtttgaa aatattatct ttgtaattat ttttaatatg taaggaatgc
4141 ttggaatatc tgctatatgt caactttatg cagcttcctt ttgagggaca aatttaaaac
4201 aaacaacccc ccatcacaaa cttaaaggat tgcaagggcc agatctgtta agtggtttca
4261 taggagacac atccagcaat tgtgtggtca gtggctcttt tacccaataa gatacatcac
4321 agtcacatgc ttgatggttt atgttgacct aagatttatt ttgttaaaat ctctctctgt
4381 tgtgttcgtt cttgttctgt tttgttttgt tttttaaagt cttgctgtgg tctctttgtg
4441 gcagaagtgt ttcatgcatg gcagcaggcc tgttgctttt ttatcgcgat tcccattgaa
4501 aatgtaagta aatgtctgtg gccttgttct ctctatggta aagatattat tcaccatgta
4561 aaacaaaaaa caatatttata tgtattttata taattatgtt attgaaaaaa
4621 attggcatta aaacttaacc gcatcagaac ctattgtaaa tacaagttct atttaagtgt
4681 actaattaac atataatata tgttttaaat atagaatttt taatgttttt aaatatattt
4741 tcaaagtaca taaaa
```

Figure 15 cont.

```
                    NM_006180 human Trkb seq references deleted.txt
LOCUS       NM_006180               5608 bp    mRNA    linear   PRI 15-FEB-2009
DEFINITION  Homo sapiens neurotrophic tyrosine kinase, receptor, type 2
            (NTRK2), transcript variant a, mRNA.
ACCESSION   NM_006180
VERSION     NM_006180.3  GI:65506645
KEYWORDS    .
SOURCE      Homo sapiens (human)
  ORGANISM  Homo sapiens
            Eukaryota; Metazoa; Chordata; Craniata; Vertebrata; Euteleostomi;
            Mammalia; Eutheria; Euarchontoglires; Primates; Haplorrhini;
            Catarrhini; Hominidae; Homo.
COMMENT     REVIEWED REFSEQ: This record has been curated by NCBI staff. The
            reference sequence was derived from BC075804.1, AL533181.3,
            AF410899.1 and BX649001.1.
            On May 16, 2005 this sequence version replaced gi:21361305.

Summary: This gene encodes a member of the neurotrophic tyrosine
            receptor kinase (NTRK) family. This kinase is a membrane-bound
            receptor that, upon neurotrophin binding, phosphorylates itself and
            members of the MAPK pathway. Signalling through this kinase leads
            to cell differentiation. Mutations in this gene have been
            associated with obesity and mood disorders. Alternate
            transcriptional splice variants encoding different isoforms have
            been found for this gene. [provided by RefSeq].

Transcript Variant: This variant (a; also known as TrkB) encodes
            the full-length protein that includes the tyrosine kinase catalytic
            domain. This is the longest isoform (a).

Publication Note: This RefSeq record includes a subset of the
            publications that are available for this gene. Please see the
            Entrez Gene record to access additional publications.
            COMPLETENESS: complete on the 5' end.
PRIMARY     REFSEQ_SPAN         PRIMARY_IDENTIFIER PRIMARY_SPAN        COMP
            1-436               BC075804.1         1-436
            437-455             AL533181.3         1-19
            456-538             AF410899.1         2-84
            539-869             BC075804.1         539-869
            870-3722            AF410899.1         414-3266
            3723-4512           AF410899.1         3268-4057
            4513-5608           BX649001.1         64-1159
FEATURES             Location/Qualifiers
     source          1..5608
                     /organism="Homo sapiens"
                     /mol_type="mRNA"
                     /db_xref="taxon:9606"
                     /chromosome="9"
                     /map="9q22.1"
     gene            1..5608
                     /gene="NTRK2"
                     /gene_synonym="GP145-TrkB; TRKB"
                     /note="neurotrophic tyrosine kinase, receptor, type 2"
                     /db_xref="GeneID:4915"
                     /db_xref="HGNC:8032"
                     /db_xref="HPRD:02712"
                     /db_xref="MIM:600456"
     exon            1..235
                     /gene="NTRK2"
                     /gene_synonym="GP145-TrkB; TRKB"
                     /inference="alignment:Splign"
                     /number=1
     exon            236..357
                                      Page 1
```

Figure 16

```
                    NM_006180 human Trkb seq references deleted.txt
                       /gene="NTRK2"
                       /gene_synonym="GP145-TrkB; TRKB"
                       /inference="alignment:Splign"
                       /number=2
      exon             358..566
                       /gene="NTRK2"
                       /gene_synonym="GP145-TrkB; TRKB"
                       /inference="alignment:Splign"
                       /number=3a
      exon             567..1150
                       /gene="NTRK2"
                       /gene_synonym="GP145-TrkB; TRKB"
                       /inference="alignment:Splign"
                       /number=4
      CDS              939..3455
                       /gene="NTRK2"
                       /gene_synonym="GP145-TrkB; TRKB"
                       /EC_number="2.7.10.1"
                       /note="isoform a precursor is encoded by transcript
                       variant a; BDNF/NT-3 growth factors receptor; tyrosine
                       kinase receptor B"
                       /codon_start=1
                       /product="neurotrophic tyrosine kinase, receptor, type 2
                       isoform a precursor"
                       /protein_id="NP_006171.2"
                       /db_xref="GI:21361306"
                       /db_xref="CCDS:CCDS6671.1"
                       /db_xref="GeneID:4915"
                       /db_xref="HGNC:8032"
                       /db_xref="HPRD:02712"
                       /db_xref="MIM:600456"
                       /translation="MSSWIRWHGPAMARLWGFCWLVVGFWRAAFACPTSCKCSASRIW
                       CSDPSPGIVAFPRLEPNSVDPENITEIFIANQKRLEIINEDDVEAYVGLRNLTIVDSG
                       LKFVAHKAFLKNSNLQHINFTRNKLTSLSRKHFRHLDLSELILVGNPFTCSCDIMWIK
                       TLQEAKSSPDTQDLYCLNESSKNIPLANLQIPNCGLPSANLAAPNLTVEEGKSITLSC
                       SVAGDPVPNMYWDVGNLVSKHMNETSHTQGSLRITNISSDDSGKQISCVAENLVGEDQ
                       DSVNLTVHFAPTITFLESPTSDHHWCIPFTVKGNPKPALQWFYNGAILNESKYICTKI
                       HVTNHTEYHGCLQLDNPTHMNNGDYTLIAKNEYGKDEKQISAHFMGWPGIDDGANPNY
                       PDVIYEDYGTAANDIGDTTNRSNEIPSTDVTDKTGREHLSVYAVVVIASVVGFCLLVM
                       LFLLKLARHSKFGMKDFSWFGFGKVKSRQGVGPASVISNDDDSASPLHHISNGSNTPS
                       SSEGGPDAVIIGMTKIPVIENPQYFGITNSQLKPDTFVQHIKRHNIVLKRELGEGAFG
                       KVFLAECYNLCPEQDKILVAVKTLKDASDNARKDFHREAELLTNLQHEHIVKFYGVCV
                       EGDPLIMVFEYMKHGDLNKFLRAHGPDAVLMAEGNPPTELTQSQMLHIAQQIAAGMVY
                       LASQHFVHRDLATRNCLVGENLLVKIGDFGMSRDVYSTDYYRVGGHTMLPIRWMPPES
                       IMYRKFTTESDVWSLGVVLWEIFTYGKQPWYQLSNNEVIECITQGRVLQRPRTCPQEV
                       YELMLGCWQREPHMRKNIKGIHTLLQNLAKASPVYLDILG"
      sig_peptide      939..1031
                       /gene="NTRK2"
                       /gene_synonym="GP145-TrkB; TRKB"
      mat_peptide      1032..3452
                       /gene="NTRK2"
                       /gene_synonym="GP145-TrkB; TRKB"
                       /product="neurotrophic tyrosine kinase, receptor, type 2
                       isoform a"
      exon             1151..1225
                       /gene="NTRK2"
                       /gene_synonym="GP145-TrkB; TRKB"
                       /inference="alignment:Splign"
                       /number=5
      exon             1226..1297
                       /gene="NTRK2"
                       /gene_synonym="GP145-TrkB; TRKB"
                       /inference="alignment:Splign"
                                        Page 2
```

Figure 16 cont.

```
              NM_006180 human Trkb seq references deleted.txt
              /number=6
exon          1298..1366
              /gene="NTRK2"
              /gene_synonym="GP145-TrkB; TRKB"
              /inference="alignment:Splign"
              /number=7
exon          1367..1521
              /gene="NTRK2"
              /gene_synonym="GP145-TrkB; TRKB"
              /inference="alignment:Splign"
              /number=8
STS           1440..1961
              /gene="NTRK2"
              /gene_synonym="GP145-TrkB; TRKB"
              /standard_name="Ntrk2"
              /db_xref="UniSTS:265675"
exon          1522..1658
              /gene="NTRK2"
              /gene_synonym="GP145-TrkB; TRKB"
              /inference="alignment:Splign"
              /number=9
exon          1659..1791
              /gene="NTRK2"
              /gene_synonym="GP145-TrkB; TRKB"
              /inference="alignment:Splign"
              /number=10
STS           1661..2255
              /gene="NTRK2"
              /gene_synonym="GP145-TrkB; TRKB"
              /standard_name="Ntrk2"
              /db_xref="UniSTS:260424"
exon          1792..2097
              /gene="NTRK2"
              /gene_synonym="GP145-TrkB; TRKB"
              /inference="alignment:Splign"
              /number=11
exon          2098..2133
              /gene="NTRK2"
              /gene_synonym="GP145-TrkB; TRKB"
              /inference="alignment:Splign"
              /number=12
exon          2134..2234
              /gene="NTRK2"
              /gene_synonym="GP145-TrkB; TRKB"
              /inference="alignment:Splign"
              /number=13
STS           2136..2216
              /gene="NTRK2"
              /gene_synonym="GP145-TrkB; TRKB"
              /standard_name="D9S185E"
              /db_xref="UniSTS:147358"
exon          2235..2334
              /gene="NTRK2"
              /gene_synonym="GP145-TrkB; TRKB"
              /inference="alignment:Splign"
              /number=14b
exon          2335..2382
              /gene="NTRK2"
              /gene_synonym="GP145-TrkB; TRKB"
              /inference="alignment:Splign"
              /number=16b
exon          2383..2571
              /gene="NTRK2"
                              Page 3
```

Figure 16 cont.

```
                    NM_006180 human Trkb seq references deleted.txt
                        /gene_synonym="GP145-TrkB; TRKB"
                        /inference="alignment:Splign"
                        /number=17b
     exon            2572..2702
                        /gene="NTRK2"
                        /gene_synonym="GP145-TrkB; TRKB"
                        /inference="alignment:Splign"
                        /number=19
     exon            2703..2875
                        /gene="NTRK2"
                        /gene_synonym="GP145-TrkB; TRKB"
                        /inference="alignment:Splign"
                        /number=20
     exon            2876..3110
                        /gene="NTRK2"
                        /gene_synonym="GP145-TrkB; TRKB"
                        /inference="alignment:Splign"
                        /number=21
     exon            3111..3269
                        /gene="NTRK2"
                        /gene_synonym="GP145-TrkB; TRKB"
                        /inference="alignment:Splign"
                        /number=22
     exon            3270..5608
                        /gene="NTRK2"
                        /gene_synonym="GP145-TrkB; TRKB"
                        /inference="alignment:Splign"
                        /number=23
     STS             3572..3910
                        /gene="NTRK2"
                        /gene_synonym="GP145-TrkB; TRKB"
                        /standard_name="SHGC-12933"
                        /db_xref="UniSTS:60451"
     STS             3853..4037
                        /gene="NTRK2"
                        /gene_synonym="GP145-TrkB; TRKB"
                        /standard_name="G15862"
                        /db_xref="UniSTS:59770"
ORIGIN
        1 aagacggatt ctcagacaag gcttgcaaat gccccgcagc catcatttaa ctgcacccgc
       61 agaatagtta cggtttgtca cccgaccctc ccggatcgcc taatttgtcc ctagtgagac
      121 cccgaggctc tgcccgcgcc tggcttcttc gtagctggat gcatatcgtg ctccgggcag
      181 cgcgggcgca ggcacgcgt tcgcgcacac cctagcacac atgaacacgc gcaagagctg
      241 aaccaagcac ggtttccatt tcaaaaaggg agacagcctc taccgcgatt gtagaagaga
      301 ctgtggtgtg aattagggac cgggaggcgt cgaacggagg aacggttcat cttagagact
      361 aattttctgg agtttctgcc cctgctctgc gtcagccctc acgtcacttc gccagcagta
      421 gcagaggcgg cggcggcggc tccggaatt gggttggagc aggagcctcg ctggctgctt
      481 cgctcgcgct ctacgcgctc agtccccggc ggtagcagga gcctggaccc aggcgccgcc
      541 ggcgggcgtg aggcgccgga gcccggcctc gaggtgcata ccggaccccc attcgcatct
      601 aacaaggaat ctgcgcccca gagagtcccg ggagcgccgc cggtcggtgc ccggccgcgcc
      661 gggccatgca gcgacggccg ccgcggagct ccgagcagcg gtagcgcccc cctgtaaagc
      721 ggttcgctat gccggggcca ctgtgaaccc tgccgcctgc cggaacactc ttcgctccgg
      781 accagctcag cctctgataa gctggactcg gcacgccgc aacaagcacc gaggagttaa
      841 gagagccgca agcgcaggga aggcctcccc gcacgggtgg gggaaagcgg ccggtgcagc
      901 gcggggacag gcactcgggc tggcactggc tgctagggat gtcgtcctgg ataaggtggc
      961 atggacccgc catggcgcgg ctctgggct tctgctggct ggtgtgggc ttctggaggg
     1021 ccgctttcgc ctgtcccacg tcctgcaaat gcagtgcctc tcggatctgg tgcagcgacc
     1081 cttctcctgg catcgtggca tttccgagat tggagcctaa cagtgtagat cctgagaaca
     1141 tcaccgaaat tttcatcgca aaccagaaaa gcttagaaat catcaacgaa gatgatgttg
     1201 aagcttatgt gggactgaga atctgacaa ttgtggattc tggattaaaa tttgtggctc
     1261 ataaagcatt tctgaaaaac agcaacctgc agcacatcaa ttttacccga aacaaactga
     1321 cgagtttgtc taggaaacat ttccgtcacc ttgacttgtc tgaactgatc ctggtgggca
     1381 atccatttac atgctcctgt gacattatgt ggatcaagac tctccaagag gctaaatcca
```

Figure 16 cont.

```
NM_006180 human Trkb seq references deleted.txt
1441 gtccagacac tcaggatttg tactgcctga atgaaagcag caagaatatt cccctggcaa
1501 acctgcagat acccaattgt ggtttgccat ctgcaaatct ggccgcacct aacctcactg
1561 tggaggaagg aaagtctatc acattatcct gtagtgtggc aggtgatccg gttcctaata
1621 tgtattggga tgttggtaac ctggtttcca aacatatgaa tgaaacaagc cacacacagg
1681 gctccttaag gataactaac atttcatccg atgacagtgg gaagcagatc tcttgtgtgg
1741 cggaaaatct tgtaggagaa gatcaagatt ctgtcaacct cactgtgcat tttgcaccaa
1801 ctatcacatt tctcgaatct ccaacctcag accaccactg gtgcattcca ttcactgtga
1861 aaggcaaccc caaaccagcg cttcagtggt tctataacgg ggcaatattg aatgagtcca
1921 aatacatctg tactaaaata catgttacca atcacacgga gtaccacggc tgcctccagc
1981 tggataatcc cactcacatg aacaatgggg actacactct aatagccaag aatgagtatg
2041 ggaaggatga aaacagatt tctgctcact tcatgggctg gcctggaatt gacgatggtg
2101 caaacccaaa ttatcctgat gtaatttatg aagattatgg aactgcagcg aatgacatcg
2161 gggacaccac gaacagaagt aatgaaatcc cttccacaga cgtcactgat aaaaccggtc
2221 gggaacatct ctcggtctat gctgtggtgg tgattgcgtc tgtggtggga ttttgccttt
2281 tggtaatgct gtttctgctt aagttggcaa gacactccaa gtttggcatg aaagatttct
2341 catggtttgg atttgggaaa gtaaatcaa gacaaggtgt tggcccagcc tccgttatca
2401 gcaatgatga tgactctgcc agccactcc atcacatctc caatgggagt aacactccat
2461 cttcttcgga aggtggccca gatgctgtca ttattggaat gaccaagatc cctgtcattg
2521 aaaatcccca gtactttggc atcaccaaca gtcagctcaa gccagacaca tttgttcagc
2581 acatcaagcg ataacatt gttctgaaaa gggagctagg cgaaggagcc tttggaaaag
2641 tgttcctagc tgaatgctat aacctctgtc ctgagcagga caagatcttg gtggcagtga
2701 agacctgaa ggatgccagt gacaatgcac gcaaggactt ccaccgtgag gccgagctcc
2761 tgaccaacct ccagcatgag cacatcgtca agttctatgg cgtctgcgtg gagggcgacc
2821 ccctcatcat ggtctttgag tacatgaagc atgggggacct caacaagttc ctcagggcac
2881 acggccctga tgccgtgctg atggctgagg caacccgcc cacggaactg acgcagtcgc
2941 agatgctgca tatagcccag cagatcgccg cgggcatggt ctacctggcg tcccagcact
3001 tcgtgcaccg cgatttggcc accaggaact gcctggtcgg ggagaacttg ctggtgaaaa
3061 tcggggactt tgggatgtcc cgggacgtgt acagcactga ctactacagg gtcggtggcc
3121 acacaatgct gcccattcgc tggatgcctc cagagagcat catgtacagg aaattcacga
3181 cggaaagcga cgtctggagc ctggggtcg tgttgtggga gattttcacc tatggcaaac
3241 agccctggta ccagctgtca aacaatgagg tgatagagtg tatcactcag ggccgagtcc
3301 tgcagcgacc ccgcacgtgc ccccaggagg tgtatgagct gatgctgggg tgctggcagc
3361 gagagcccca catgaggaag aacatcaagg gcatccatac cctccttcag aacttggcca
3421 aggcatctcc ggtctacctg gacattctag gctagggccc ttttccccag accgatcctt
3481 cccaacgtac tcctcagacg ggctgagagg atgaacatct tttaactgcc gctggaggcc
3541 accaagctgc tctccttcac tctgacagta ttaacatcaa agactccgag aagctctcga
3601 gggaagcagt gtgtacttct tcatccatag acacagtatt gacttctttt tggcattatc
3661 tcttttctc tttcttttct ccttggttgt tcctttttct ttttttaaat tttcttttc
3721 tttttttttt cgtcttccct gcttcacgat tcttacccctt tcttttgaat caatctggct
3781 tctgcattac tattaactct gcatagacaa aggccttaac aaacgtaatt tgttatatca
3841 gcagacactc cagtttgccc accacaacta acaatgcctt gttgtattcc tgcctttgat
3901 gtggatgaaa aaaagggaaa acaaatattt cacttaaact ttgtcacttc tgctgtacag
3961 atatcgagag tttctatgga ttcacttcta tttatttatt attattactg ttcttattgt
4021 ttttggatgg cttaagcctg tgtataaaaa agaaaacttg tgttcaatct gtgaagcctt
4081 tatctatggg agattaaaac cagagagaaa gaagatttat tatgaaccgc aatatgggag
4141 gaacaaagac aaccactggg atcagctggt gtcagtccct acttaggaaa tactcagcaa
4201 ctgttagctg gaagaatgt attcggcacc ttccctgag gacctttctg aggagtaaaa
4261 agactactgg cctctgtgcc atggatgatt cttttcccat caccagaaat gatagcgtgc
4321 agtagagagc aaagatggct tccgtgagac acaaggaggc gcatagtgtg ctcggacaca
4381 gttttgtctt cgtaggttgt gatgatagca ctggtttgtt tctcaagcgc tatccacaga
4441 acctttgtca acttcagttg aaaagaggtg gattcatgtc cagagctcat ttcggggtca
4501 ggtgggaaag ccaagaactt ggaaaagata agacaagcta taattcgga ggcaagtttc
4561 ttttacaatg aacttttcag atctcacttc cctccgaccc ctaacttcca tgcccacccg
4621 tccttttaac tgtgcaagca aaattgtgca tggtcttcgt cgattaatac cttgtgtgca
4681 gacactactg ctccagacgt cgtttccctg ataggtagag cagatccata aaaaggtatg
4741 acttatacaa ttaggggaag ctaatggagt ttattagctg agtatcaatg tctctgcgtt
4801 gtacggtggt gatggttttt aatgaatatg gaccctgaag cctggaaatc ctcatccacg
4861 tcgaacccac aggactgtgg gaagggcaga atcaatccct aagggaaagg aaacctcacc
4921 ctgaggcgat cacatgcact catgtgcact gtacacaggt caagtccctt gctctgggct
4981 ctagttggga gagtggtttc attccaagtg tactccattg tcagtatgct gtttttgttt
5041 ccttcactcc attcaaaaag tcaaaataca aaatttggca cagcatgcca acgggaggct
5101 gtgcccagac caagcactgg aagtgtgctt ctaggcatag tcattggttt tgcaaaaaga
5161 gggctcaaat ttaaatagaa atttacagct atttgaatgg tcagatatac caagaagaa
                                    Page 5
```

Figure 16 cont.

```
                  NM_006180 human Trkb seq references deleted.txt
5221 aaatatttct gttcctcaag aaaacttgct accctctgtg aggggaattt tgctaaactt
5281 gacatcttta taacatgagc cagattgaaa gggagtgatt ttcattcatc ttaggtcatg
5341 ttatttcata tttgtttctg aaggtgcgat agctctgttt taggttttgc ttgcgcctgt
5401 taattactgg aacaccttat ttttcattaa aggctttgaa agccaattct caaaaattca
5461 aaagtgcaaa ttaacagaac aaaaggaaat ccagtagcaa ctgcagtcaa gcgagggagt
5521 tgacaagata aaccttacgt ccattcaagt tatatgctgg cctatgagag atgagagttg
5581 ggtcgtttgt tctctttgtt gatgattt
```

Figure 16 cont.

```
                                   WPRE seq.txt
woodchuck post-transcriptional regulatory element (WPRE)
ATAATCAACCTCTGGATTACAAAATTTGTGAAAGATTGACTGGTATTCTTAACTATGTTGCTCCTTTTAC
GCTATGTGGATACGCTGCTTTAATGCCTTTGTATCATGCTATTGCTTCCCGTATGGCTTTCATTTTCTCC
TCCTTGTATAAATCCTGGTTGCTGTCTCTTTATGAGGAGTTGTGGCCCGTTGTCAGGCAACGTGGCGTGG
TGTGCACTGTGTTTGCTGACGCAACCCCCACTGGTTGGGGCATTGCCACCACCTGTCAGCTCCTTTCCGG
GACTTTCGCTTTCCCCCTCCCTATTGCCACGGCGGAACTCATCGCCGCCTGCCTTGCCCGCTGCTGGACA
GGGGCTCGGCTGTTGGGCACTGACAATTCCGTGGTGTTGTCGGGAAATCATCGTCCTTTCCTTGGCTGC
TCGCCTGTGTTGCCACCTGGATTCTGCGCGGGACGTCCTTCTGCTACGTCCCTTCGGCCCTCAATCCAGC
GGACCTTCCTTCCCGCGGCCTGCTGCCGGCTCTGCGGCCTCTTCCGCGTCTTCGCCTTCGCCCTCAGACG
AGTCGGATCTCCCTTTGGGCCGCCTCCCCGCATC
```

Figure 18

```
                    AF314194 human AGRP gene reference deleted.txt
LOCUS       AF314194                1930 bp    DNA     linear   PRI 24-OCT-2001
DEFINITION  Homo sapiens agouti-related protein gene, promoter and complete
            cds.
ACCESSION   AF314194
VERSION     AF314194.1  GI:15824722
KEYWORDS    .
SOURCE      Homo sapiens (human)
  ORGANISM  Homo sapiens
            Eukaryota; Metazoa; Chordata; Craniata; Vertebrata; Euteleostomi;
            Mammalia; Eutheria; Euarchontoglires; Primates; Haplorrhini;
            Catarrhini; Hominidae; Homo.

FEATURES             Location/Qualifiers
     source          1..1930
                     /organism="Homo sapiens"
                     /mol_type="genomic DNA"
                     /db_xref="taxon:9606"
                     /chromosome="16"
                     /map="16q22"
     promoter        1..700
     mRNA            join(701..997,1113..1245,1404..1489,1696..1930)
                     /product="agouti-related protein"
     CDS             join(1116..1245,1404..1489,1696..1878)
                     /codon_start=1
                     /product="agouti-related protein"
                     /protein_id="AAL09457.1"
                     /db_xref="GI:15824723"
                     /translation="MLTAAVLSCALLLALPATRGAQMGLAPMEGIRRPDQALLPELPG
                     LGLRAPLKKTTAEQAEEDLLQEAQALAEVLDLQDREPRSSRRCVRLHESCLGQQVPCC
                     DPCATCYCRFFNAFCYCRKLGTAMNPCSRT"
ORIGIN
        1 tttntttttt tcactgcctg tgccaccagt tgtgcactgg gccttgcgat cctctcaagc
       61 tgattcagcc tgcatccttc ccagatggac acgtgtgtga taaacagctc tgcagtgggg
      121 tgagggaagg caggggcagc agggtcctgt atgtcctgcc atctccacaa aagggcagtc
      181 cttacccag  ccttgtgctg atgagaccag gcatagacag tcctgacgac acaggcgga
      241 agggagcagc cattagtgct aatgaggcag gcggcctgaa agctttgtac tctgcagtgg
      301 ctcgcccacc cagggaacag ttcgttctgt ttccttggct tccaggaacc ctaggcagaa
      361 aggggtttgg ggacaggagc aggagtgggc ggtcttggag aaacctggag ggagaagggg
      421 aggggaggac cagaaatgta gtcaggaggg cctaggattg gttaggtggg cttttccttc
      481 ccctttccct ccaaagaaac ccaggttctg gttctgcacc tacccctgcc caacagtggc
      541 cattggccca tcaccgctc caatgtcctt gacccgaatt cttggaagca caggaaacaa
      601 catgccacat aggggttgag taagcatctc tggggccaca aattaaatta agctttcagg
      661 gccgcctgcc ttgttattgc taatggttct agccctgctc agctcctagg tccctgtcct
      721 gtggaaattt gtggaccctg ggcacccctct cttgctccca aattttaatc ggctcctgga
      781 aacctcaccc caaattggaa ataggccatc ctccttgtaga acaaaaggct caggttcagg
      841 gagtgagggc ctgaactgtg ccccacct ccaggaaggg tccttcacgg cctggctgca
      901 gggatcagtc acgtgtggcc cttcattagg ccctgccata taagccaagg gcacgggtg
      961 gccgggaact ctctaggcaa gaatcccgga ggcagaggtg agtcctcagg ttgggcaggg
     1021 actcctcctc tctgtggggt ctctatctgg gcaccctagag gggactccaa ggataaggag
     1081 ggactaagtg gtacatcttc ctgctgagcc aggccatgct gaccgcagcg gtgctgagct
     1141 gtgccctgct gctggcactg cctgccacgc gaggagccca gatgggcttg gccccatgg
     1201 agggcatcag aaggcctgac caggccctgc tcccagagct cccaggtcag tgtgagcaag
     1251 ggtgggactg ggcgggcct gaatccctc tggccacaaa tagtctccct tggcataaac
     1321 cctctttctc ccttcccaaa cccctccctg ggaggtgggt gctttgtgca tggggttcc
     1381 tgccctcaca tcctctgccc caggcctggg cctgcgggcc ccactgaaga agacaactgc
     1441 agaacaggca gaagaggatc tgttgcagga ggctcaggcc ttggcagagg taactgctca
     1501 ggggaaaaggg taaggtggtg gcccttggga gggggcattg ggtattagct cctctcccca
     1561 gctccaaact ccctcaccag cgacgacact accgaccacc ccttcccatg ctccactgcc
     1621 atcctgcaca ggttgggaca ggtaagatcc ctggatctgt ctttagaggc ctgtgctggt
     1681 tccccacccc tgcaggtact agacctgcag gaccgcgagc ccgctcctc acgtcgctgc
     1741 gtaaggctgc atgagtcctg cctgggacag caggtgcctt gctgtgaccc atgtgccacg
     1801 tgctactgcc gcttcttcaa tgccttctgc tactgccgca agctgggtac tgccatgaat
                                        Page 1

AF314194 human AGRP gene reference deleted.txt
     1861 ccctgcagcc gcacctagct ggccaacgtc agggtcgggg caaggaaact cgaataaagg
     1921 atgggaccaa
```

Figure 17

TREATMENT OF METABOLIC-RELATED DISORDERS USING HYPOTHALAMIC GENE TRANSFER OF BDNF AND COMPOSITIONS THEREFOR

CROSS-REFERENCE TO RELATED APPLICATIONS

This application claims the benefit of PCT application No. PCT/US2009/038593filed Mar. 27, 2009 which claims priority to U.S. Provisional Application No. 61/072,146, filed Mar. 27, 2008, the disclosure of which is expressly incorporated herein by reference.

STATEMENT REGARDING FEDERALLY SPONSORED RESEARCH

This invention was made with Government support from the National Institutes of Health research grant NS44576 and the government has certain rights in the invention.

TECHNICAL FIELD AND INDUSTRIAL APPLICABILITY OF THE INVENTION

Described herein is a system which uses a combination of a transgene with a physiological regulated microRNA to that same transgene. In one particular aspect, the system uses one vector to deliver both the transgene and an interfering RNA targeting the same transgene. In another particular aspect, this invention is directed to an inventive method that demonstrates a remarkable efficacy on lowering body weight.

BACKGROUND OF THE INVENTION

Obesity and the related condition, syndrome X (or metabolic syndrome) represent two of the most significant causes of morbidity in the western world, and their incidences are growing rapidly. Lifestyle and non-pharmacological approaches have limited efficacy, and particularly in the megaobese (30% or greater of ideal body weight, IBW), pharmacological treatments are being used including stimulants, appetite suppressants and drugs that interfere with fat absorption. Moreover, bariatric surgery has increased dramatically reflecting just how problematic and refractory severe obesity is to alternative less invasive strategies. Bariatric surgery is often effective but comes with significant morbidity in its own right, hence there is a need for a safer and more effective approach.

Gene expression studies have been conducted in the hypothalamus of animals which lived in an optimized enriched environment (where such animals have increased physical and social activity which results in a much healthier and resilient animal). These animals have improved insulin sensitivity, have reduced fat mass and, despite ad libitum food, do not gain weight to obese levels as do control standard housed animals. The inventors' previous gene expression studies showed a consistent elevation in BDNF in the hypothalamus at 2, 4 and 9 weeks of enrichment. Many other genes changed at various timepoints of enrichment but were not consistently upregulated.

There is a need, therefore, for a method to regulate the metabolic and related disorders without the drawbacks associated with the currently recommended treatments.

Considering the above-mentioned, there is also a need for therapeutic strategies to treat such metabolic and related disorders.

SUMMARY OF THE INVENTION

The invention is based, at least in part, on the inventors' discovery that gene transfer of brain-derived neurotrophic factor (BDNF) to the hypothalamus can lead to an insulin-sensitive, lean and healthy phenotype in ad libitum fed animals.

In a first aspect, there is provided herein a gene therapy particle comprising: one or more of: i) a nucleotide sequence encoding at least one neurotropin, or a derivative or functional fragment thereof, that binds to a receptor capable of being delivered to a subject in need thereof for therapy of a metabolic disorder; ii) a nucleotide sequence encoding at least one receptor for the neurotropin, or a derivative or functional fragment thereof, that binds to a receptor capable of being delivered to a subject in need thereof for therapy of a metabolic disorder; and iii) a nucleotide sequence that mediates or facilitates the signaling of at least one neurotropin, or a derivative or functional fragment thereof, that binds to a receptor capable of being delivered to a subject in need thereof for therapy of a metabolic disorder.

In certain embodiments, the neurotropin comprises a brain derived neurotrophic factor (BDNF), or a derivative or functional fragment thereof.

In certain embodiments, the receptor comprises a receptor (trkB) or any analogue or variant capable of transducing one or more of the neurotropin's effects.

In certain embodiments, the gene therapy particle targets a nucleotide sequence encoding at least one neurotropin.

In certain embodiments, the gene therapy particle targets any flanking 5' or 3' sequence of the nucleotide sequence encoding at least one neurotropin, including untranslated sequences.

In certain embodiments, the receptor comprises a trkB receptor and the neurotropin comprises BDNF.

In another aspect, there is provided herein a gene therapy particle comprising a combination of a transgene with a physiological regulated RNA to that same transgene, or with a transgene mRNA including all untranslated 3' and 5' sequences, the gene therapy particle being capable of being delivered to a subject in need thereof for therapy of a metabolic disorder. In certain embodiments, the interfering RNA can comprise one or more of: a micro RNA, a short hairpin (shRNA) or short interfering (siRNA), and any other form of interfering RNA, including but not limited to a WPRE sequence.

In another aspect, there is provided herein a gene therapy particle comprising a vector expression cassette, a regulatory gene sequence, and a nucleotide sequence encoding a brain derived neurotrophic factor (BDNF), derivative or functional fragment thereof.

In another aspect, there is provided herein a recombinant gene therapy particle comprising a nucleotide sequence containing a vector expression cassette having an enhancer and promoter, a regulatory gene sequence, wherein the nucleotide sequence encodes a brain derived neurotrophic factor (BDNF), derivative or functional fragment thereof, and wherein the nucleotide sequence is inserted to one or more cloning sites between the promoter and the regulatory sequence.

In certain embodiments, the nucleotide sequence encodes TrkB or any variant capable of transducing BDNF effects.

In certain embodiments, the vector is an adeno-associated viral vector, lentiviral vector or adenoviral vector. In certain embodiments, the vector is an adeno-associated viral vector selected from the serotype of one or more of: AAV-1, AAV-2, AAV-3, AAV-4, AAAV-5, AAV-6, AAV-7, AAV-8, AAV-9 and AAV-10. In certain embodiments, the vector is any human or non-human primate isolate, variant, recombinant, chimeric or AAV capsid, including mutations, substitutions, deletions or additions. In certain embodiments, the adeno-associated viral vector is AAV-2, or a modified form of AAV-2 with an altered tropism. In certain embodiments, the AAV nucleotide sequences are derived from AAV serotype 1 (AAV-1).

In certain embodiments, the nucleotide sequence includes the DNA sequence represented by SEQ ID NO:1.

In certain embodiments, the nucleotide sequence includes the DNA sequence represented by AGRP484 (484 bp, −133 bp to +351 bp from the start of the noncoding exon28) in SEQ ID NO:7.

In certain embodiments, the nucleotide sequence includes the DNA sequence represented by AGRP814 (814 bp, −463/+351) in SEQ ID NO:7.

In certain embodiments, the nucleotide sequence is a human BDNF protein sequence.

In another aspect, there is provided herein a pharmaceutical composition comprising the gene therapy particle, in a biocompatible pharmaceutical carrier.

In another aspect, there is provided herein a method of gene therapy for the treatment of a subject having a mutation or polymorphism in the BDNF gene comprising: administering a therapeutically effective amount of a recombinant gene therapy particle to cells of the subject, wherein the gene therapy particle comprises the gene particle.

In certain embodiments, the gene therapy particle comprises the sequence represented by SEQ ID NO:1. In certain embodiments, the gene therapy particle comprises the sequence represented by AGRP484 (484 bp, −133 bp to +351 bp from the start of the noncoding exon28) in SEQ ID NO:7. In certain embodiments, the gene therapy particle comprises the sequence represented by AGRP814 (814 bp, −463/+351) in SEQ ID NO:7.

In certain embodiments, the gene therapy particle is administered by a stereotactic route. In certain embodiments, the gene therapy particle is administered by an approach via the subject's ventricles, with or without an endoscope. In certain embodiments, the gene therapy particle is administered via the subject's lateral ventricle, through to the third ventricle which lies immediately adjacent to the hypothalamus. In certain embodiments, the gene therapy particle is administered via a transnasal approach. In certain embodiments, the gene therapy particle is administered transphenoidally, in which a direct approach through the nasal sinuses to the base of the brain, and then a device inserted to deliver the vector directly through this skull base approach into the hypothalamus. In certain embodiments, the gene therapy particle is administered into the subject's ventricles with sufficient hypothalamic expression obtained to induce weight loss.

In certain embodiments, the cells of the subject are brain hypothalamic cells. In certain embodiments, the cells of the subject are hypothalamic cells responsible for the control of food intake and/or the subject's metabolism. In certain embodiments, the subject is a primate. In certain embodiments, the subject is a human.

In certain embodiments, the particle is in a biocompatible pharmaceutical carrier.

In another aspect, there is provided herein a method of reducing or eliminating metabolic-related disorder symptoms comprising administering to a subject in need thereof a therapeutically effective amount of the gene therapy particle. In certain embodiments, the metabolic-related disorder symptoms are one or more of obesity, insulin sensitivity, syndrome X and diabetes.

In another aspect, there is provided herein a method for ameliorating a symptom of a metabolic system disorder in a mammal, the method comprising direct administration of an adeno-associated virus-derived vector to a target cell in the brain of the mammal, the vector comprising a DNA sequence, wherein the DNA sequence is exogenous to an adeno-associated virus and comprises a sequence encoding a therapeutic protein in operable linkage with a promoter sequence, wherein the adeno-associated virus-derived vector is free of both wild-type and helper virus, and wherein the exogenous DNA sequence is expressed in the target cell such that the symptom of the metabolic disorder is ameliorated.

In certain embodiments, the exogenous DNA sequence is expressed in the target cell either constitutively or under regulatable conditions.

In certain embodiments, the exogenous DNA sequence encodes a brain derived neurotrophic factor (BDNF) protein.

In certain embodiments, all adeno-associated viral genes of the vector have been deleted or inactivated.

In certain embodiments, the vector comprises only the inverted terminal repeats of adeno-associated virus.

In certain embodiments, the promoter sequence is a central nervous system-specific promoter. In certain embodiments, the target cell is a primate target cell. In certain embodiments, the primate target cell is a human target cell.

In certain embodiments, direct administration is by stereotaxic injection.

In another aspect, there is provided herein an adeno-associated virus-derived vector comprising only the replication and packaging signals of adeno-associated virus, and further comprising a nucleotide sequence encoding a brain derived neurotrophic factor (BDNF), or a derivative or functional fragment thereof, and a promoter sequence.

In another aspect, there is provided herein a method for delivering a nucleotide sequence to a mammalian nervous system target cell, the method comprising administering an expression vector to the target cell, wherein the expression vector comprises a nucleotide sequence encoding brain derived neurotrophic factor (BDNF), or a derivative or functional fragment thereof.

In certain embodiments, the nucleotide sequence encoding BDNF, or a derivative or functional fragment thereof, is expressed in the target cell either constitutively or under regulatable conditions.

In certain embodiments, expression of BDNF, or a derivative or functional fragment thereof, in the target cell alters neuronal excitability.

In certain embodiments, expression of BDNF, or a derivative or functional fragment thereof, in the target cell reduces neuronal excitability.

In certain embodiments, expression of BDNF, or a derivative or functional fragment thereof, in the target cell reduces symptoms associated with a metabolic disorder.

In certain embodiments, the metabolic disorder is one or more of obesity, insulin sensitivity, syndrome X and diabetes.

In certain embodiments, the expression vector is a viral or a non-viral expression vector. In certain embodiments, the viral expression vector is an adeno-associated virus (AAV) vector. In certain embodiments, the viral expression vector is an AAV vector capable of transducing the target cell and the AAV vector is free of both wildtype and helper virus.

In certain embodiments, the AAV vector is a serotype 2 AAV vector or a chimeric serotype ½ AAV vector.

In certain embodiments, the nucleotide sequence comprises SEQ ID NO:1.

In certain embodiments, the nucleotide sequence comprises AGRP484 (484 bp, −133 bp to +351 bp from the start of the noncoding exon28) in SEQ ID NO:7.

In certain embodiments, the nucleotide sequence comprises AGRP814 (814 bp, −463/+351) in SEQ ID NO:7.

In certain embodiments, the nucleotide sequence encoding BDNF, or a derivative or functional fragment thereof, is operably linked to an inducible regulatory sequence.

In certain embodiments, the inducible regulatory sequence renders BDNF expression central nervous system-specific. In certain embodiments, the target cell is a mammalian cell. In certain embodiments, the target cell is a human cell. In certain embodiments, the target cell is in cell culture. In certain embodiments, the target cell is in a living mammal.

In certain embodiments, the method includes delivering nucleic acid encoding BDNF to cells of the nervous system to effect expression of BDNF in cells of the nervous system to treat a metabolic disorder. In certain embodiments, the metabolic-related disorder symptoms are one or more of obesity, insulin sensitivity, syndrome X and diabetes.

In certain embodiments, the nucleic acid sequence encoding BDNF is a nucleic acid sequence encoding an amino acid sequence comprising SEQ ID NO:1, AGRP484 (484 bp, −133 bp to +351 bp from the start of the noncoding exon28) in SEQ ID NO:7 or AGRP814 (814 bp, −463/+351) in SEQ ID NO:7, or a derivative or functional fragment thereof; an amino acid sequence at least 90% homologous thereto; or an amino acid sequence at least 85% homologous thereto. In certain embodiments, the administering is by stereotaxic microinjection.

In another aspect, there is provided herein an AAV vector which retains only the replication and packaging signals of AAV, and which comprises a nucleotide sequence encoding BDNF, or a derivative or a functional fragment thereof. In certain embodiments, the AAV vector, wherein the nucleic acid sequence comprises a nucleic acid sequence of SEQ ID NO:1, AGRP484 (484 bp, −133 bp to +351 bp from the start of the noncoding exon28) in SEQ ID NO:7 or AGRP814 (814 bp, −463/+351) in SEQ ID NO:7, or a derivative or a functional fragment thereof.

In another aspect, there is provided herein a composition comprising an AAV vector and a pharmaceutically acceptable carrier.

In another aspect, there is provided herein a method for treating a mammal with a metabolic disorder, the method comprising administering an expression vector to a target cell in the mammal, wherein the expression vector comprises a nucleic acid sequence encoding BDNF, or a derivative or functional fragment thereof, and wherein the administering results in expression of BDNF, or a derivative or functional fragment thereof, in the target cell and the expression reduces the symptoms of the metabolic disorder, thereby treating the mammal with such disorder. In certain embodiments, the expression vector is a viral or a non-viral expression vector. In certain embodiments, the viral expression vector is an adeno-associated virus (AAV) vector. In certain embodiments, the nucleic acid sequence encoding BDNF is a nucleic acid sequence encoding an amino acid sequence comprising SEQ ID NO:1, AGRP484 (484 bp, −133 bp to +351 bp from the start of the noncoding exon28) in SEQ ID NO:7 or AGRP814 (814 bp, −463/+351) in SEQ ID NO:7, or a derivative or a functional fragment thereof; or an amino acid sequence at least 90% homologous thereto; or an amino acid sequence at least 85% homologous thereto. In certain embodiments, the metabolic disorder is obesity. In certain embodiments, the administering is by stereotaxic microinjection.

In another aspect, there is provided herein a method for delivering a nucleotide sequence to a mammalian nervous system target cell, the method comprising administering an adeno-associated virus (AAV) vector to the target cell, wherein the vector transduces the target cell; and wherein the AAV vector comprises an AAV vector, and is free of both wildtype and helper virus.

In another aspect, there is provided herein a method for treating a mammal with a metabolic disorder, the method comprising administering an adeno-associated virus (AAV) vector to a target cell in the mammal, wherein the AAV vector comprises an AAV vector, and wherein the administering results in expression of BDNF, or a derivative or functional fragment thereof, in the target cell and the expression reduces the symptoms of the metabolic disorder, thereby treating the mammal with such disorder.

In certain embodiments, the method includes a single dosing to which the mammal responds, and yet adapts and auto-regulates regardless of the mammal's diet.

In certain embodiments, the metabolic disorder is obesity, and the reduction of symptoms includes one or more of: loss of liver steatosis, improvement in insulin sensitivity, improvement in glucose tolerance, and reversal of hyperleptinemia and lipid dyslipidemia.

In another aspect, there is provided herein a method for regulation of a given functional transgene of interest, wherein the transgene is self-regulated by a microRNA driven by one or more promoters activated, in turn, by a physiological change induced by the transgene of interest.

In another aspect, there is provided herein a method for regulating one or more genes encoding proteins involved in energy expenditure in a subject in need thereof, comprising upregulating Ucps in the subject's liver.

In another aspect, there is provided herein a method for causing reversible weight gain, comprising knocking out a BDNF transgene by expression of Cre.

In another aspect, there is provided herein an autoregulatory negative feedback system comprising using RNAi coupled with a transgene for inducing one or more physiological changes.

In another aspect, there is provided herein a knockout system comprising using delivery of a second, rescue vector, comprising using a loxP-Cre recombination system to knock out a nucleotide sequence encoding for BDNF or a derivative or functional fragment thereof.

In another aspect, there is provided herein a rAAV vector comprising a BDNF transgene flanked by two loxP sites (flox-BDNF), capable of being subsequently knocked out by a second viral vector delivering Cre recombinase.

In certain embodiments, the rAAV vector encodes a GFP-Cre fusion protein.

In another aspect, there is provided herein a method for ablating loxP-modified genes in the brain, including the hypothalamus, with low toxicity, comprising administering an effective amount of the rAAV vector.

In certain embodiments, the vector expression cassette includes a promoter selected from: chicken β-actin (CBA), agouti related protein 484 (AGRP484), and agouti related protein 84 (AGRP814).

In another aspect, there is provided herein an rAAV plasmid comprising a vector expression cassette consisting of an enhancer, a promoter, a regulatory element and bovine growth hormone polyadenosine flanked by AAV inverted terminal repeats, wherein fused human BDNF cDNA is fused at the 5' terminus and then inserted into at least one multiple cloning site between the promoter and the sequence.

In another aspect, there is provided herein an rAAV plasmid comprising a vector expression cassette consisting of a cytomegalovirus enhancer, a chicken β-actin (CBA) promoter, a woodchuck post-transcriptional regulatory element (WPRE) and bovine growth hormone polyadenosine flanked by AAV inverted terminal repeats, wherein fused human BDNF cDNA is fused at the 5' terminus and then inserted into multiple cloning sites between the CBA promoter and the WPRE sequence.

In certain embodiments, the rAAV plasmid includes a weaker promoter to drive the BDNF, wherein, in the obese state the AGRP promoter is dialed right down, but is activated when weight is lost, and wherein, at target weight, the AGRP promoter is stronger than the promoter driving the BDNF.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file contains at least one drawing excuted in color. Copies of this patent with color drawings will be provided by the United States Patent and Trademark Office upon request and payment of necessary fee.

FIG. 1a: EGFP fluorescence. Scale bar, 200 μm. ARC, arcuate nucleus; VMH, ventromedial hypothalamus; DMH, dorsalmedial hypothalamus; 3V, third ventricle.

FIG. 1b: Immunoreactivity to HA tag. Scale bar, 200 μm.

FIG. 1c: Colocalization of HA (red) with NPY (green) in arcuate nucleus. Scale bar, 10 μm.

FIG. 1d: Body weight in GFP-expressing (n=10) and BDNF-expressing mice (n =14), *P<0.0001.

FIG. 1e: Perigonadal white adipose tissue weight (n=8 GFP-expressing mice and n=10 BDNF-expressing mice, *P<0.001).

FIG. 1f: Gene expression in hypothalamus (n=4 per group, P values are shown on the bars). Ntrk2, neurotrophic tyrosine kinase, receptor, type 2; Sgk1, serum/glucocorticoid-regulated kinase-1; Vgf, nerve growth factor inducible.

FIG. 2a: Body weight (n=9 GFP-expressing mice and n=10 BDNF-expressing mice, *P<0.0001). Diet was switched from NCD to HFD on day 10 after rAAV injection.

FIG. 2b: Two months HFD feeding led to abdominal obesity in YFP-expressing mice but not in BDNF-expressing mice. Arrow shows pericardial fat absent in the BDNF-expressing mouse. Scale bar, 1 cm.

FIG. 2c: Fat pad weight 72 d after rAAV injection in mice fed on HFD for 2 months (n=8 per group, *P<0.0001).

FIG. 2d: H&E-stained WAT section showing the smaller size of adipose cells in BDNF-expressing mice compared to YFP-expressing mice. Scale bar, 300 μm.

FIGS. 2e-2f: Hepatic steatosis was prevented by BDNF treatment, as shown by oil red O (FIG. 2e) and H&E (FIG. 2f) staining. Scale bar, 300 μm.

FIGS. 2g-2h: Glucose tolerance test after overnight fast (n=4 per group, P<0.0001 for both glucose concentration (FIG. 2g) and insulin (FIG. 2h) concentration).

FIG. 4a: Schematic of the rAAV vectors. The autoregulatory vector contains two expression cassettes, one to express BDNF under a constitutive promoter, the other to express a microRNA targeting the same transgene driven by a promoter (AGRP484) responsive to BDNF-induced physiological changes. PolyA, polyadenosine sequence.

FIG. 4b: Body weight of db/db mice (n=8 YFP-expressing mice, n=7 BDNF-miR-scr-expressing mice and n=9 BDNF-miR-Bdnf-expressing mice; P<0.0001 for comparisons between each pair of groups).

FIG. 4c: Mice receiving BDNF-miR-Bdnf remained lean 3 months after rAAV injection. Scale bar, 1 cm.

FIG. 4d: Food intake in BDNF-treated mice compared to YFP-expressing mice. P values are shown over the bars.

FIG. 4e: Liver weight and fat pad weight in YFP-expressing and BDNF-miR-Bdnf-expressing mice (n=8 each group, *P<0.001).

FIGS. 4f-4g: Glucose tolerance test on mice after overnight fast (n=6 YFP-expressing mice and n=5 BDNF-miR-Bdnf-expressing mice; P<0.05 for glucose concentration (FIG. 4f) and P<0.0001 for insulin concentration (FIG. 4g).

FIG. 4h: Biomarkers in serum 1 month after rAAV injection (n=8 YFP-expressing mice, n=4 BDNF-miR-scr-expressing mice and n=9 BDNF-miR-Bdnf-expressing mice; *P<0.001, +P<0.05 and #P=0.06). IGF-1, insulin-like growth factor-1.

FIG. 5a: Weight change of wild-type mice after first rAAV injection (n=10 YFP-expressing mice and n=24 flox-BDNF-expressing mice, P<0.01).

FIGS. 5b-5d: Effect of BDNF treatment on energy expenditure. Energy expenditure (heat, FIG. 5b), physical activity (FIG. 5c) and respiratory exchange ratio (RER, FIG. 5d) were significantly increased in BDNF-expressing mice (n=5 YFP-expressing mice and n=6 flox-BDNF-expressing mice, P<0.05) during both light and dark cycles.

FIG. 5e: Glucose tolerance test on mice after overnight fast (n=7 YFP-expressing mice and n=9 flox-BDNF-expressing mice, 3 weeks after first rAAV injection; P<0.05).

FIG. 5f: Weight change of mice since second rAAV injection (n=10 mice given YFP and Cre, n=7 mice given flox-BDNF and empty vector and n=14 mice given flox-BDNF and Cre; P<0.05 flox-BDNF+Cre versus flox-BDNF+empty).

FIG. 5g: Body mass index (BMI) of mice 4 months after the first surgery (n=5 mice given YFP and Cre, n=4 mice given flox-BDNF and empty vector and n=6 mice given flox-BDNF and Cre; P values are shown above the bars).

FIG. 5h: Volumetric bone mineral density (vBMD) of whole body (excluding skull) and right femur, as measured by microcomputed tomography scan (n=3 mice given YFP and n=4 mice given flox-BDNF).

FIG. 6c: Hypothalamic gene transfer of BDNF improved insulin tolerance test in diet induced obesity model. Insulin was injected to mice without a fast and blood glucose concentration was measured (n=4 YFP, n=5 BDNF, P<0.0001).

compared to counterlateral side. TUNEL assay showed no apoptosis in hypothalamus injected with rAAV-BDNF or rAAV-Cre.

Figure 7A:
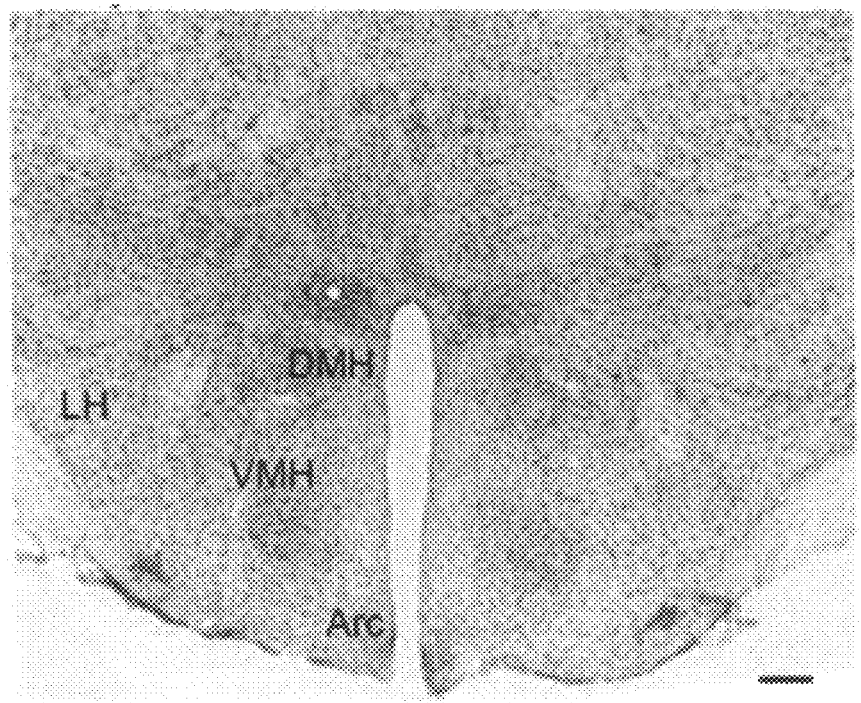
FIGS. 7a-7e: rAAV mediated RDNF overexpression did not cause cytotoxicity. rAAV-BDNF was injected unilaterally to hypothalamus with no cell loss as shown in Nissl staining (FIG. 7a), no gliosis as shown in GFAP staining (FIG. 7b)
Figure 7B:
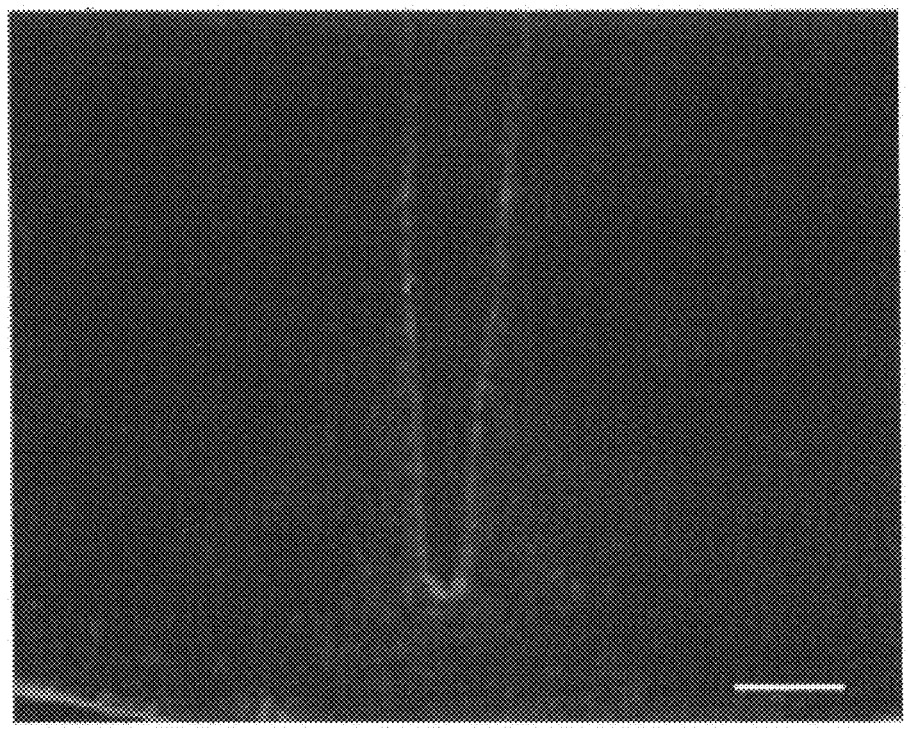
Figures 7C, 7D, 7E:
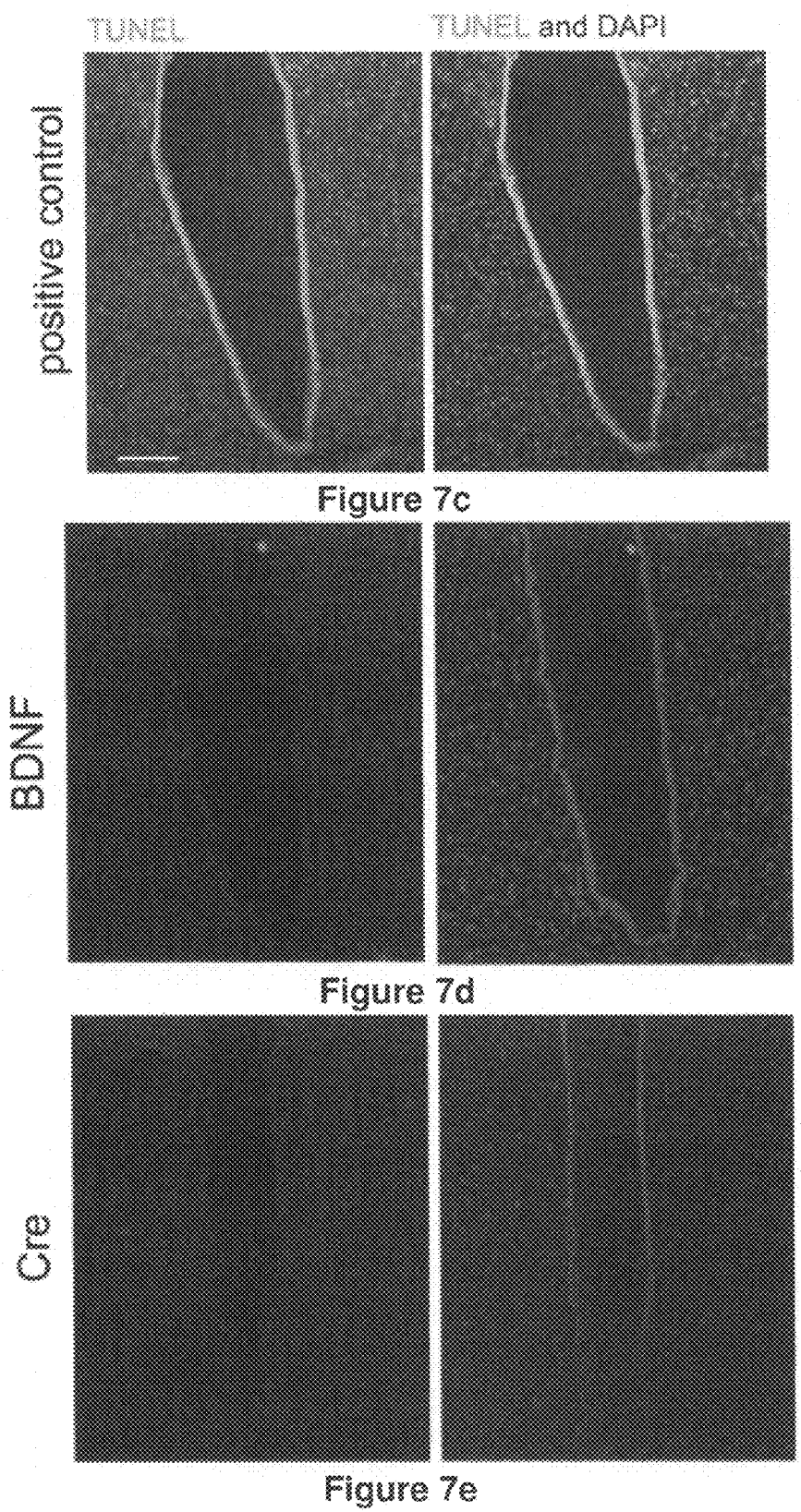

FIG. 7c: TUNEL assay positive control counterstained with DAPI (FIG. 7d) unilateral injection of rAAV-BDNF. (FIG. 7e) bilateral injection of rAAV-Cre. Scale bars 200 μm.

Figure 8A:
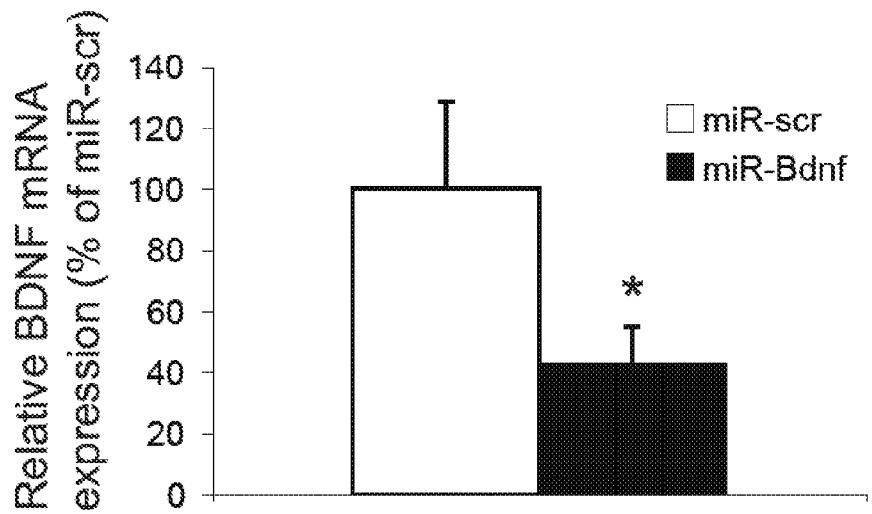
Figure 8B:
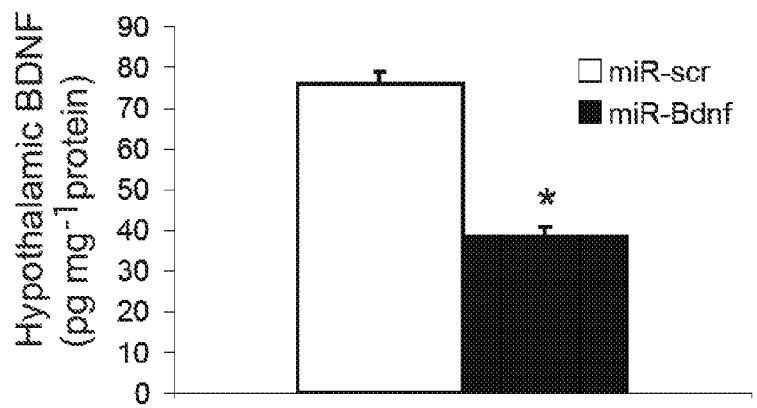
Figure 8C:
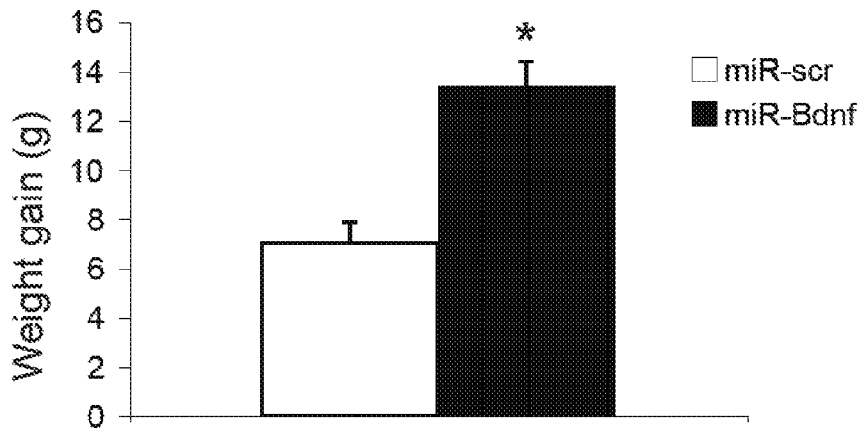

FIG. 8: MicroRNA vector knocked down hypothalamic BDNF expression and led to accelerated weight gain. In vitro experiments showed that the microRNA vector knocked down BDNF mRNA by 65% and protein levels by 80%. We further assessed the efficacy of this microRNA to BDNF by generating a rAAV vector with miR-Bdnf driven by CBA promoter. We also generated a control microRNA vector targeting a scrambled sequence (miR-scr) against no known genes. We injected rAAV vectors of miR-Bdnf or miR-scr bilaterally into the hypothalamus of wild-type mice and fed the mice on standard diet. Quantitative RT-PCR and ELISA showed that the miR-Bdnf vector significantly reduced BDNF expression in hypothalamus at both mRNA (a, *P<0.01) and protein levels compared to miR-scr (b, *P<0.01). This reduction of BDNF expression in hypothalamus led to accelerated weight gain in miR-Bdnf mice by 26 days after injection (c, *P<0.01). n=10-23 per group.

Figure 9A:
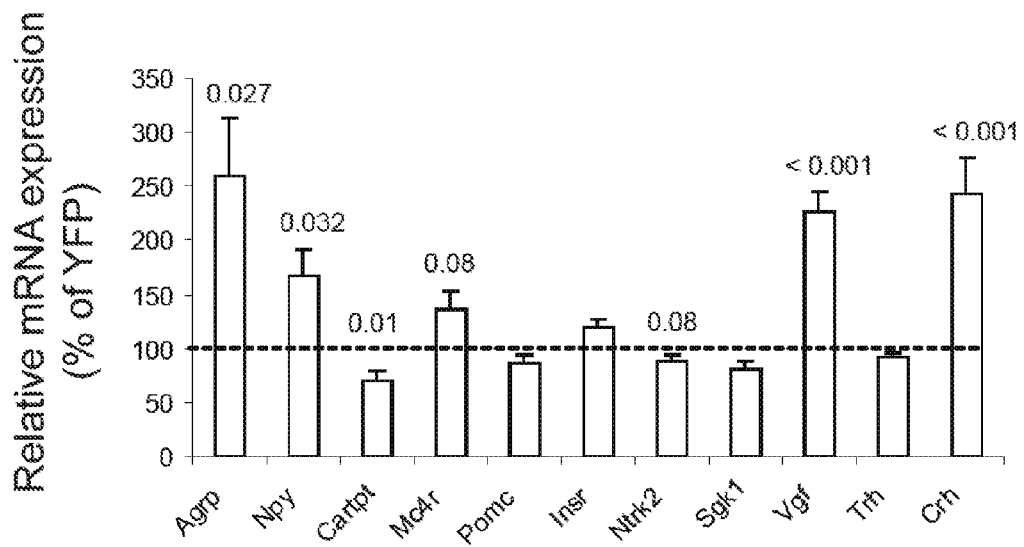

FIG. 9a: Hypothalamic gene expression profile of db/db mice treated with an autoregulatory BDNF vector. Relative mRNA expression levels of the indicated genes in hypothalamus are shown as percentage of control mice (n=6 YFP, n=9 BDNF-miR-Bdnf).

Figure 9B:
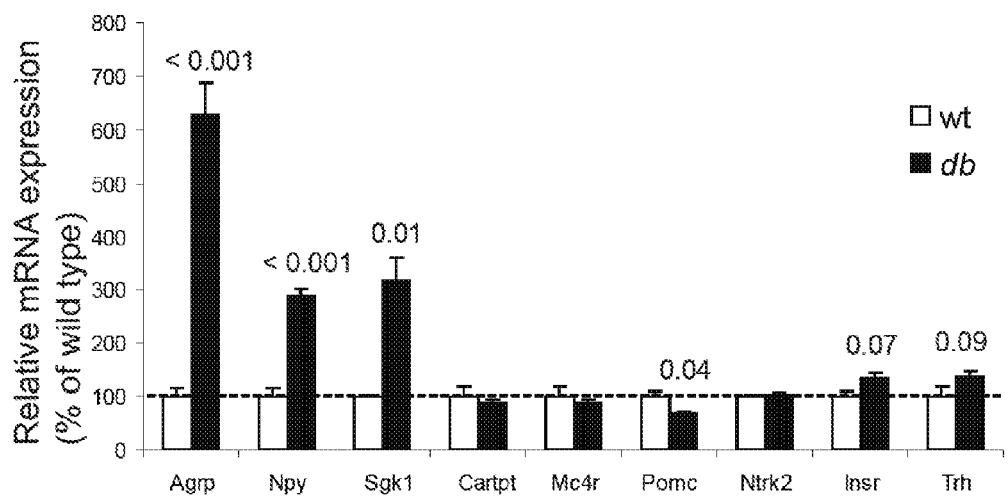

FIG. 9b: Hypothalamic gene expression profile of db/db mice compared to wild type mice. n=6 db/db, n=4 wild type. P values of significance or strong trend are shown on the bars.

Figure 10A:
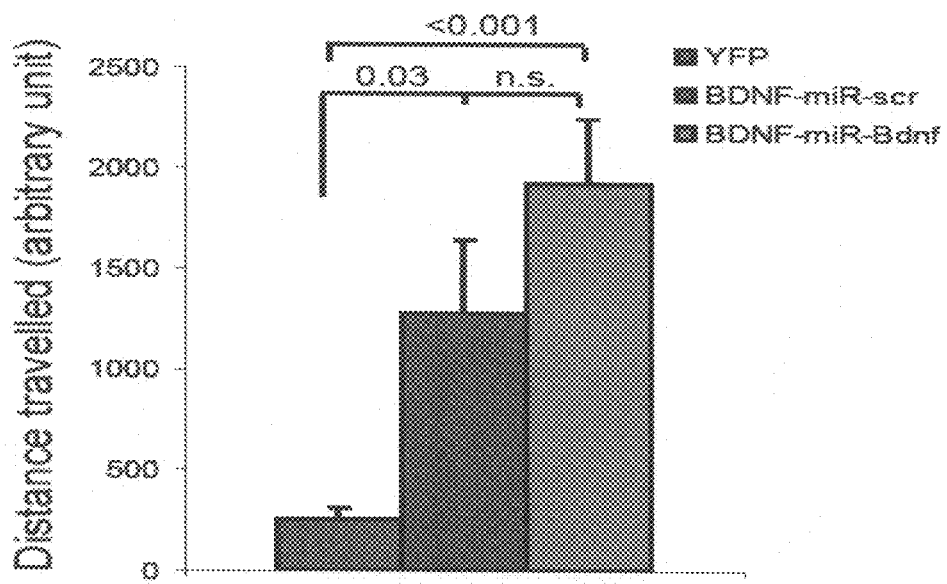
Figure 10B:
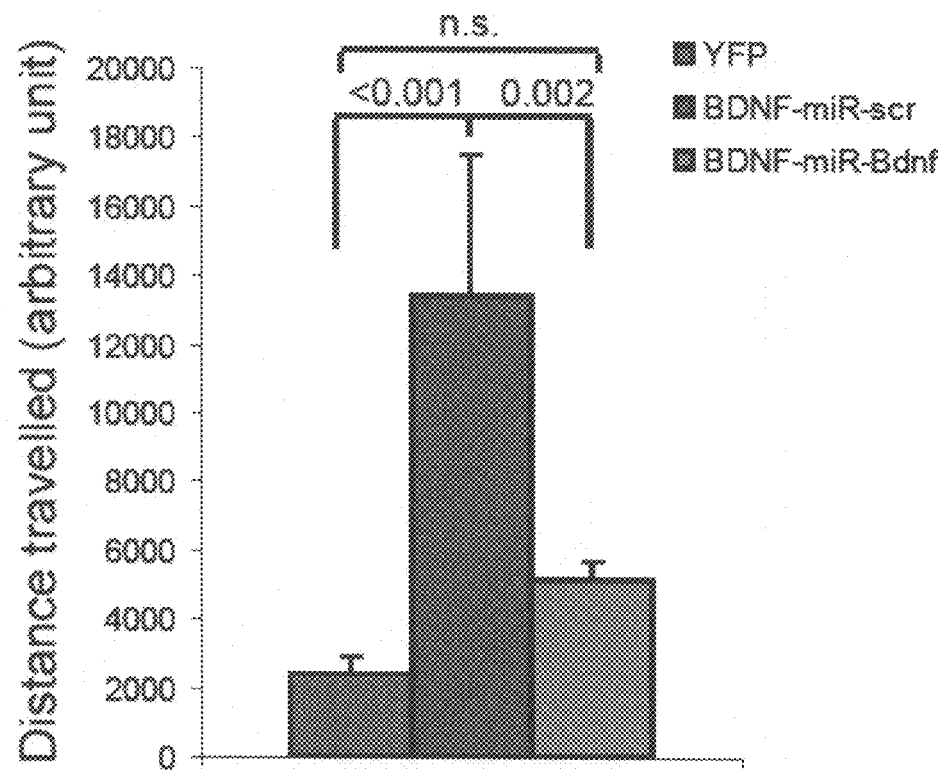
Figure 10C:
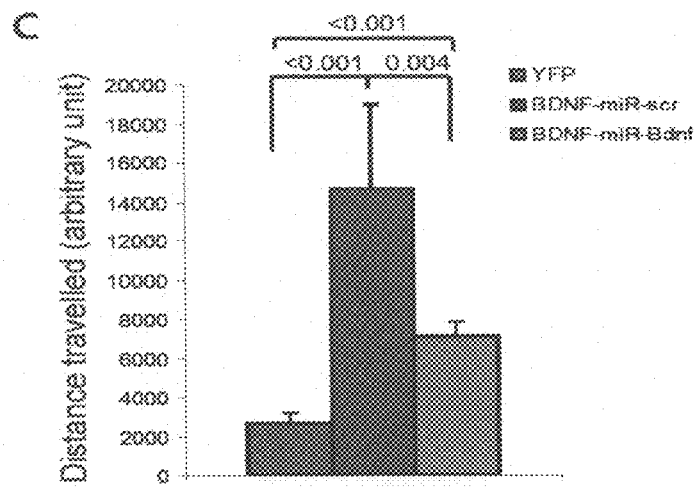
Figure 10D:
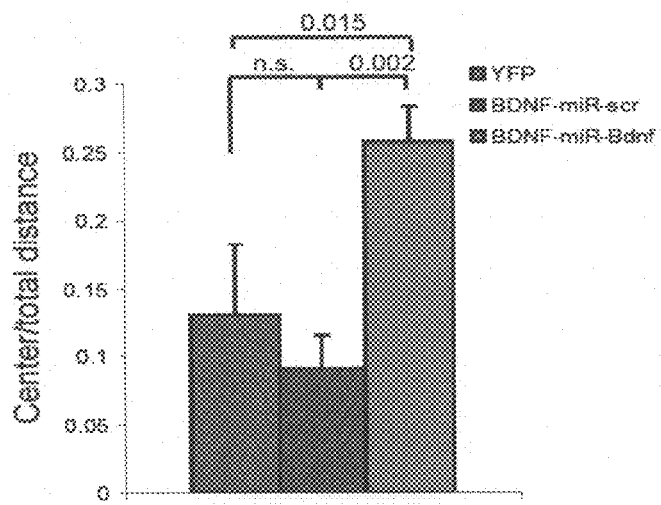
Figure 10E:
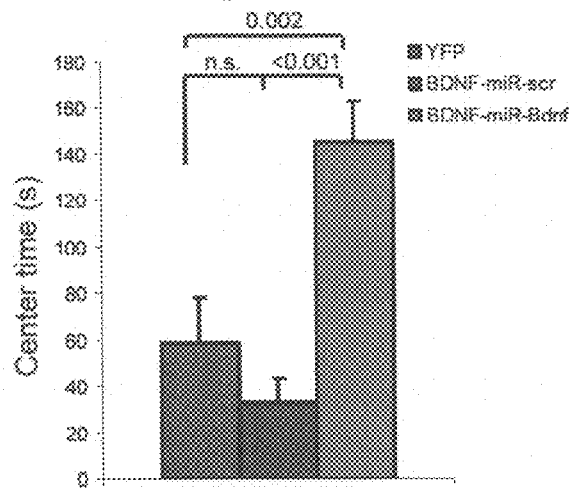

FIGS. 10a 10e: Hypothalamic gene therapy with an autoregulatory BDNF vector improved mobility and exploration behavior of obese db/db mice.

FIG. 10a: Central distance.
FIG. 10b: Peripheral distance.
FIG. 10c: Total distance.
FIG. 10d: Ratio of central to total distance.
FIG. 10e: Center time. n=6 YFP, n=5 BDNF-miR-scr, n=9 BDNF-miR-Bdnf. P values are shown on the bars.

Figure 11A:
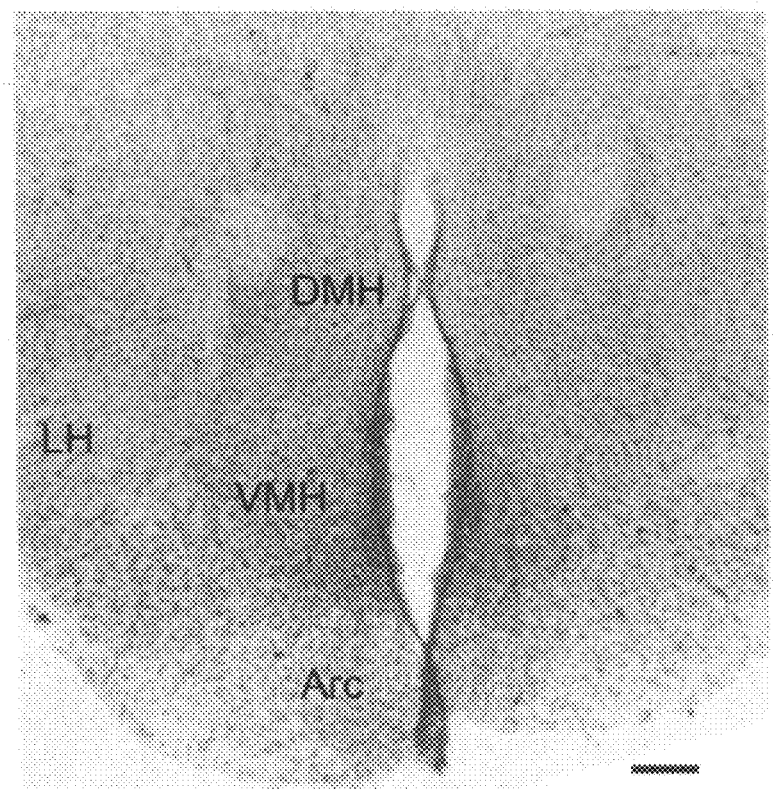
Figure 11B:

FIGS. 11a-11b: Injection of rAAV-GFPICre vector did not cause cell loss as shown with Nissl staining (FIG. 11a) or Oasis as shown by GFAP staining (FIG. 11b). Scale bars: 200 lam.

Figure 11C:
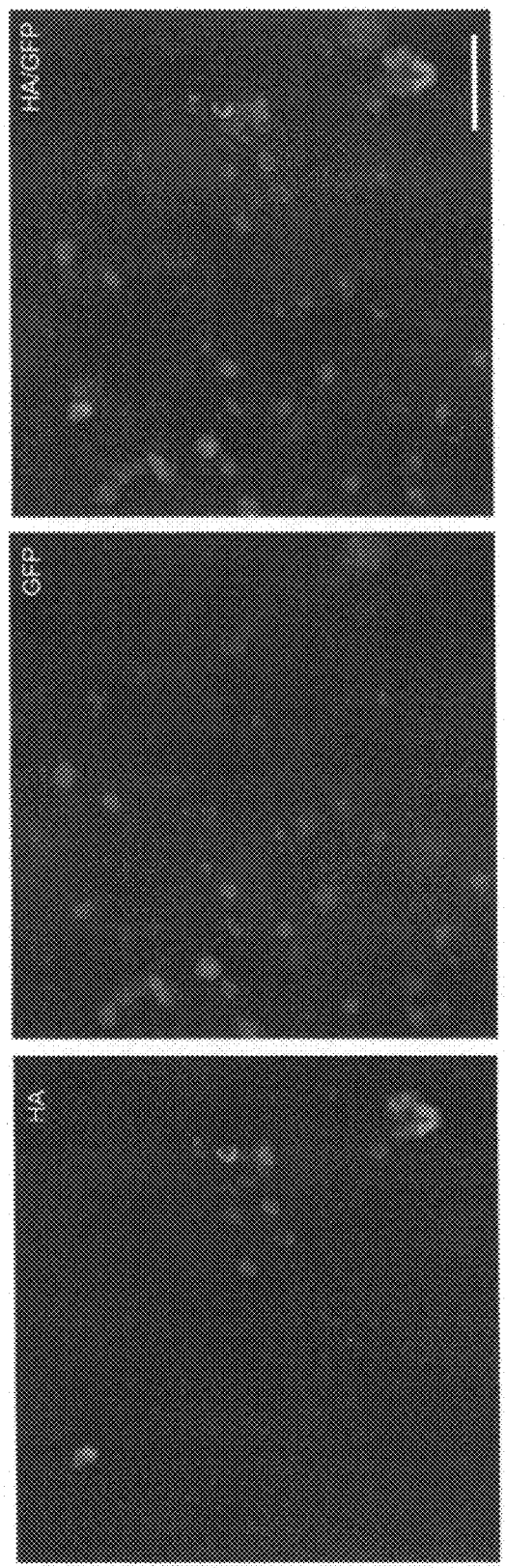

FIG. 11c: Double-staining of HA tag and GFP in hypothalamus of mice 4 months after first surgery (injection of AAV-flax-BDNF) and 3 months after second surgery (injection of AAV-GFPICre). HA (left) and GFP (middle) immunoreactivities were found in the same area of hypothalamus but no colocalization was observed (right). The majority of cells are GFP immunoreactive with fewer cells expressing HA consistent with the −72% knockdown of BDNF protein levels observed in hippocamapal lysates. Scale bar: 50 ttm.

FIG. 12: Table showing the effects of hypothalamic gene transfer of BDNF on various biomarkers in serum.

Figure 13A:
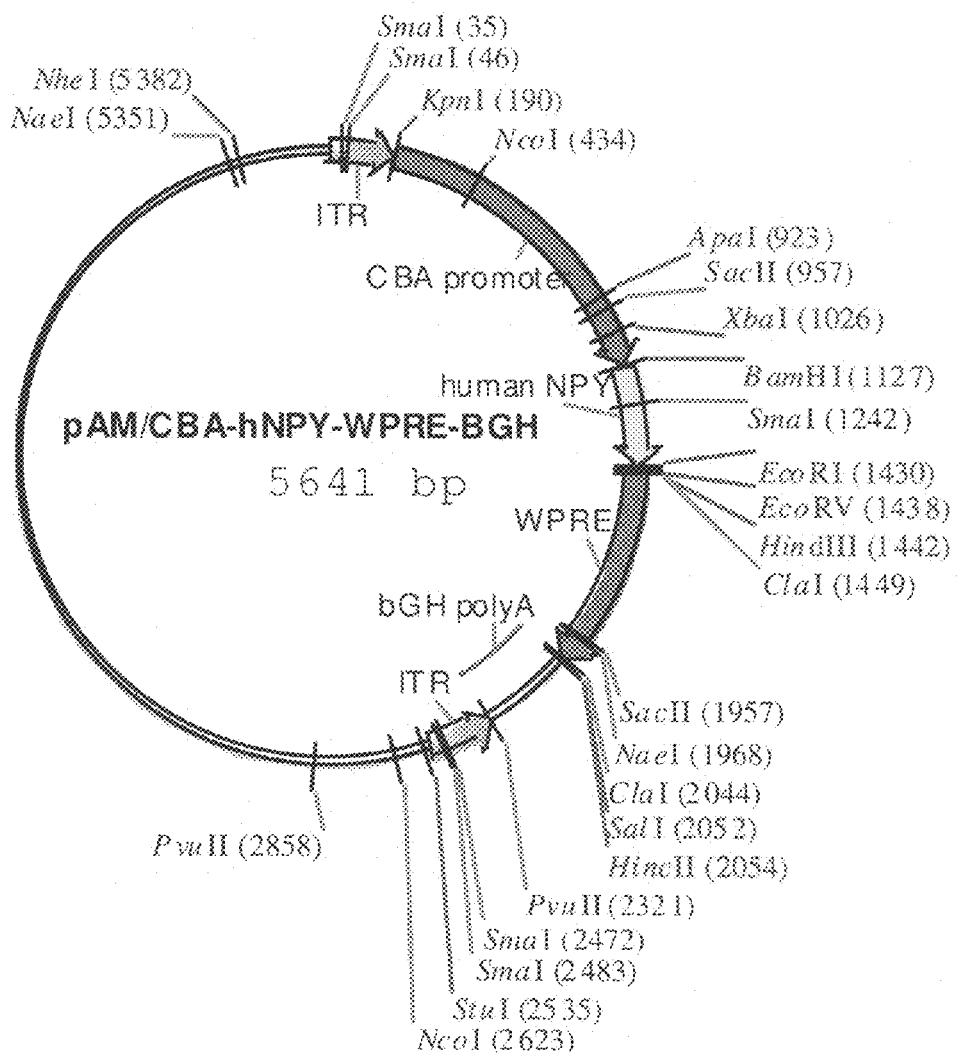

FIG. 13a: pAM/CBA-NPY-WPRE-BGH plasmid map.
FIG. 13b: pAM/CBA-NPY-WPRE-BGH nucleotide sequence [SEQ ID NO:1].
FIG. 13c: CAG-BDNF-HA-WPRE nucleotide sequence [SEQ ID NO:2].

FIG. 14: Two targeting sequences with the highest scores (Invitrogene RNAi Design Tool) were selected and cloned into the Block-iT PolII miR RNAi expression vector: WPRE 74: CTATGTGGACGCTGCTTTA [SEQ ID NO:3], and WPRE155: TCCTGGTTTGTCTCTTTAT [SEQ ID NO:4]. In in vitro experiments, both miR constructs inhibited BDNF expression by at least 90% when co-transfected with the HA-BDNF-WPRE plasmid, as confirmed by ELISA for BDNF. miR-WPRE74 was chosen to construct the autoregulatory plasmid shown.

FIG. 15: The mRNA for human BDNF-nt sequence [SEQ ID NO:5]; aa sequence [SEQ ID NO:10].

FIG. 16: The mRNA for human trkB-nt sequence [SEQ ID NO:6]; aa sequence [SEQ ID NO: 11].

FIG. 17: DNA sequence and gene structure of human AGRP nt sequence [SEQ ID NO:7]; aa sequence [SEQ ID NO: 12].

FIG. 18: DNA sequence for woodchuck post-transcriptional regulatory element (WPRE) [SEQ ID NO:8].

DETAILED DESCRIPTION OF THE PREFERRED EMBODIMENT(S)

In one broad aspect, there is provided herein a recombinant adeno-associated virus (rAAV) virion containing a vector expression cassette having an enhancer and promoter, a regulatory gene sequence and a poly-A flanked by AAV inverted terminal repeats (ITR), and having a biologically active protein cDNA fused at the 5' terminal. It is to be understood that, in certain embodiments, the AAV vector genome can be single stranded containing the ITRs which flank the genome; and in other embodiments, can be double stranded so-called "self-complementary" (sc)AAV which also have ITRs flanking the genome by one ITR which is altered. In one embodiment, there is a deletion in the D-region of one of the ITRs which prevents rep-mediated nicking of the newly synthesized rAAV genome enabling efficient production and packaging of dimeric, double-stranded rAAV genomes into recombinant sc particles. The rAAV virion is inserted to one or more cloning sites between the promoter and the regulatory sequence.

In certain embodiments, the biologically active protein comprises a nucleic acid sequence encoding BDNF, or a derivative or functional fragment thereof, that is expressed in a target cell either constitutively or under regulatable conditions. In a particular embodiment, the biologically active protein comprises a human BDNF protein sequence.

In another broad aspect, there is provided herein a pharmaceutical composition comprising the AAV gene therapy particle in a biocompatible pharmaceutical carrier.

In a particular aspect, the gene transfer comprises stereotactic surgery of AAV-BDNF, a recombinant defective AAV virus to deliver a BDNF cDNA.

In another particular aspect, there is provided herein an inventive method that demonstrates a remarkable efficacy on lowering body weight. Also, there is described herein an inventive method for altering a metabolic profile in a subject in need thereof. In certain embodiments, the altered metabolic profile includes an increase in insulin sensitivity, reduced leptin, and other changes resembling that of an enriched environment.

In another particular aspect, AAV mediated BDNF gene transfer to the hypothalamus leads to an improved metabolic state with weight loss and biochemical markers consistent with markedly improved glucose tolerance and reduced fat mass.

In still another aspect, there is provided herein a hypothalamic BDNF gene therapy that can be useful as a treatment for obesity and related metabolic disorders.

In another broad aspect, there is provided herein a method of gene therapy for the treatment of a subject having a mutation in the BDNF gene comprising, administering a therapeutically effective amount of a recombinant adenoviral associated virus (rAAV) gene therapy particle to cells of the subject, wherein the gene therapy particle. In certain embodiments, the AAV gene therapy vector is administered by a stereotactic route. In a particular embodiment, the cells of the subject are brain hypothalamic cells. In one particular embodiment, the cells of the subject are hypothalamic cells responsible for some or partial control of food intake and/or the body's metabolism (e.g., the body's metabolic rate and/or energy burning). Also, in certain embodiments, the subject is a primate, including, but not limited to, a human.

In still another aspect, there is provided herein a method of reducing or eliminating metabolic-related disorder symptoms comprising administering to a subject in need thereof a therapeutically effective amount of a recombinant adenoviral associated virus (rAAV) gene therapy particle as described herein. In certain embodiments, the metabolic symptoms can be one or more of obesity, insulin sensitivity, syndrome X, and diabetes.

In certain embodiments, the promoter of the transgene is a constitutive promoter. In other embodiments, cellular or hybrid promoters which may also be responsive to the pathophysiological state can be used. It is to be understood that, in certain embodiments, when the target weight is reached, the physiological responsive promoter might be stronger than the promoter driving the transgene.

When the transgene overexpression leads to physiological changes, the weaker promoter controlling interfering RNA expression will be activated and thereby induces RNAi to inhibit the transgene expression. This system can provide a physiological negative feedback for all gene transfer studies and application in vivo and/or in vitro.

In a broad aspect, there is provided herein compositions and methods of a metabolic disorder treatment utilizing transgene expression from a rAAV vector containing a BDNF cDNA. Brain-derived neurotrophic factor (BDNF) is a neurotrophic factor found in the brain and the periphery. BDNF is a protein that acts on certain neurons of the central nervous system and the peripheral nervous system.

As used herein, the term "adeno-associated virus (AAV) vector," "AAV gene therapy vector," and "gene therapy vector" refer to a vector having functional or partly functional ITR sequences and transgenes. As used herein, the term "ITR" refers to inverted terminal repeats (ITR).

Adeno-associated viral vectors (AAV) can be constructed using known techniques to provide at least the operatively linked components of control elements including a transcriptional initiation region, an exogenous nucleic acid molecule, a transcriptional termination region and at least one post-transcriptional regulatory sequence. The control elements are selected to be functional in the targeted cell. The resulting construct which contains the operatively linked components is flanked at the 5' and 3' region with functional AAV ITR sequences.

Throughout this application, various publications are referred to by citations within parentheses and in the bibliographic description, immediately preceding the claims. The disclosures of these publications are hereby incorporated by reference into the present disclosure to more fully describe the state of the art to which this invention pertains, including, but not limited to:

Kaplitt et al., U.S. Pub. No. 2007/0059290 "Transcriptional regulation of target genes;"

During U.S., Pub. No. 2005/0163756 "Oral Delivery of Adeno-Associated Viral Vectors;"

During U.S., Pub. No. 2005/0136,036 "Methods and compositions for the Treatment of Neurological Disease;"

During, U.S. Pub. No. 2004/0131596 "Method and compositions for modifying target receptor function associated with neurological disorders;"

During U.S., Pub. No. 2005/0107320 "Methods and compositions for use in interventional pharmacogenomics;"

Kaplitt et al., U.S. Pub. No. 2003/0087264 "Transcriptional regulation of target genes;"

Kaplitt et al., U.S. Pat. No. 6,503,888 "AAV-mediated delivery of DNA to cells of the nervous system;"

Kaplitt et al., U.S. Pat. No. 6,436,708 "Delivery system for gene therapy to the brain;" and Kaplitt et al., U.S. Pat. No. 6,180,613 "AAV-mediated delivery of DNA to cells of the nervous system."

In another aspect, there is provided herein an AAV gene therapy particle. Further disclosed herein are pharmaceutical compositions and methods for treating, preventing or reducing symptoms of metabolic-related disorders.

As used herein, the terms "gene transfer," "gene delivery," and "gene transduction" can refer to methods or systems for reliably inserting a particular nucleotide sequence (e.g., DNA) into targeted cells. As used herein, the term "gene therapy" can refer to a method of treating a patient wherein polypeptides or nucleic acid sequences are transferred into cells of a patient such that activity and/or the expression of a particular molecule is restored.

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference herein.

Definitions

As used herein, the term "gene" refers to an assembly of nucleotides that encodes a polypeptide and includes cDNA and genomic DNA nucleic acids. A gene is a nucleic acid that does not necessarily correspond to the naturally occurring gene which contains all of the introns and regulatory sequences, e.g., promoters, present in the natural genomic DNA. Rather, a gene encoding a particular protein can minimally contain just the corresponding coding sequence for the protein.

As used herein, a "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

As used herein, transcriptional and translational control sequences are DNA regulatory sequences, such as promoters, enhancers, terminators, and the like, that provide for the expression of a coding sequence in a host cell. In eukaryotic cells, polyadenylation signals are control sequences.

An "expression control sequence" is a DNA sequence that controls and regulates the transcription and translation of another DNA sequence. A coding sequence is "operatively under the control" of transcriptional and translational control sequences in a cell when RNA polymerase transcribes the coding sequence into a precursor RNA, which is then trans-RNA spliced to yield mRNA and translated into the protein encoded by the coding sequence.

A nucleotide sequence is "operatively under the control" of a genetic regulatory sequence when the genetic regulatory sequence controls and/or regulates the transcription of that nucleotide sequence. That genetic regulatory sequence can also be referred to as being "operatively linked" to that nucleotide sequence.

As used herein, a "genetic regulatory sequence" is a nucleic acid that: (a) acts in cis to control and/or regulate the transcription of a nucleotide sequence, and (b) can be acted upon in trans by a regulatory stimulus to promote and/or inhibit the transcription of the nucleotide sequence. Therefore, an inducible promoter is a genetic regulatory sequence. In addition, a portion of a promoter (e.g., fragment/element) that retains and/or possesses the ability to control and/or regulate the transcription of a nucleotide sequence either alone or in conjunction with an alternative promoter or fragment thereof (e.g., a chimeric promoter), is also a genetic regulatory sequence. Such fragments include response elements (genetic response elements) and promoter elements As used herein, an "expression cassette" is a nucleic acid that minimally comprises a nucleotide sequence to be transcribed (e.g., a coding sequence) that is operatively under the control of a genetic regulatory sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

As used herein, a "heterologous gene" is a gene that has been placed into a vector or cell that does not naturally occur in that vector or cell.

As used herein, a gene is an "exogenous gene" when the gene is not encoded by the particular vector or cell.

A "vector" as used herein is a genetic construct that facilitates the efficient transfer of a nucleic acid (e.g., a gene) to a cell. The use of a vector can also facilitate the transcription and/or expression of that nucleic acid in that cell. Non-limiting examples of vectors include plasmids, phages, amplicons, viruses and cosmids, to which another DNA segment may be attached so as to bring about the replication of the attached segment.

The term "subject" as used herein refers to any living organism in which an immune response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

The term "mammal" as used herein refers to a living organism capable of eliciting a humoral immune response to an antigen. The term subject includes, but is not limited to, nonhuman primates such as chimpanzees and other apes and monkey species, sheep, pigs, goats, horses, dogs, cats, mice, rats and guinea pigs, and the like.

Gene Therapy

The genetic regulatory sequences can be used to modulate gene transcription in any cell, including human cells. However, the genetic regulatory sequences can be used to modulate gene transcription in cells of other mammals, such as rodents, e.g., mice, rats, rabbits, hamsters and guinea pigs; farm animals, e.g., sheep, goats, pigs, horses and cows; domestic pets such as cats and dogs, higher primates such as monkeys, and the great apes such as baboons, chimpanzees and gorillas. In certain embodiments, the genetic regulatory sequences can be operatively linked to any heterologous nucleic acid of interest, preferably those encoding proteins.

In addition, the expression cassettes can be constructed to comprise multiple nucleic acids each encoding a different protein and all under the control of the same genetic regulatory sequence. Alternatively, different nucleic acids can be placed under the control of different genetic regulatory sequences. For example, the use of two genetic regulatory sequences, one of which stimulates transcription and the other which hinders transcription under the same conditions, can be used to control the expression of two different genes at the same time by operatively linking one coding sequence to one genetic regulatory sequence and the other coding sequence to the other genetic regulatory sequence. Alternatively, multiple expression cassettes can be employed encoding multiple different proteins. The vectors can be delivered in vitro, ex vivo and in vivo.

When the genetic regulatory sequence is contained in a viral vector, the delivery can be performed by stereotaxic injection into the brain, for example, as previously exemplified (U.S. Pat. No. 6,180,613, herein specifically incorporated by reference in its entirety); or via a guide catheter (U.S. Pat. No. 6,162,796, herein specifically incorporated by reference in its entirety) to an artery to treat the heart. In certain other embodiments, the vectors may also be delivered intravenously, intracerebroventricularly and/or intrathecally, for specific applications. Additional routes of administration can be local application of the vector under direct visualization, e.g., superficial cortical application, or other non-stereotactic applications.

For targeting a vector to a particular type of cell, it may be necessary to associate the vector with a homing agent that binds specifically to a surface receptor of the cell. Thus, the vector may be conjugated to a ligand (e.g., enkephalin) for which certain nervous system cells have receptors, or a surface specific antibody. The conjugation may be covalent, e.g., a crosslinking agent such as glutaraldehyde, or noncovalent, e.g., the binding of an avidinated ligand to a biotinylated vector. In addition, the helper-free defective viral vectors of the present invention can be delivered ex vivo, as exemplified by Anderson et al. (U.S. Pat. No. 5,399,346, herein specifically incorporated by reference in its entirety).

Alternatively, a vector can be introduced by lipofection. Liposomes can be used for encapsulation and transfection of nucleic acids. Synthetic cationic lipids designed to limit the difficulties and dangers encountered with liposome mediated transfection can be used to prepare liposomes for in vivo transfection of a gene encoding a marker (Felgner et al. (1987) Proc. Natl. Acad. Sci. USA 84:7413-7417; see also Mackey et al. (1988), Proc. Natl. Acad. Sci. U.S.A 85:8027-8031). The use of cationic lipids may promote encapsulation of negatively charged nucleic acids, and also promote fusion with negatively charged cell membranes (Felgner et al. (1989) Science 337:387-388). The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as the brain. Lipids may be chemically coupled to other molecules for the purpose of targeting (Mackey et. al. (1988) supra).

In an ex vivo method of the invention, the genetic regulatory sequences are delivered to a host cell to be transplanted into a mammalian recipient. The host cells may be endogenous or exogenous to the mammalian recipient. The term "transplant cell" refers broadly to the component, e.g., tissue or cells, being grafted, implanted, or transplanted into a recipient subject. As used herein, the term "transplantation" refers to the transfer or grafting of tissues or cells from one part of a subject to another part of the same subject or to another subject. Transplanted tissue may comprise a collection of cells of identical composition, or derived from a donor organism, or from an in vitro culture. Delivery of the genetic regulatory sequences of the invention to a transplant cell may be accomplished by any of the methods known to the art and described herein, e.g., as a plasmid, as part of a vector; by injection, lipofection, etc.

Transgenic Animals

A transgenic animal model can be prepared so as to contain a nucleic acid operatively under the control of a genetic regulatory sequence of the present invention. For example, transgenic vectors, including viral vectors, or cosmid clones (or phage clones) can be constructed. Cosmids may be introduced into transgenic mice using published procedures (Jaenisch (1988) Science 240:1468-1474).

Thus, the present invention further provides transgenic, knock-in, and knockout animals that contain one or more heterologous genes operatively under the control of a genetic regulatory sequence of the present invention. These animals can be used as animal models in drug screening assays. In one such example, a drug can be added under various "controlled" expression levels of a particular gene, or at various time points before and/or after induced expression of the particular gene, allowing a much more detailed investigation of the effects of that drug on a particular condition. In a specific embodiment, the transgenic, knock-in, or knockout animal is a mouse. Cells from the inducible knockout, knock-in and/or transgenic animals of the present invention are also part of the present invention.

Transgenic animals can be obtained through gene therapy techniques described above or by microinjection of a nucleic acid, for example, into an embryonic stem cell or an animal zygote (such as a bacterial artificial chromosome (BAC) comprising a nucleic acid operatively under the control of a genetic regulatory sequence of the present invention). Microinjection of BACs has been shown to be successful in a number of animals including rats, rabbits, pigs, goats, sheep, and cows (in Transgenic Animals Generation and Use (1997) ed., L. M. Houdebine, Harwood Academic Publishers, The Netherlands). Methods of constructing BACs or other DNAs such as bacteriophage P1 derived artificial chromosomes (PACs) that encode specific nucleic acids through homologous recombination have recently been described in great detail (Heintz et al. (1998) PCT/US98/12966, herein specifically incorporated by reference in its entirety). Alternatively, a yeast artificial chromosome (YAC) can be used.

Ribozymes and Antisense

Antisense nucleic acids are DNA or RNA molecules that are complementary to at least a portion of a specific mRNA molecule (see Weintraub (1990) Sci. Amer. 262:40-46; Marcus-Sekura (1987) Nucl. Acid Res, 15:5749-5763; Marcus-Sekura (1988) Anal. Biochem. 172:289-295); Brysch et al. (1994) Cell Mol. Neurobiol. 14:557-568). Preferably, the antisense molecule employed is complementary to a substantial portion of the mRNA. In the cell, the antisense molecule hybridizes to that mRNA, forming a double stranded molecule. The cell does not translate an mRNA in this double-stranded form. Therefore, antisense nucleic acids interfere with the expression of mRNA into protein. Preferably a DNA antisense nucleic acid is employed since such an RNA/DNA duplex is a preferred substrate for RNase H. Oligomers of greater than about fifteen nucleotides and molecules that hybridize to the AUG initiation codon will be particularly efficient. Antisense methods have been used to inhibit the expression of many genes in vitro (Marcus-Sekura (1988) supra; Hambor et al. (1988) Proc. Natl. Acad. Sci. U.S.A. 85:4010-4014) and in situ (Arima et al. (1998) Antisense Nucl. Acid Drug Dev. 8:319-327; Hou et al. (1998) Antisense Nucl. Acid Drug Dev. 8:295-308).

Ribozymes are RNA molecules possessing the ability to specifically cleave other single-stranded RNA molecules in a manner somewhat analogous to DNA restriction endonucleases. Ribozymes were discovered from the observation that certain mRNAs have the ability to excise their own introns. By modifying the nucleotide sequence of these ribozymes, researchers have been able to engineer molecules that recognize specific nucleotide sequences in an RNA molecule and cleave it (Cech (1988) JAMA 260:3030-3034; Cech (1989) Biochem. Intl. 18:7-14). Because they are sequence-specific, only mRNAs with particular sequences are inactivated.

Pharmaceuticals

Pharmaceutical compositions may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents, modulators, or drugs (e.g., antibiotics).

In particular embodiments, the pharmaceutical compositions also contain a pharmaceutically acceptable carrier or excipient. Such materials should be non-toxic and should not interfere with the efficacy of the active ingredient. Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences [Mack Pub. Co., 18th Edition, Easton, Pa. (1990)]. The precise nature of the carrier or other material may depend on the route of administration. As described herein, the present invention is directed to administering the expression vectors and compositions thereof of the invention to target cells in the nervous system.

In accordance with the present invention, an expression vector that is to be given to an individual, is administered preferably in a "therapeutically effective amount" or a "prophylactically effective amount" (as the case may be, although prophylaxis may be considered therapy), this being sufficient to show benefit to the individual.

Although the compositions of the invention have been described with respect to human therapeutics, it will be apparent to one skilled in the art that these tools are also useful in animal experimentation directed to developing treatment regimens for animal subjects that have a neurological disorder. Indeed, as described herein, animal subjects which exhibit symptoms characteristic of various 1 disorders have been developed that serve as model systems for such human disorders.

Specific Embodiments

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE I

Methods

Mice. We used male 8-week-old C57BL/6 mice (from Charles River) and male 4-month-old db/db mice (from Jackson Laboratories). All use of animals was approved by and in accordance with the Ohio State University Animal Care and Use Committee.

Recombinant adeno-associated viral vector construction and packaging. The rAAV plasmid contains a vector expression cassette consisting of the cytomegalovirus enhancer, the chicken β-actin (CBA) promoter, the woodchuck post-transcriptional regulatory element (WPRE) and bovine growth hormone polyadenosine flanked by AAV inverted terminal repeats. We fused human BDNF cDNA to the HA tag at the 5' terminus and then inserted it into the multiple cloning sites between the CBA promoter and the WPRE sequence. We cloned the genes encoding EGFP or destabilized YFP into the rAAV plasmid as controls. We packaged and purified rAAV serotype 1 vectors.

Adeno-associated virus-mediated brain-derived neurotrophic factor overexpression in mice kept on standard diet. We randomly assigned 23 C57BL/6 mice, male, 8 weeks of age, to groups receiving rAAV-BDNF (n=13) or rAAV-GFP (n=10). We anesthetized the mice with a single dose of ketamine and xylazine (100 mg kg-1 and 20 mg kg-1, respectively, intraperitoneally) and secured them via ear bars and an incisor bar on a Kopf stereotaxic frame. We made a midline incision through the scalp to reveal the skull and drilled two small holes into the skull with a dental drill above the injection sites (1.2 mm posterior to the bregma, 0.5 mm lateral to the midline, 6.2 mm dorsal to the bregma). We injected rAAV vectors ($3\times10^9$ genomic particles per site) bilaterally into the hypothalamus at a rate of 0.1 μl min-1 with a 10-μl Hamilton syringe attached to a Micro4 Micro Syringe Pump Controller (World Precision Instruments). At the end of infusion, we slowly raised the syringe from the brain and sutured the scalp. We placed the mice back into a clean cage and carefully monitored them after surgery until recovery from anesthesia. We fed mice with normal chow diet (NCD, 11% fat, 28% protein, 61% carbohydrate, caloric density 3.4 kcal g-1, Research Diets).

High-fat diet-induced obesity model. We randomly assigned 24 male C57BL/6 mice, 18 weeks of age, to groups receiving rAAV-BDNF (n=13) or rAAV-YFP (n=11). We injected rAAV vectors (2×109 genomic particles per site) bilaterally into the hypothalamus as described above. We switched the diet to high-fat diet (HFD, 45% fat, caloric density 4.73 kcal g-1, Research Diets) on day 10 after rAAV injection and fed the mice with HFD until the end of the study (72 d after injection).

microRNA vector construction and adeno-associated vector production. We used microRNA to target BDNF. We cloned two targeting sequences in the BDNF coding region into the Block-iT PolII miR RNAi expression vector (pcDNA6.2-Gw/miR, Invitrogen). In in vitro experiments, both miR constructs inhibited BDNF expression when co-transfected with a BDNF expression plasmid, as confirmed by quantitative PCR and ELISA for BDNF (BDNF Emax ImmunoAssay System, Promega). We chose the miR-Bdnf construct with mature microRNA sequence: 5'-AATACTGT-CACACACGCTCAG-3') [SEQ ID NO:9] for in vivo experiments. We subcloned this miR-Bdnf and a scrambled microRNA (miR-scr, with the scrambled sequence targeting no known gene, Invitrogen) into the rAAV plasmid driven by CBA promoter as described herein.

Auto-regulatory system. We amplified two AGRP promoter fragments from human genomic DNA by PCR. FIG. 17 shows the DNA sequence and gene structure of human AGRP [SEQ ID NO:7].

AGRP484 (484 bp, –133 bp to +351 bp from the start of the noncoding exon28) [see SEQ ID NO:8], and AGRP814 (814 bp, –463/+351) [see SEQ ID NO:8].

We inserted the AGRP promoter fragments into rAAV vectors to drive luciferase report gene expression. To verify the induction of AGPR promoter by BDNF-induced physiological change, we injected the combination of viral vectors into the arcuate nucleus of four groups of mice: those expressing YFP and AGRP484-luc, those expressing YFP and AGRP814-luc, those expressing BDNF and AGRP484-luc and those expressing BDNF and AGRP814-luc. We injected an equal amount of each viral vector ($1.5\times10^9$ genomic titer) bilaterally. We killed the mice and dissected the hypothalamus 3 weeks after rAAV injection. We measured the luciferase activity in the hypothalamic lysate by Bright-Glo Luciferase Assay (Promega) and calibrated the luminescence to the protein concentration. We chose AGRP484 to develop the autoregulatory system. We generated vectors containing two cassettes, one cassette expressing BDNF driven by the CBA promoter as described above and the other cassette expressing microRNA (miR-Bdnf or miR-scr) driven by AGRP484. Both the transgene and the microRNA cassettes were packaged to a single viral vector (BDNF-miR-scr, BDNF-miR-Bdnf).

db/db mice. We randomly assigned 30 db/db mice to groups receiving rAAV-YFP, rAAV-BDNF-miR-scr or rAAV-BDNF-miR-Bdnf, with ten mice per group. We injected rAAV vectors ($3.4\times10^{10}$ genomic particles per site) bilaterally into the hypothalamus as described above. We fed the db/db mice with NCD throughout the experiment. We killed the mice receiving rAAV-BDNF-miR-scr one month after injection owing to their severe weight loss. We recorded the body weight and food consumptions periodically until the end of the experiment (79 d after injection).

Knockdown of transgene expression by Cre-loxP recombination. We generated the DIO model by feeding mice with HFD for 10 weeks until the body weight reached 40 g. We randomly assigned the obese mice to groups receiving rAAV flox-BDNF or rAAV-YFP. We injected rAAV vectors bilaterally to the hypothalamus as described above ($1.0\times10^{10}$ genomic particles per site). We monitored body weight every 5-7 d and recorded the food intake. One month after first surgery, we split the flox-BDNF-expressing mice into two groups receiving rAAV-GFP-Cre or empty rAAV as a control. We injected all YFP-expressing mice with rAAV-GFP-Cre.

We performed the second surgery with the same procedure as the first surgery. We kept the mice on HFD until the end of the study (4 months after the first surgery).

Statistical analyses. Values are expressed as means±s.e.m. For body weight, insulin tolerance and glucose tolerance, we determined the overall significance by one-way repeated measure analysis of variance. We used one-way analysis of variance to analyze serum biomarker measurements, liver weight and adipose tissue weight. We used multivariate analysis of variance to analyze quantitative RT-PCR data.

Body weight and food consumption. We maintained the mice on a normal 12 h/12 h light/dark cycle with respective diet (NCD or HFD) and water ad libitum throughout the experiment. Body weight of each individual mouse was recorded before injection and every 3-7 days after injection. Food consumption was recorded periodically after injection as the total food consumption of each cage housing 4-5 mice and represented as the average of food consumption per mouse per day.

Serum harvest and biomarker measurement. We collected blood from the retroorbital sinus 3-4 weeks after AAV injection. We anesthetized the mice of each group at the same time with ketamine (87 mg kg-1)/xylazine (13 mg kg-1) followed by blood withdraw. All blood harvesting started at 10:00 am. We prepared serum by allowing the blood to clot for 30 min on ice followed by centrifugation. Serum was at least diluted 1:5 in serum assay diluent and assayed using the following DuoSet ELISA Development System (R&D Systems): mouse IGF-1, IGFBP-3, Leptin, Leptin R, Adiponectin/Acrp30. Insulin was measured using Mercodia ultrasensitive mouse insulin ELISA (ALPCO Diagnostic). Glucose was measured using QuantiChrom Glucose Assay (BioAssay Systems). Total cholesterol was measured using Cholesterol E test kit (Wako Diagnostics). Triglyceride was measured using L-Type test (Wako Diagnostics).

BDNF expression quantification. We dissected hypothalami and prepared total RNA from half of the hypothalamic tissue and subjected it to quantitative RT-PCR. We calibrated the data of quantitative RT-PCR to the endogenous control gene Eef2. We prepared lysates from the other half of the hypothalamic tissue and measured BDNF protein level using ELISA (BDNF Emax ImmunoAssay System, Promega). The BDNF protein level was calibrated to the total protein level.

Red-O staining. We stained lipids in liver and white adipose tissue frozen sections using an Oil Red-O solution (Sigma).

Glucose tolerance test. We injected mice intraperitoneally with glucose solution (1 mg glucose per kg body weight) after an overnight fast. We obtained blood from the tail at various time points. We measured blood glucose concentrations with a portable glucose meter (ReliOn Ultima).

Insulin tolerance test. We injected mice intraperitoneally with insulin (0.75 unit per kg body weight) at 2 pm without a fast. We obtained blood from the tail and measured the blood glucose concentration as described herein.

Quantitative RT-PCR. We dissected liver, white adipose tissue and hypothalamus and isolated total RNA using RNeasy Mini Kit plus RNase-free DNase treatment (Qiagen). We generated first-strand cDNA using TaqMan Reverse Transcription Reagent (Applied Biosystems) and carried out quantitative PCR using an ABI PRISM 7000 Sequence Detection System with the Power SYBR Green PCR Master Mix (Applied Biosystems). We designed primers to detect the following mouse mRNA: Bdnf, Npy, Agrp, Sgk1, Vgf, Insr, Lepr, Ntrk2, Cartpt, Pomc, Mc4r, Trh, Crh, Ucp1, Ucp2, Ucp3, Lep, Adipoq, Cycs, Fasn, Ppargc1a, Rb1, Pparg, Dio2, Acox1, Cpt1a, Gpam, Scd1, Srebf1. Primer sequences are available on request. We calibrated data to endogenous control Actb in liver and adipose tissue, Eef2 in hypothalamus and quantified the relative gene expression using the equation $T0/R0 = K \times 2^{(CT,R - CT,T)}$. T0 is the initial number of target gene mRNA copies, R0 is the initial number of internal control gene mRNA copies, CT,T is the threshold cycle of the target gene, CT,R is the threshold cycle of the internal control gene and K is a constant.

rAAV-microRNA experiment. We randomly assigned 7 week old C57/BL6 mice to receive AAV-CBA-miR-Bdnf (n=10) or AAV-CBA-miR-scr (n=10). We injected 0.7 μl of AAV vectors ($1.4 \times 10^{10}$ particles) bilaterally into the hypothalamus at the stereotaxic coordinates described above. We sacrificed the mice 30 days after vector injection and dissected the hypothalamus for Q-PCR and BDNF ELISA.

Immunohistochemistry. We perfused mice with 20 ml cold PBS followed by 50 ml 4% paraformaldehyde. Coronal brain sections (20 μm) were cut using a Leica freezing microtome and immunofluorescence staining was performed with the following antibodies: monoclonal antibody to HA tag (Covance, 1:250) followed by Cy3conjugated secondary antibody (Jackson Immunoresearch, 1:400); polyclonal antibody to NPY (Chemicon, 1:8,000) followed by DyLight488-conjugated secondary antibody (Jackson Immunoresearch, 1:600); polyclonal antibody to GFAP (Dako, 1:500) followed by Cy3-conjugated secondary antibody (Jackson Immunoresearch, 1:400). Apoptosis was assessed by TUNEL assay using in situ Cell Death Detection Kit (Fluorescence, Roche) according to manufacturer's instruction and counterstained with DAPI. We detected immunofluorescence with Zeiss Axioskop40 microscope and took pictures and processed the pictures with Zeiss AxioVision3.1 software. We processed confocal laser scanning with Zeiss 510 Meta Laser Scanning Confocal microscope.

Open field. To assess exploration and general motor activity, we placed mice individually into the center of an open square arena (60 cm×60 cm, enclosed by walls of 48 cm). The mouse was allowed 10 min in the arena, during which time its activity was recorded and analyzed by Clever Systems TopScan Software (Clever Sys Inc, Vienna, Va.). Specifically, we measured the distance traveled both in the center of the arena (36 cm×36 cm), the total distance traveled and the time spent in the center of the arena. The total distance traveled provides a measure of exploratory activity while the time and distance ratio of arena center exploration provides a preliminary indication of anxiety level. We cleaned the arena with 30% ethanol between trials to remove any odor cues.

Flox-BDNF vector. We generated flox-BDNF plasmid by inserting two lox P flanking the human BDNF-HA cDNA in the AAV vector. We packaged the following rAAV1 viral vectors: flox-BDNF, Cre recombinase fused to GFP, and empty vectors as control.

Metabolic studies. We measured energy expenditure and activity of mice using the Oxymax Lab Animal Monitoring System (Columbus Instruments). Individual mice were allowed to be habituated to the instrument overnight and the physiological and behavioral parameters were monitored for 24 h (activity, food and water consumption, metabolic performance and temperature). Oxygen consumption, carbon dioxide production and methane production were normalized to the body weight and corrected to an effective mass value according to the manufacturer's software.

Bone mineral density. We measured the volumetric bone mineral density (vBMD) by microcomputed tomography (μCT, Siemens Invion, Wright Center for Innovation, The Ohio State University).

Results for Example I

Hypothalamic Gene Transfer of Bdnf in Normal Mice Fed a NCD

Figure 1A:
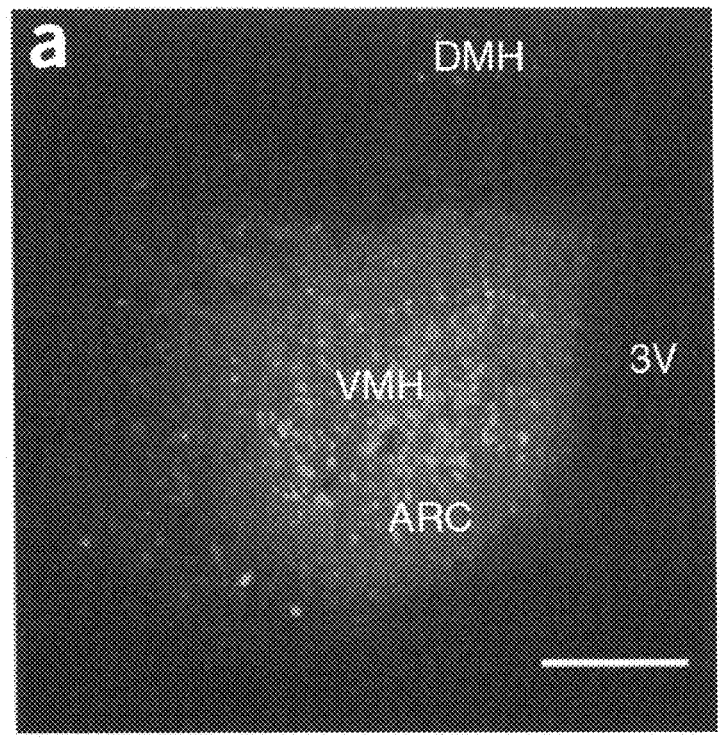
FIGS. 1a-1f: Hypothalamic gene delivery of BDNF leads to weight loss, changes in serum biomarkers and hypothalamic gene expression in wild-type mice fed with NCD.
Figure 1B:
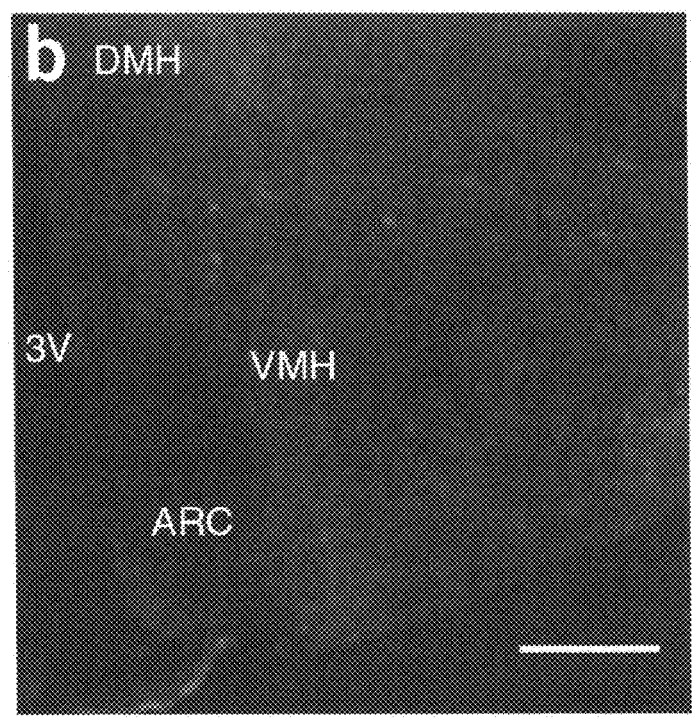
Figure 1C:
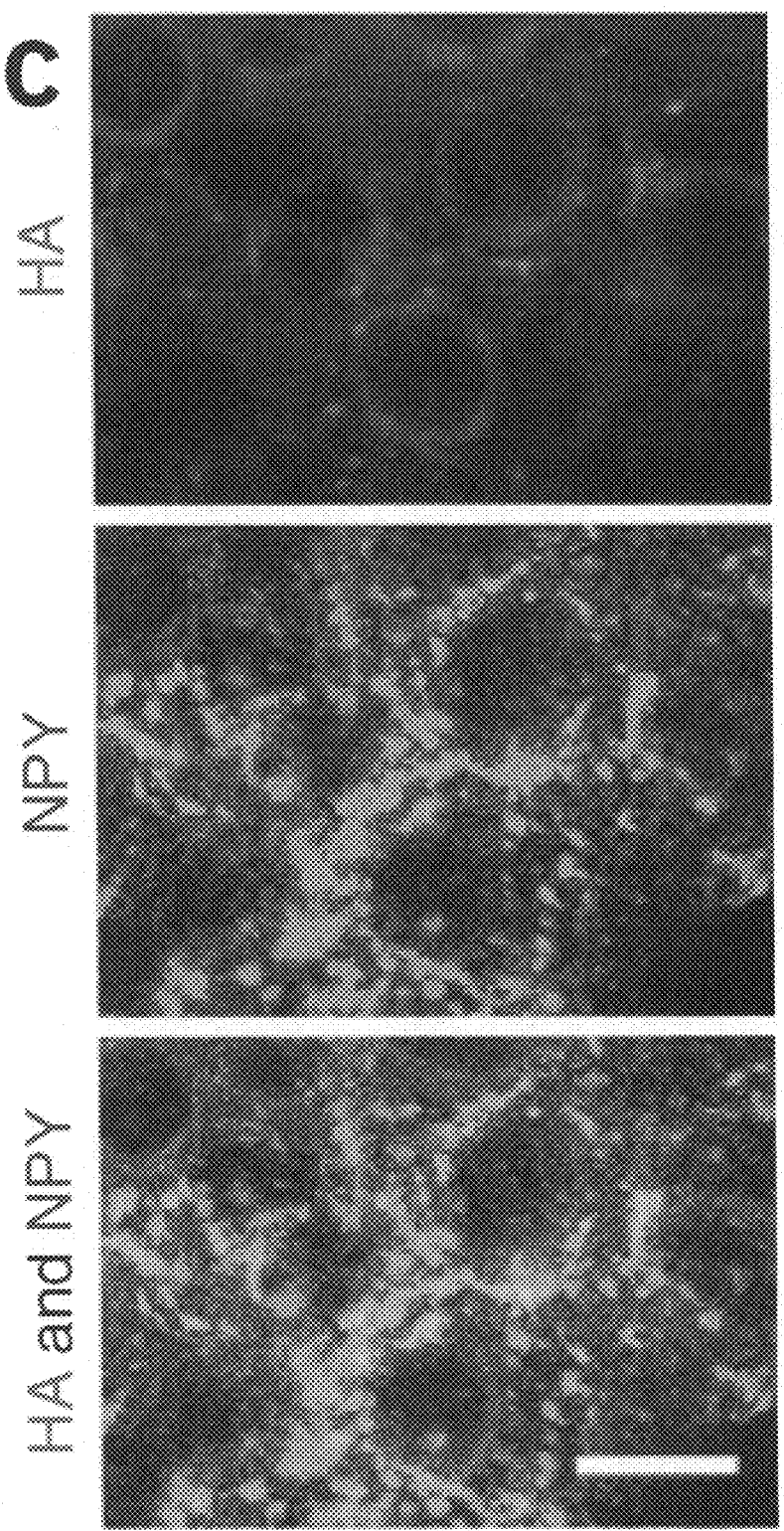
Figure 1D:
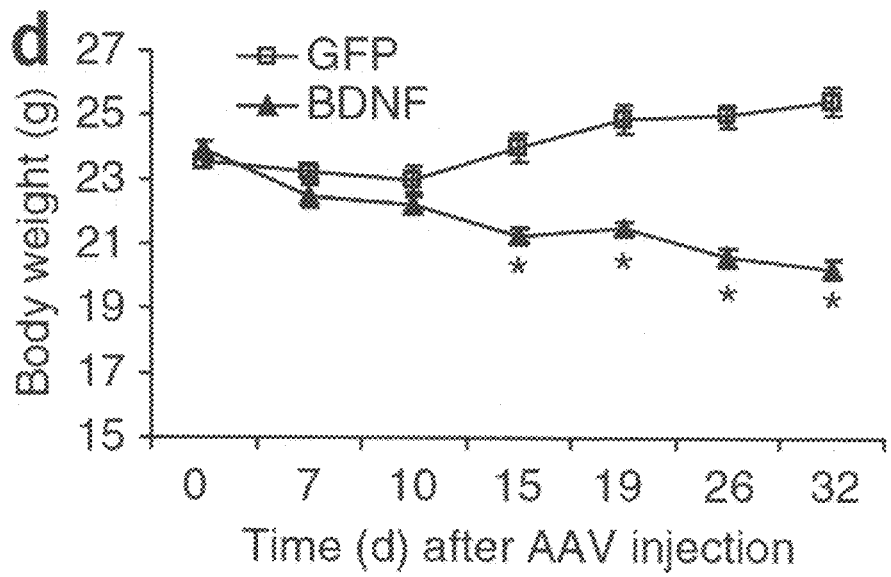
Figure 1E:
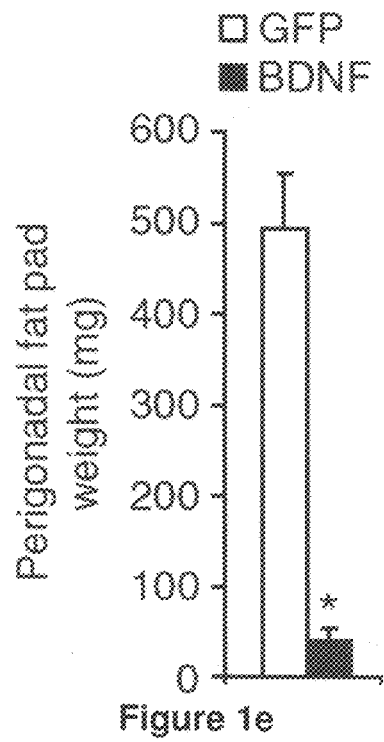
Figure 6A:
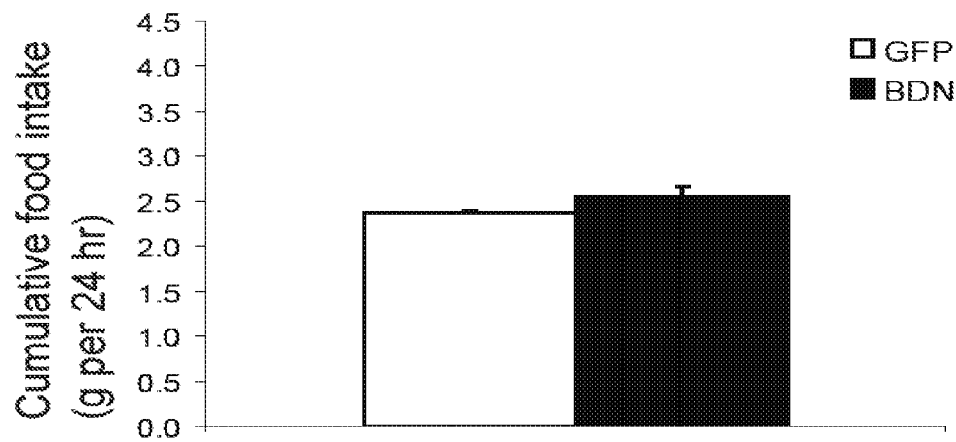
FIGS. 6a-6c: Food intake was not changed by hypothalamic gene transfer of BDNF in mice fed on standard diet (FIG. 6a) or high fat diet (FIG. 6b).

We delivered hemagglutinin (HA)-tagged human BDNF to the hypothalamus bilaterally via rAAV, using GFP as a control. In a subset of mice, we determined gene transfer efficacy by HA immunofluorescence and GFP fluorescence for the respective vectors, with expression observed in the arcuate nucleus and ventromedial hypothalamus (FIGS. 1a,b). Consistent with the use of a constitutive promoter, we observed expression in the majority of neurons in the targeted region, including in arcuate agouti-related protein (AgRP) and neuropeptide Y (NPY) coexpressing neurons (FIG. 1c). We observed an initial surgery-associated weight loss in both groups, but GFP-expressing mice quickly recovered and then regained weight on their presurgery trajectory (FIG. 1d). In contrast, BDNF-expressing mice continued to lose weight throughout the course of the experiment (FIG. 1d). By one month after injection, the weight of BDNF-expressing mice had decreased by 3.66±0.27 g, whereas the weight of GFP-expressing mice had increased by 1.91±0.37 g. There was no significant change in food consumption (FIG. 6a). Adiposity was greatly reduced in BDNF-expressing mice, as indicated by a 92% reduction in the weight of the perigonadal fat pad at 50 d after injection (FIG. 1e).

BDNF expression led to a sharp decrease in leptin abundance (12.2%±2.6% of GFP-expressing mice, $P<0.001$) and insulin (18.0%±2.3% of GFP, $P<0.001$). Both leptin and insulin concentrations are known to correlate with fat mass. Moreover, expression of adiponectin, a major adipokine with a role in regulating insulin sensitivity and inhibiting appetite, was markedly increased in BDNF-expressing mice, whereas cholesterol, triglyceride and insulin-like growth factor-1 concentrations were all reduced (FIG. 12).

Figure 1F:
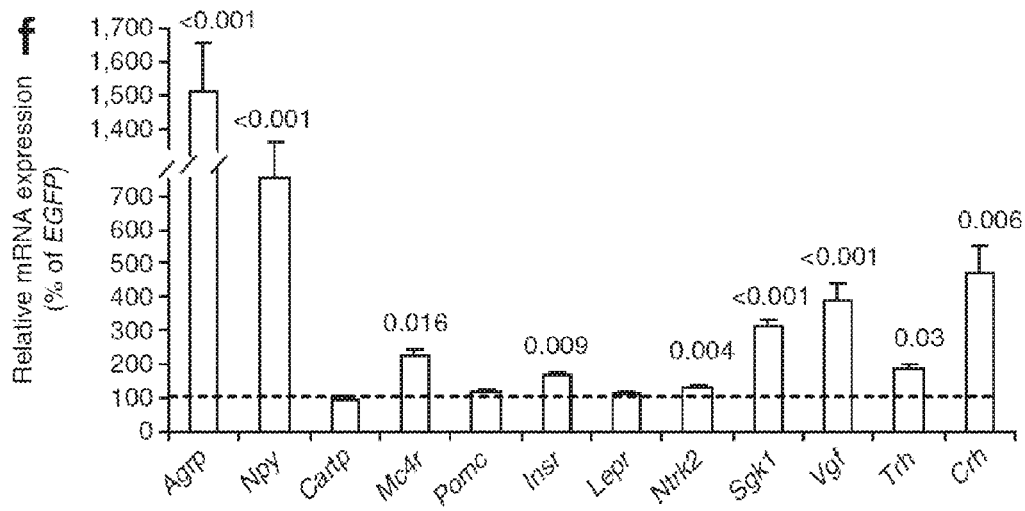

We used real-time quantitative PCR to examine hypothalamic expression of genes involved in energy homeostasis. Agrp and Npy, which encode two orexigenic peptide hormones, were upregulated 15.11±1.44-fold and 7.55±1.04-fold in BDNF-expressing, compared to GFP-expressing, mice, respectively (FIG. 1f), consistent with a compensatory response to the weight loss and fat depletion. Mc4r (encoding melanocortin-4 receptor), proposed to be upstream of both BDNF and a major pathway shared by leptin, insulin and other anorexic signals, was upregulated significantly, whereas expression levels of the additional anorexigenic molecules Cartpt (encoding CART prepropeptide) and Pomc (encoding proopiomelanocortin) were not changed (FIG. 1f). Expression of the BDNF receptor Ntrk2 was increased, indicating positive feedback (FIG. 1f). Insulin receptor (Insr) expression was also upregulated, whereas expression of the leptin receptor long form (Lepr) was not changed (FIG. 1f). Expression of Trh (encoding thyrotropin-releasing hormone) and Crh (encoding corticotropin-releasing hormone) was increased in BDNF-expressing mice (FIG. 1f).

BDNF Gene Transfer Prevents Diet Induce Obesity (DIO)

Figure 2A:
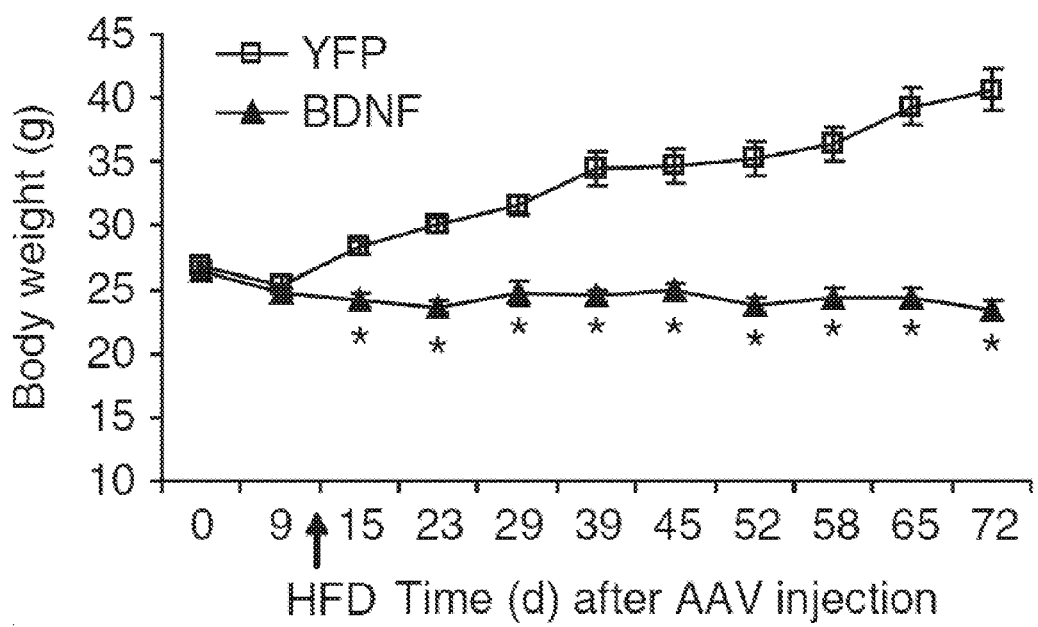
FIGS. 2a-2h: Hypothalamic gene delivery of BDNF prevents DIO in wild-type mice.

Chronic consumption of a HFD contributes to obesity in experimental animals and humans. We used C57BL/6 mice, a strain prone to DIO, to assess the therapeutic efficacy of hypothalamic BDNF gene transfer. Given the potency of the rAAV-BDNF vector observed in normal mice, we decreased the dose (from $3\times10^9$ genomic titer per site to $2\times10^9$ genomic titer per site) and used older (18 weeks) mice. We also used a destabilized yellow fluorescent protein (YFP) as our control, as GFP has been associated with nonspecific toxic effects. Ten days after surgery, we switched the mice to a 45% HFD. The weight gain of YFP-expressing mice, which acted as our control treatment group, accelerated, whereas BDNF-expressing mice maintained a stable weight (FIG. 2a).

Figure 2B:
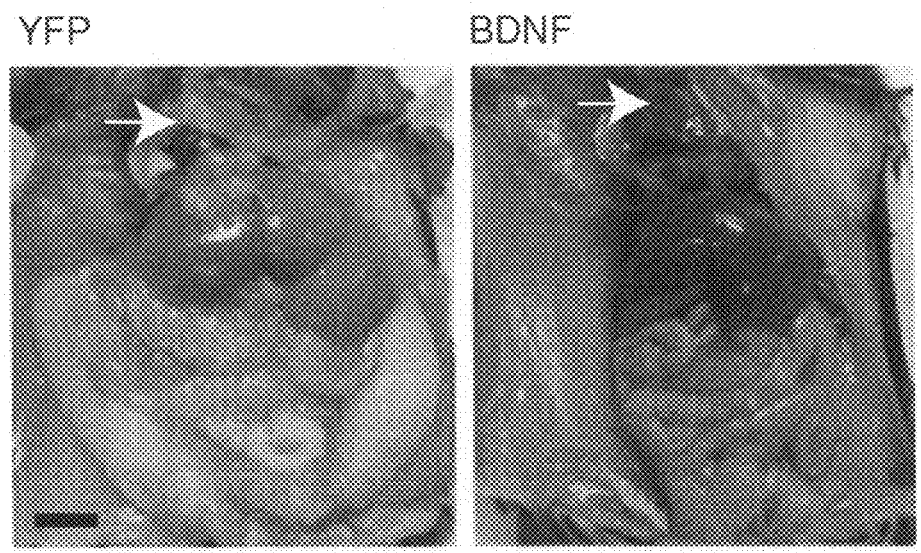
Figure 2C:
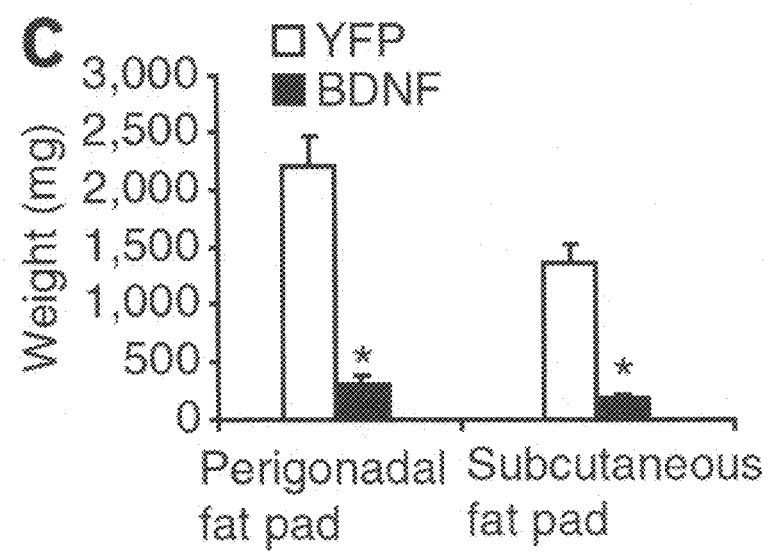
Figure 2D:
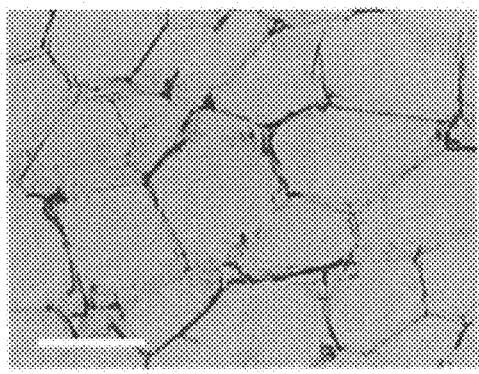
Figure 2D:
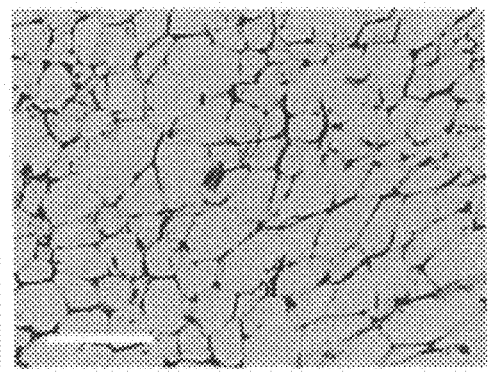
Figure 2E:
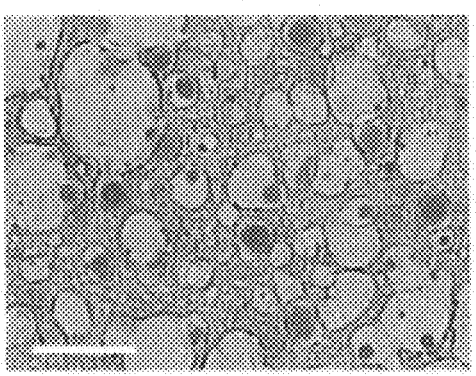
Figure 2E:
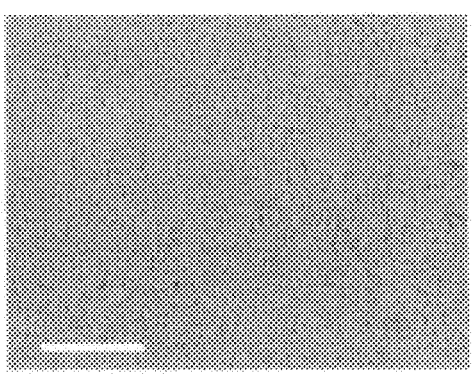
Figure 2F:
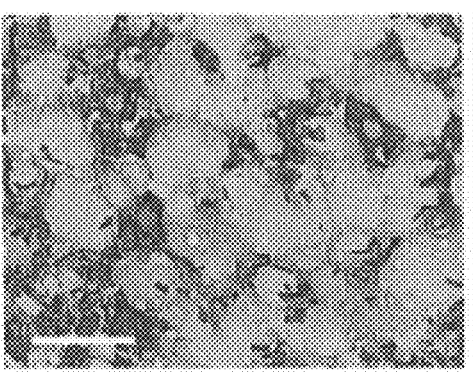
Figure 2F:
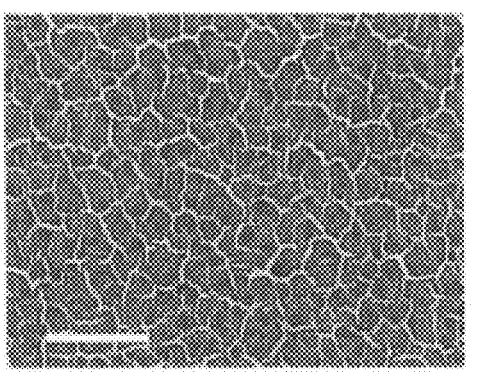
Figure 2G:
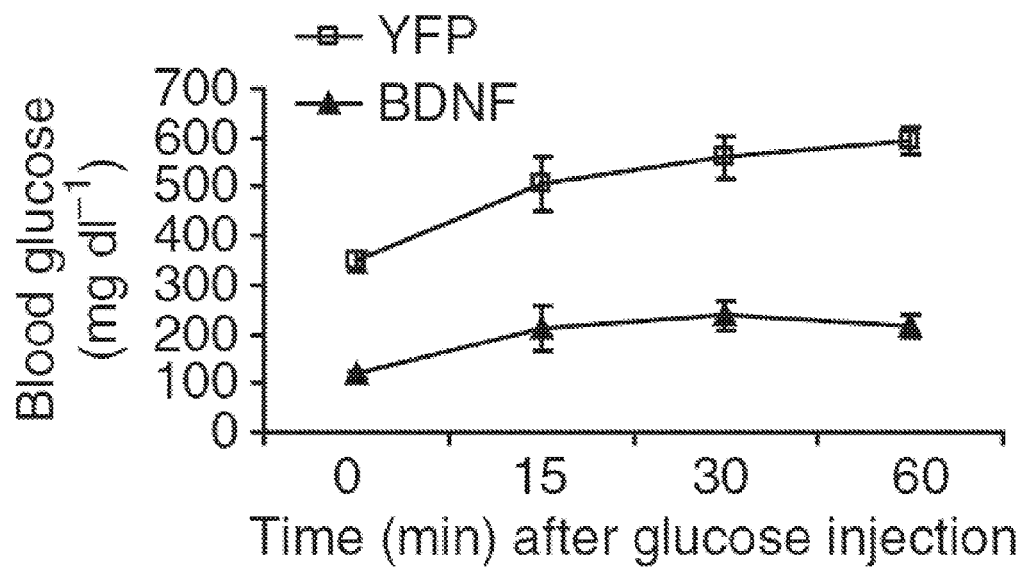
Figure 2H:
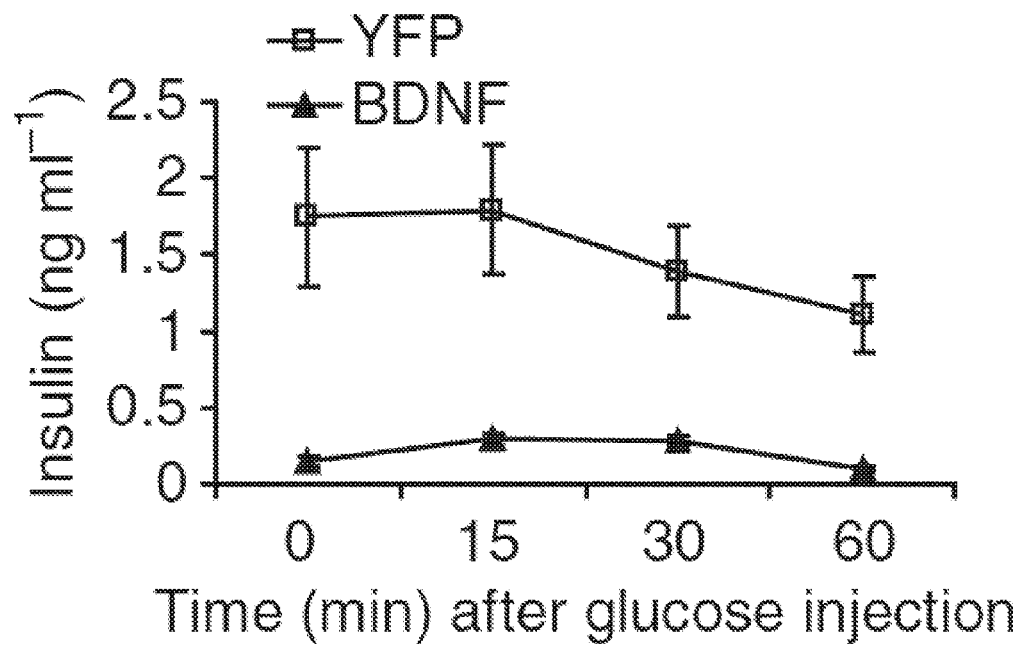
Figure 6B:
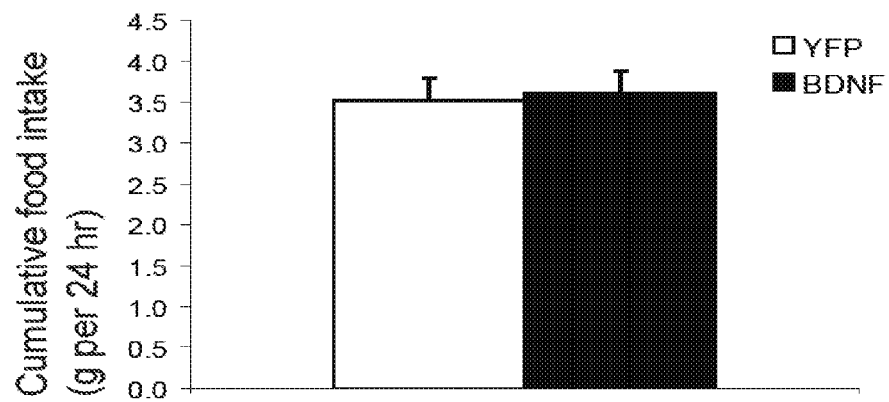

By 72 d after surgery, YFP-expressing mice had gained 13.78±1.88 g on the HFD, whereas BDNF-expressing mice lost 2.80±0.71 g with no change in food consumption (FIG. 6b). YFP-expressing mice developed abdominal obesity with the weight of perigonadal fat pads increased by 4.5-fold compared to NCD controls (data not shown). In contrast, the perigonadal pad weight of BDNF-expressing mice was only 14.2±3.1% that of the YFP-expressing mice. The weight of subcutaneous fat was also greatly less (FIGS. 2b, 2c), and the pericardial fat observed in YFP-expressing mice was completely absent in the BDNF-expressing mice (FIG. 2b). Moreover, H&E staining revealed an 85.7±1.1% smaller adipocyte size in BDNF-expressing mice (FIG. 2d).

DIO was associated with hyperinsulinemia, hyperleptinemia, hyperglycemia and dyslipidemia, with BDNF completely preventing this metabolic profile (FIG. 12). The lower circulating leptin concentrations were not solely due to the smaller fat mass. When leptin concentrations were standardized to the perigonadal fat pad weight, BDNF-expressing mice still showed a significant decrease (YFP-expressing mice, 7.347±0.612 pg ml-1 g-1; BDNF-expressing mice, 3.735±0.798 pg ml-1 g-1; P=0.003).

Figure 6C:
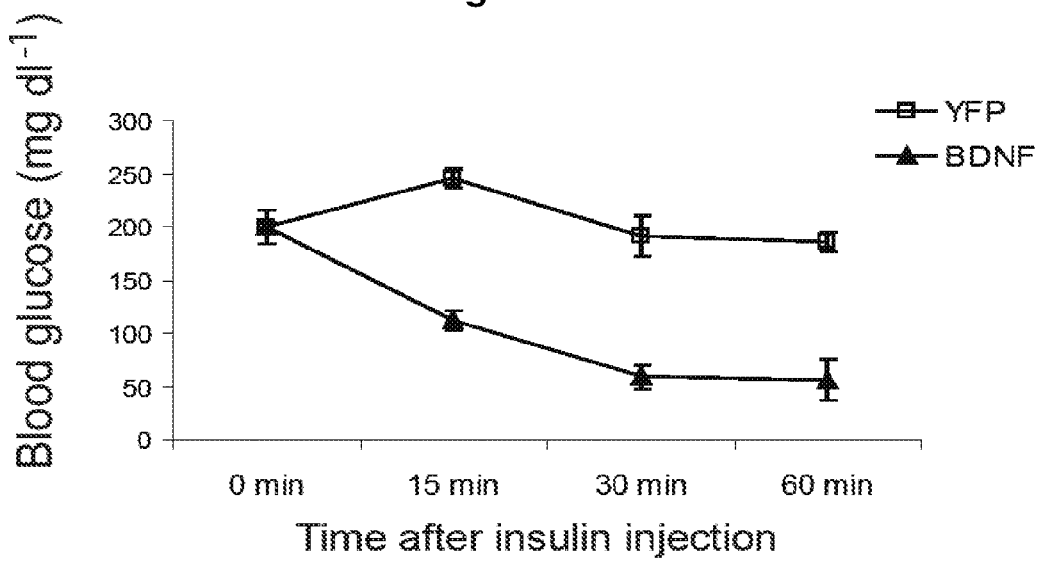

In contrast, adiponectin showed a greater than 14-fold higher level when its concentration was corrected to fat mass (YFP-expressing mice, 1.624±0.314 ng ml-1 g-1; BDNF-expressing mice, 24.030±5.540 ng ml-1 g-1; P=0.005), indicating that BDNF expression influenced adipocyte autonomous leptin and adiponectin secretion. In addition, the insulin insensitivity and glucose intolerance observed in YFP-expressing obese mice were greatly improved in BDNF-expressing mice (FIG. 2 and FIG. 6c).

HFD feeding led to liver steatosis in obese YFP-expressing mice, as characterized by pale macroscopic enlargement (FIG. 2b) and excessive fat accumulation observed in oil red O-stained (FIG. 2e) and H&E-stained (FIG. 2f) sections. BDNF expression prevented the liver steatosis (FIGS. 2e, 2f), with the liver weight being 45% that of the YFP-expressing mice (BDNF-expressing mice, 1.18±0.05 g; YFP-expressing mice, 2.61±0.29 g; P=0.001).

Figure 3A:
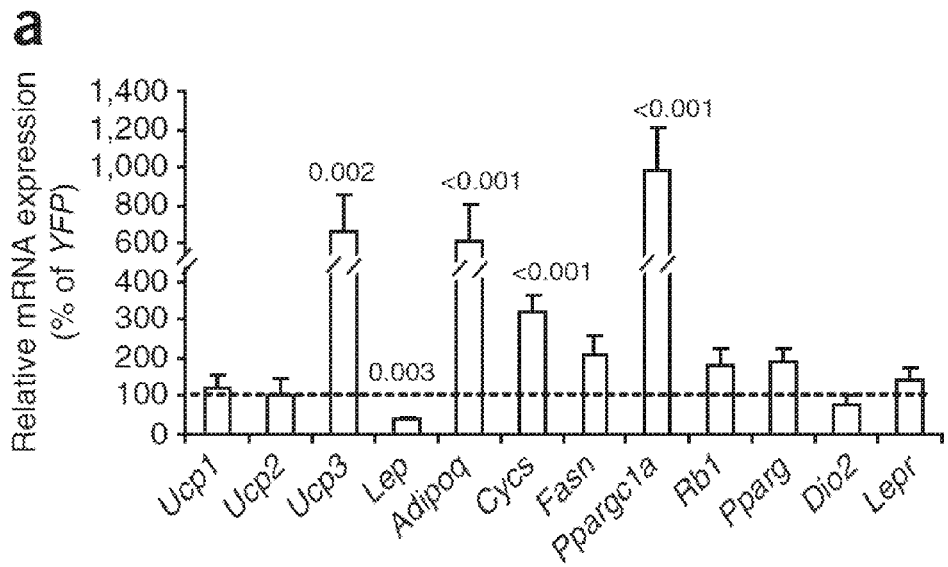
FIGS. 3a-3c: Gene expression profiles of HFD-fed mice. Relative mRNA expression levels of the indicated genes in WAT (FIG. 3a), liver (FIG. 3b) and hypothalamus (FIG. 3c (n=6 per group). Bars show the relative expression in BDNF-expressing mice as compared to YFP-expressing mice. P values are shown over the bars. Srebf1, sterol regulatory element-binding transcription factor-1; Rb1, retinoblastoma-1; Dio2, deiodinase, iodothyronine, type II.

We profiled the expression of genes involved in lipid metabolism and mitochondrial activity in both white adipose tissue (WAT, FIG. 3a) and brown adipose tissue (data not shown). In WAT, Ppargc1a, encoding a cofactor controlling mitochondrial biogenesis, was upregulated 9.8±2.2-fold in BDNF-expressing mice, whereas the expression of cytochrome c (Cycs) was increased 3.2±0.5-fold compared to the obese control mice. Uncoupling proteins (UCP) are a family of proteins involved in the regulation of lipid oxidation, as well as the regulation of energy expenditure. The expression of Ucp3 was increased 6.8±1.9-fold in WAT from mice expressing BDNF, suggesting a possible increase in energy expenditure of WAT. Moreover, Lep (encoding leptin) expression was decreased by 62.0%±7.9%, whereas Adipoq (encoding adiponectin) expression was increased by 6.1±1.9-fold, consistent with the observed weight loss. Lep expression was also decreased by 68.5%±14.3% in BDNF brown adipose tissue whereas no other genes screened were significantly changed.

Figure 3B:
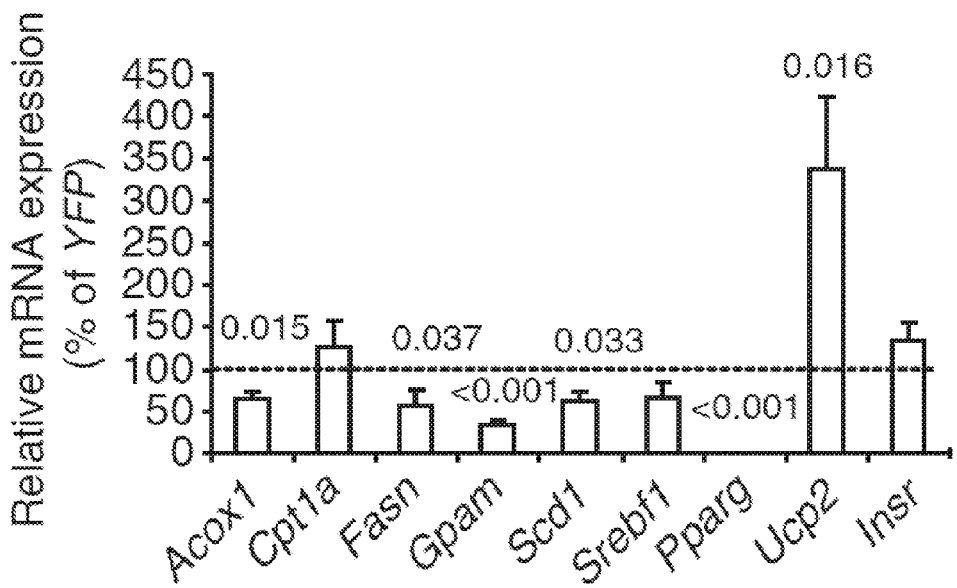

BDNF treatment significantly suppressed lipogenic gene expression in liver, decreasing Fasn (encoding fatty acid synthase) expression by 43.1%±17.5%, Gpam (encoding mitochondrial glycerol-3-phosphate acyltransferase) by 66.4%±4.2% and Scd1 (encoding stearoyl-CoA desaturase) by 37.8%±10.9%. Its effects on lipolytic genes were less marked, with a decrease in Acox1 (encoding acyl-coenzyme A oxidase-1, palmitoyl) expression but no change in Cpt1a (encoding carnitine palmitoyltransferase 1A) expression, although both are involved in fatty acid oxidation (FIG. 3b).

Figure 3C:
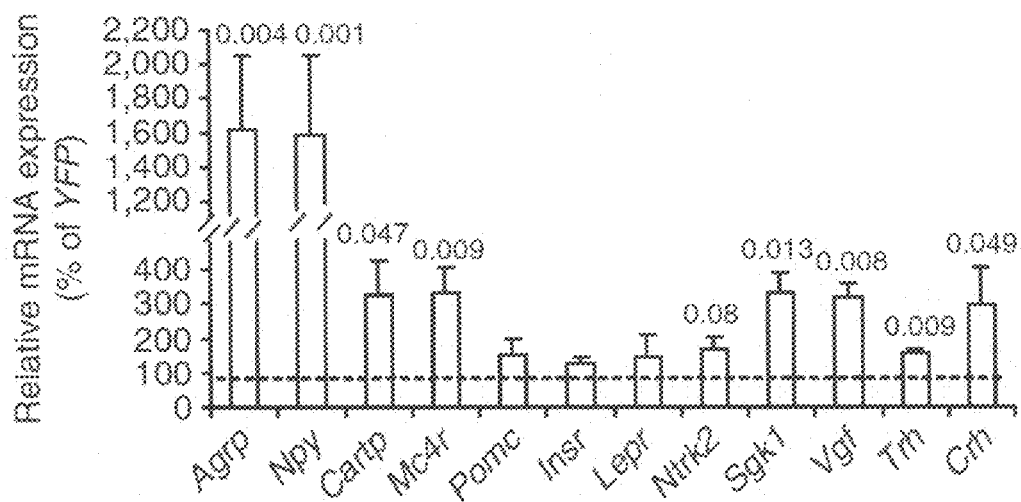

Expression of Pparg, an adipocyte-specific peroxisome proliferator-activated receptor isoform and a type 2 diabetes marker, was decreased by 99.6%±0.1% in the liver of BDNF-treated mice, consistent with the absence of fatty infiltration. Expression of Ucp2, a mitochondrial inner-membrane protein that uncouples ATP synthesis and negatively regulates reactive oxygen species production, was significantly upregulated by 3.39±0.86-fold in the liver of BDNF-treated mice, which may serve a protective role when hepatocytes are exposed to metabolic stress such as high-fat feeding. We also profiled hypothalamic gene expression in BDNF-expressing mice on a HFD and observed a similar pattern of changes as BDNF-expressing mice fed with a NCD except that Cartpt was upregulated approximately threefold in the HFD condition (FIG. 11 versus FIG. 3c).

Transgene expression in the hypothalamus was maintained throughout the duration of the experiment, with BDNF concentrations of 5541.4±738.4 pg mg-1 in BDNF-expressing mice compared to 87.6±11.2 pg mg-1 in YFP-expressing mice, P<0.001. Moreover, histological examination of hypothalamic sections showed a lack of cytotoxicity with no cell loss (as determined by Nissl staining, FIG. 7a), no gliosis (as determined by glial fibrillary acidic protein staining, FIG. 7b) and no apoptosis (TUNEL assay, FIG. 7d).

An Autoregulatory BDNF Vector in Diabetic Db/Db Mice

Gene therapy dose titration in humans is difficult, particularly in a clinical setting where diet is not tightly controlled. We, therefore, aimed to improve the safety of the approach and develop a vector that could be considered for clinical translation by tightly coupling transgene expression to the physiological changes induced by the expression of the introduced therapeutic gene. Of the hypothalamic genes profiled in BDNF-expressing mice, Agrp was the most robustly upregulated, with 15.1-fold and 16.2-fold increases in expression in mice on NCD and HFD, respectively, (FIG. 11 and FIG. 3c) consistent with the observed weight loss and particularly the decrease in body fat mass.

We amplified two human AGRP promoter fragments of different lengths, each containing the hypothalamus-specific exon. We coupled the AGRP promoter fragments to a luciferase reporter gene and packaged these cassettes into rAAV vectors. We injected these AGRP promoter-driven luciferase vectors into the hypothalamus together with the BDNF vector to induce weight loss and compared luciferase activity with YFP controls.

The 484-base pair (bp) fragment promoter (termed AGRP484) showed better inducibility than the 814-bp fragment. The induction of AGRP484 was 2.66±0.57-fold, whereas the induction of AGRP814 was 1.32±0.38-fold (n=6 each group), analyzed when BDNF-expressing mice had lost 1.5±0.22 g of weight and YFP mice gained 1.5±0.56 g.

Figure 4A:
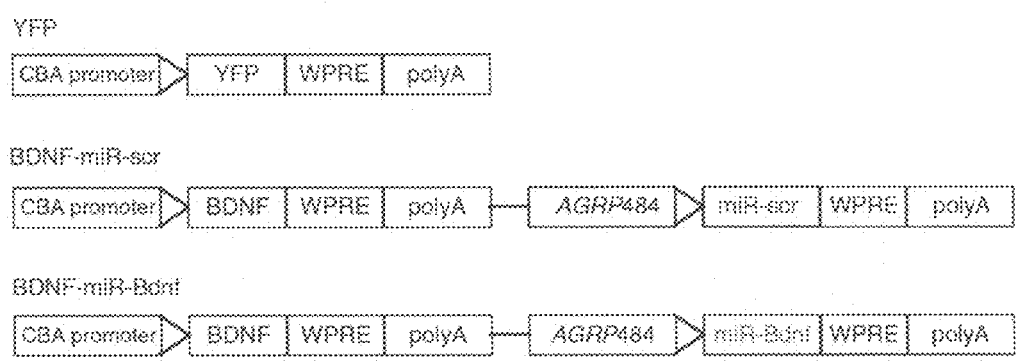
FIGS. 4a-4h: Autoregulatory BDNF vector to treat db/db mice.

We then used AGRP484 to drive a microRNA targeting BDNF (FIG. 8), which we inserted into the parent vector containing the constitutively expressing BDNF complementary DNA cassette. That is, we made a single vector that expressed both BDNF under the control of a general constitutive promoter and a microRNA directed against BDNF under the control of the AGRP promoter (AGRP484-miR-Bdnf), a promoter that increases activity as the mice lose weight (FIG. 4a).

Because rAAV-mediated BDNF expression leads to increased weight loss, the inventors herein now believe that this physiological event would lead to increased AGRP promoter activity. That increased AGRP promoter activity, in turn, would drive the expression of the BDNF-specific microRNA in the same rAAV vector, resulting in a decrease in BDNF expression. Therefore, a balance between weight loss and weight gain would be achieved, thus preventing pathological cachexia from occurring, especially if the treated mouse's diet is not carefully controlled.

We used a mouse model of type 2 diabetes, db/db mice, and delayed the rAAV-mediated treatment until they were extremely obese and diabetic to investigate both the therapeutic efficacy as well as the autoregulatory efficiency of the dual-cassette vectors. When administered a control YFP-encoding virus, db/db mice continued to gain weight (FIG. 4b).

Figure 4B:
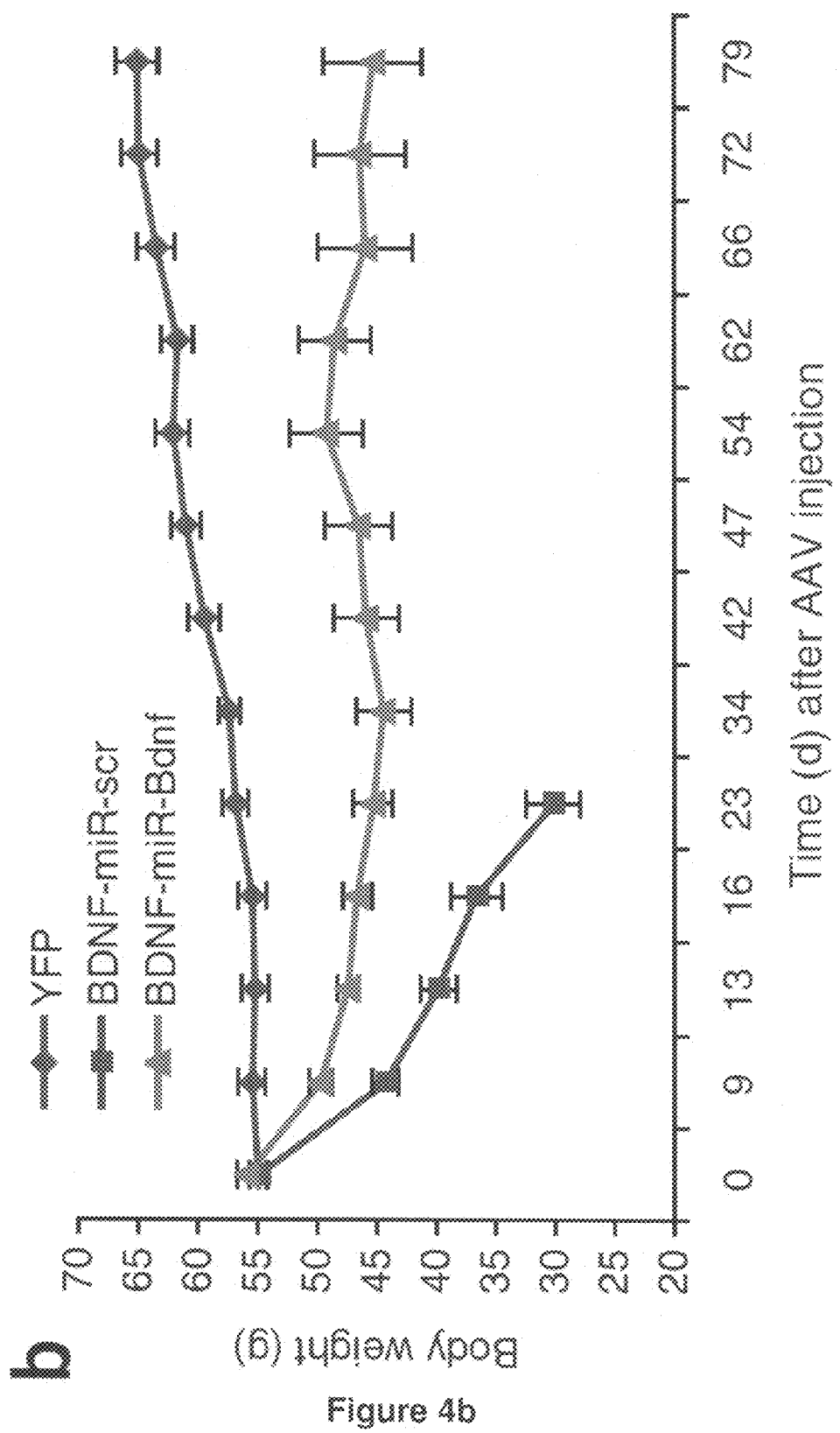
Figure 4C:
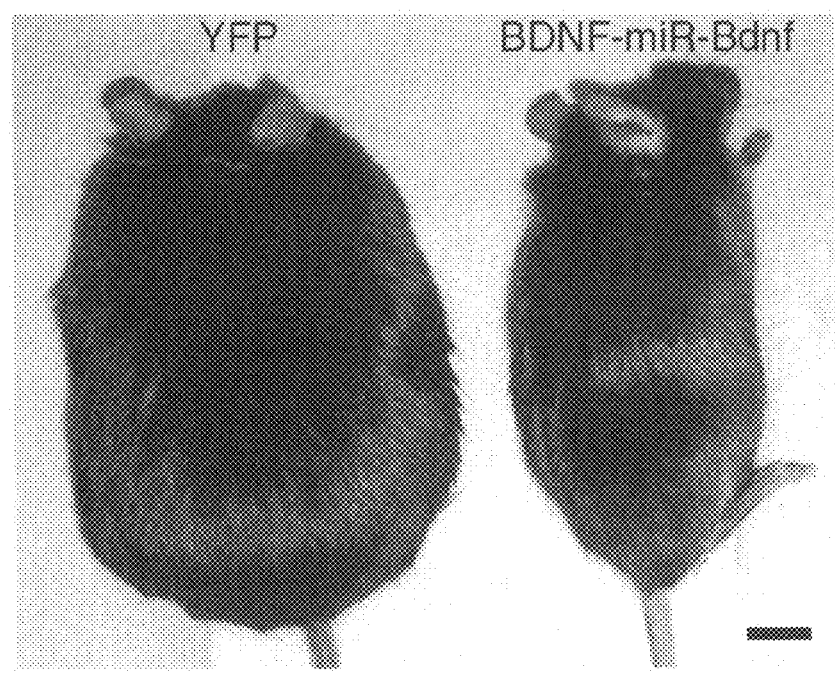

In contrast, when the mice were given a BDNF-encoding vector together with a scrambled microRNA (BDNF-miR-scr, targeting no known genes), their weight dropped precipitously by 45.3%±3.6% in 3 weeks (FIG. 4b). The weights of the mice receiving the BDNF plus the AGRP484-miR-Bdnf dropped markedly but began to level off and stabilized between 3 and 4 weeks after rAAV injection, with body weight maintained for the entire 11-week duration of the experiment, indicating efficient autoregulation of the BDNF transgene expression (FIGS. 4b, 4c).

Figure 4D:
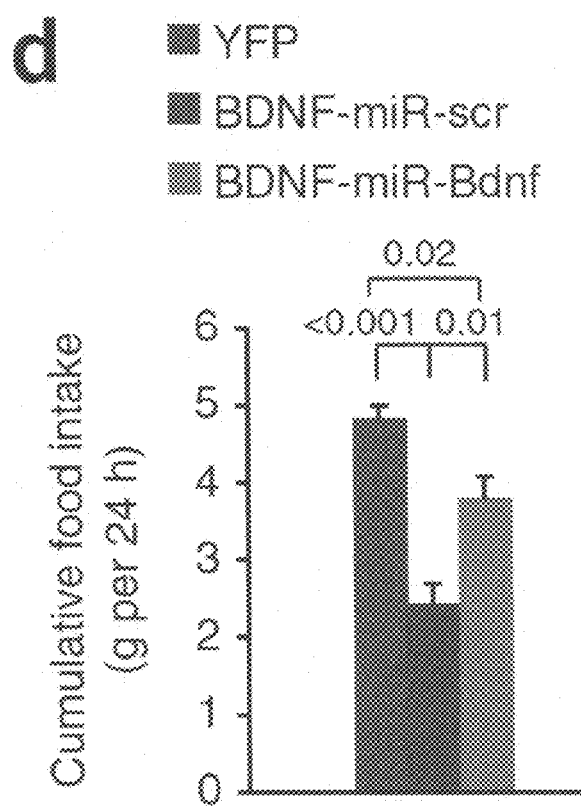
Figure 4E:
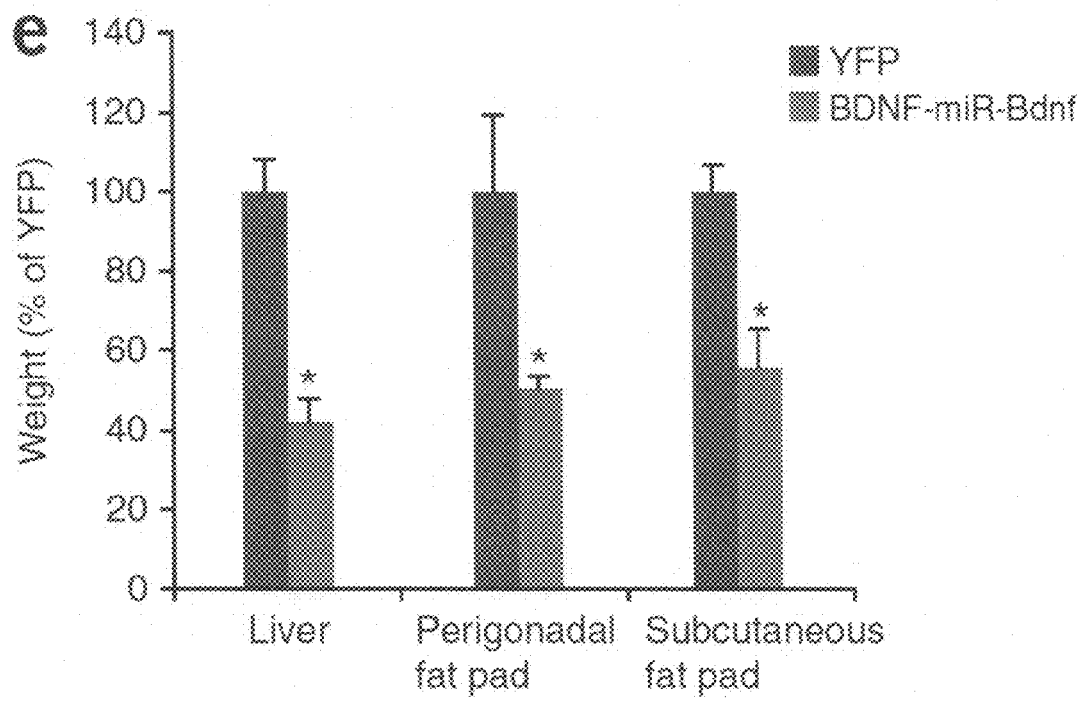
Figure 4F:
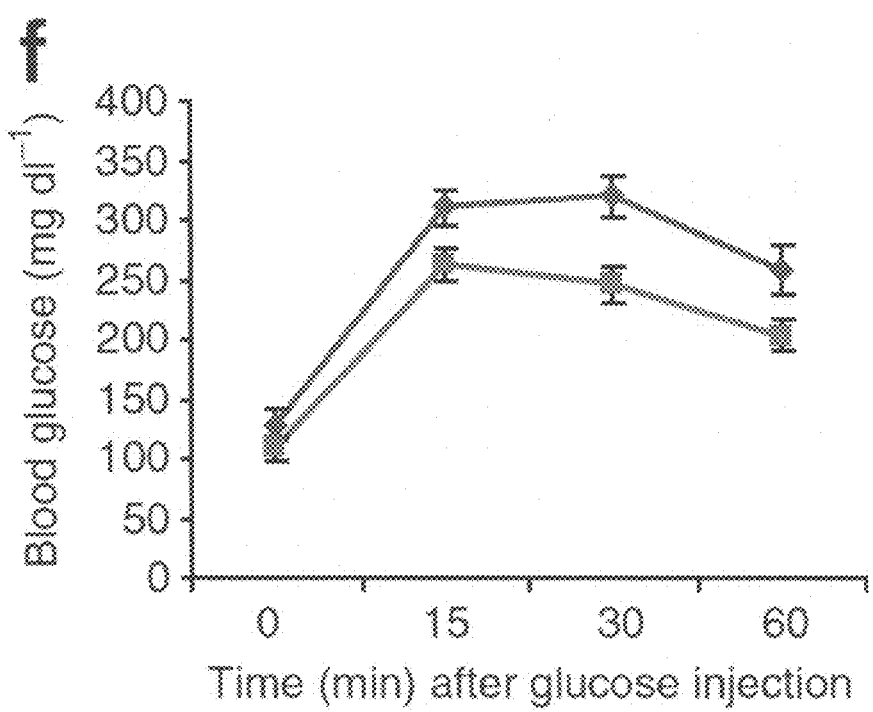
Figure 4G:
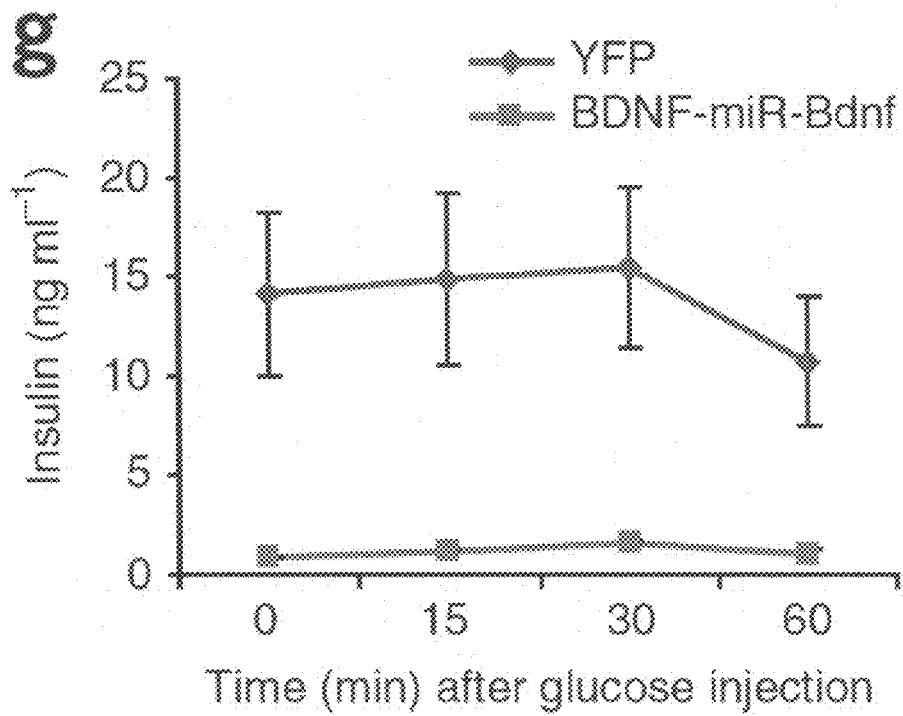
Figure 4H:
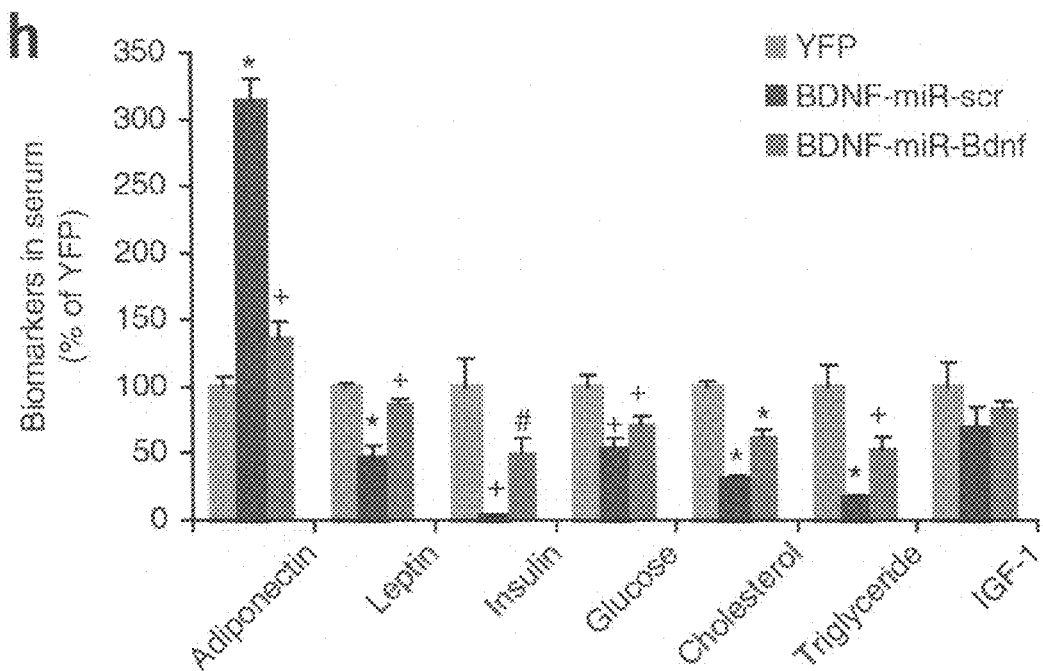

Both BDNF-miR-Bdnf-expressing and BDNF-miR-scr-expressing mice showed reduced food intake compared to YFP-expressing controls (FIG. 4d), with increased rectal temperature indicating increased energy expenditure (data not shown). Moreover, gene therapy with the autoregulatory BDNF vector alleviated the obesity (FIG. 4e), improved the insulin sensitivity and glucose tolerance (FIGS. 4f, 4g) and ameliorated the metabolic disturbances in db/db mice (FIG. 4h).

The profile of hypothalamic gene expression showed a similar pattern to that observed in wild-type mice but with a milder extent of changes that is likely to reflect the more controlled BDNF overexpression (FIG. 9a). Indeed, hypothalamic BDNF levels were 2055.6±402.7 pg mg-1 in BDNF-miR-Bdnf-expressing mice, an 85% reduction from the 13323.3±3899.8 pg mg-1 concentration in the BDNF-miR-Scr-expressing mice (P=0.023), and 100.7±13.1 pg mg-1 in YFP-expressing mice. Gene therapy also improved the mobility of the extremely obese db/db mice and enhanced their physical activity and exploration behavior, as shown in an open-field test (FIG. 10).

BDNF-Induced Weight Loss is Reversible by Transgene Knockout

To provide a further safeguard for this approach and the potential for a clinical rescue procedure, we wanted to use the loxP-Cre recombination system to generate a way to knock out the transgene, should the need arise because of adverse events.

We generated a rAAV vector with the BDNF transgene flanked by two loxP sites (flox-BDNF), which could be subsequently knocked out by a second viral vector delivering Cre recombinase. The rAAV vector encoding a GFP-Cre fusion protein has been shown to efficiently ablate loxP-modified genes in the brain, including the hypothalamus, with low toxicity. Bilateral injection of Cre vector alone did not influence body weight (data not shown) and did not cause toxicity (FIG. 7e and FIGS. 11a, 11b).

To establish an obesity model with greater clinical relevance, we fed C57BL/6 mice with the HFD for 10 weeks until their body weight reached 40 g. The floxed BDNF vector was injected into the hypothalamus of the obese mice with nonfloxed YFP as a control (FIG. 5).

Figure 5A:
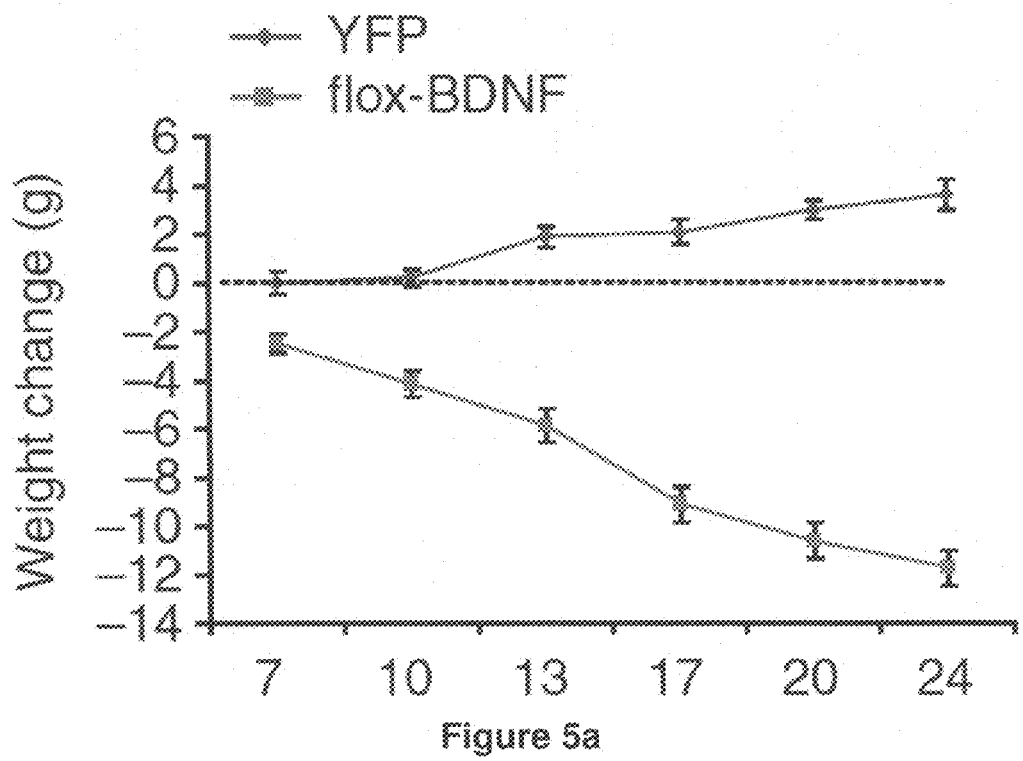
FIGS. 5a-5h: BDNF-induced weight loss is reversible by Cre-loxP-mediated knockout of the transgene.

Flox-BDNF-expressing mice started to lose weight 7 d after injection and by 24 d had lost 29.3%±1.9% of their body weight, at which time the YFP-expressing mice had gained 9.0%±1.5% of their baseline weight (FIG. 5a). Food consumption was slightly but significantly reduced in BDNF-expressing mice (BDNF-expressing mice, 2.06±0.09 g per mouse per d, YFP-expressing mice, 2.44±0.05 g per mouse per d, P=0.003).

Figure 5B:
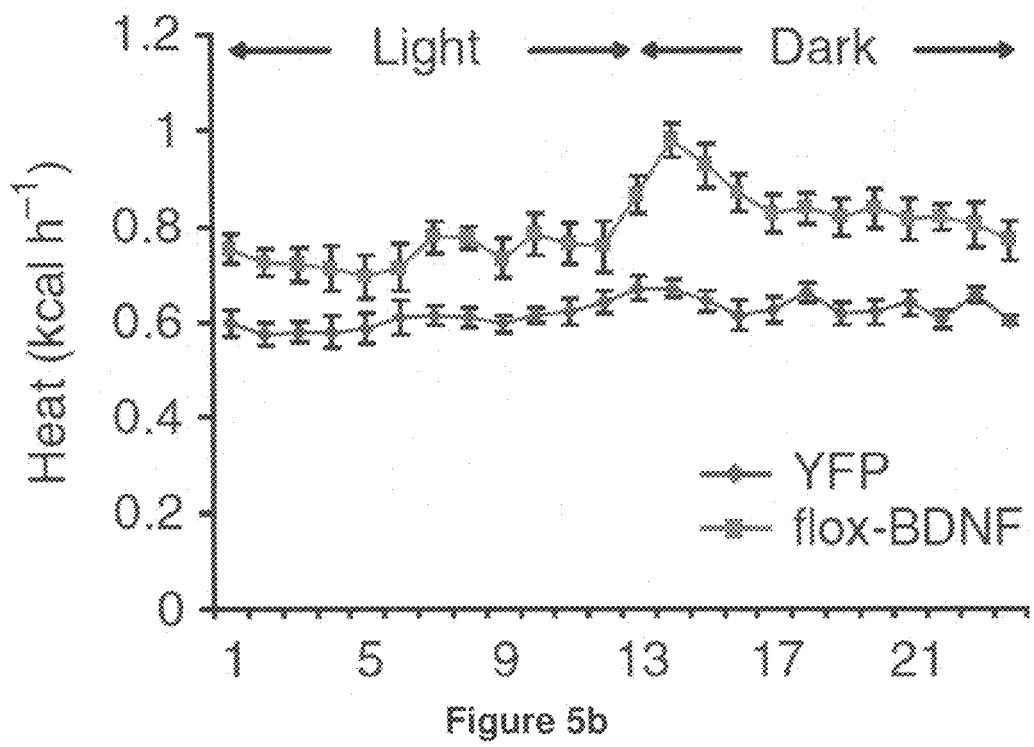

In addition, energy expenditure (kilocalories of heat produced) was markedly increased in BDNF-expressing mice during both the dark phase and light phase (FIG. 5b).

Figure 5C:
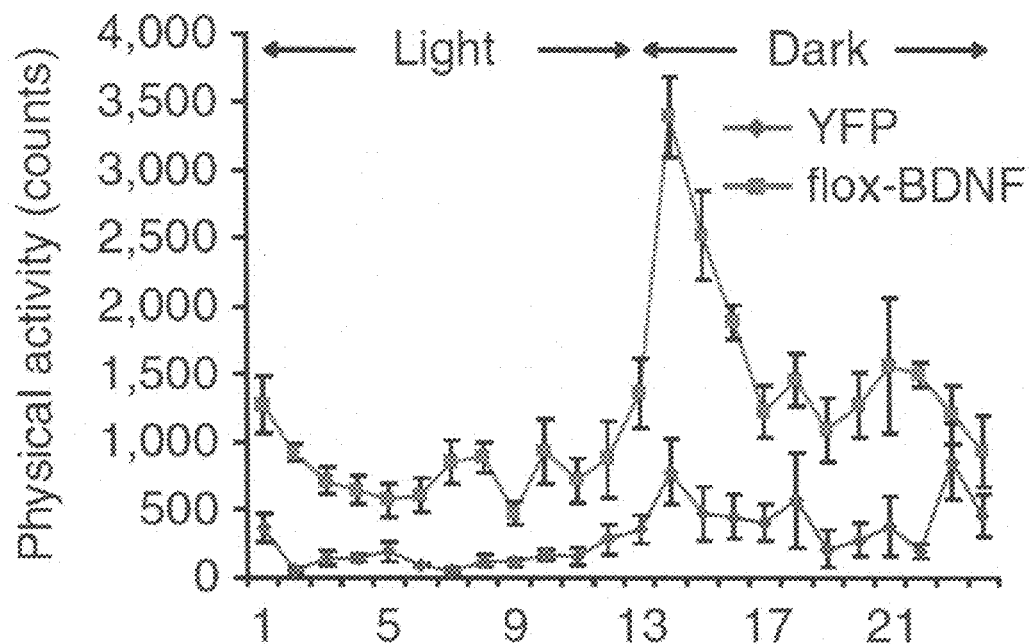
Figure 5D:
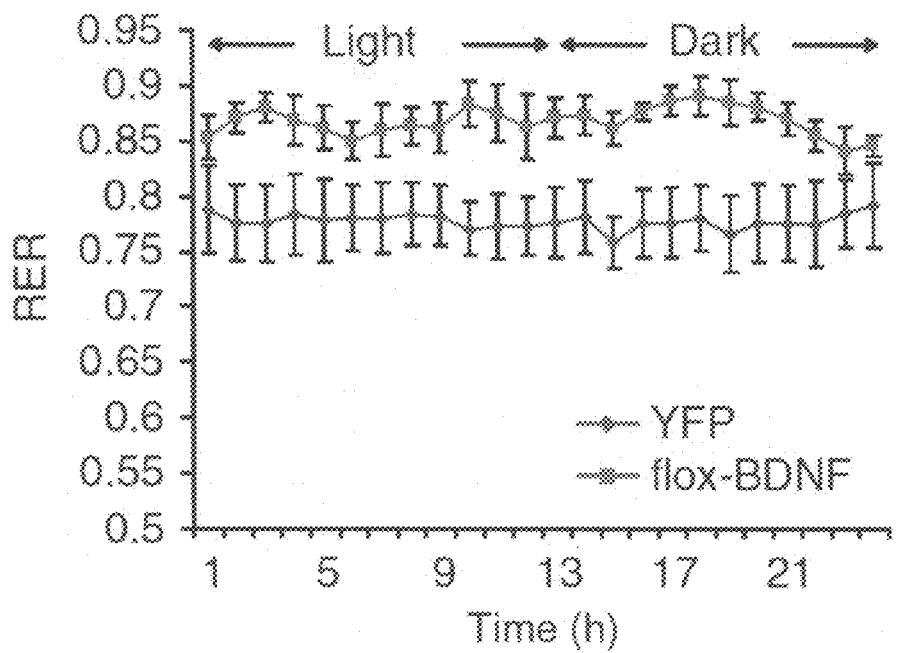

Physical activity was substantially increased in BDNF mice by 4.03±0.28-fold compared to YFP mice in a 24 h period, particularly in the dark phase (FIG. 5c).

Notably, the respiratory exchange ratio was increased from 0.78±0.03 in YFP-expressing mice to 0.87±0.01 in BDNF-expressing mice (FIG. 5d), showing increased carbohydrate oxidation as opposed to lipid oxidation, although both groups were fed with HFD.

Figure 5E:
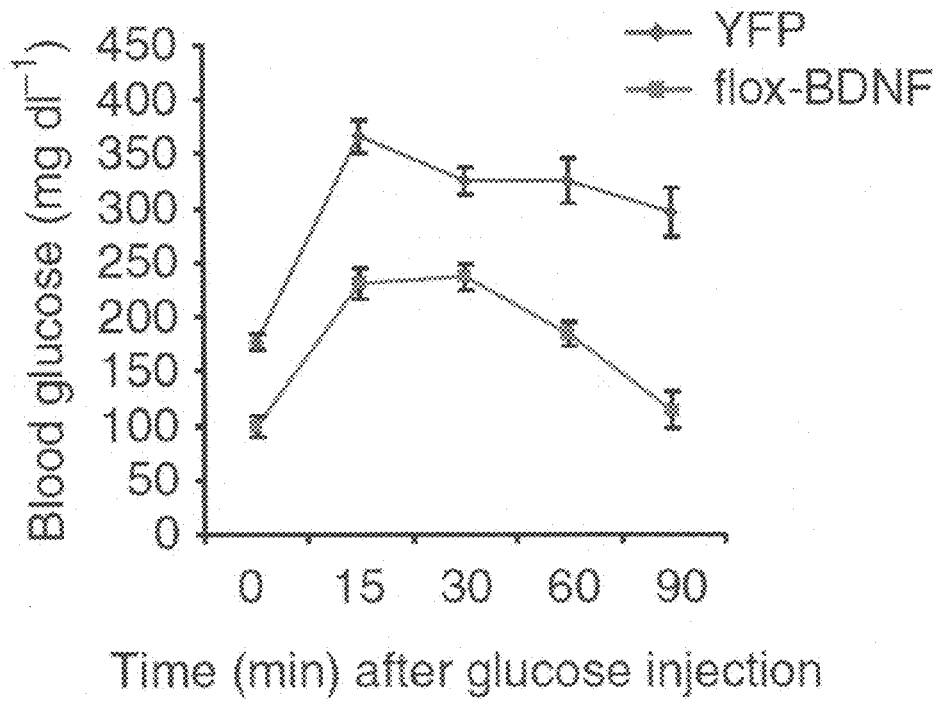

Obesity-associated glucose intolerance was alleviated by BDNF treatment 3 weeks after rAAV injection (FIG. 5e).

We then randomized flox-BDNF-expressing mice to groups receiving a second viral vector injection to the same site as the first surgery by receiving either GFP-Cre or empty viral vector as a control. All YFP-expressing mice received the GFP-Cre viral vector in the second surgery. GFP-Cre vector injection significantly suppressed BDNF mRNA and protein expression by 63.9%±9.0% and 71.6%±1.9%, respectively (P=0.002). Hypothalamic immunohistochemistry showed widespread GFP-Cre expression with less residual HA immunoreactivity, consistent with the ~72% protein knockdown (FIG. 11c).

Moreover, HA-positive cells (those transduced by flox-BDNF vector) and GFP-positive cells (those transduced by GFP-Cre vector) were located in the same area, but no colocalization was observed, consistent with efficient Cre recombinase activity in co-transduced cells (FIG. 11c). After the second surgery, YFP-expressing mice continued to gain weight, whereas flox-BDNF-expressing mice receiving empty vector in the second surgery continued to lose weight, although at a lower rate, and eventually the weight became stable (FIG. 5f).

Figure 5F:
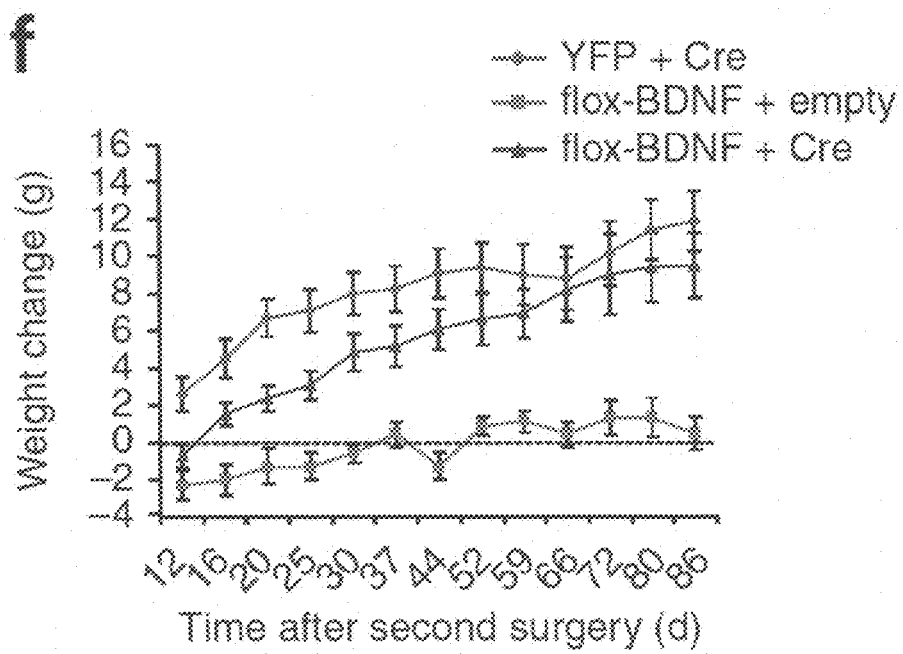

Flox-BDNF-expressing mice receiving Cre virus reversed the progressive weight loss and commenced to regain weight gradually, although their weight remained substantially lower than the YFP-expressing obese mice (FIG. 5f).

Figure 5G:
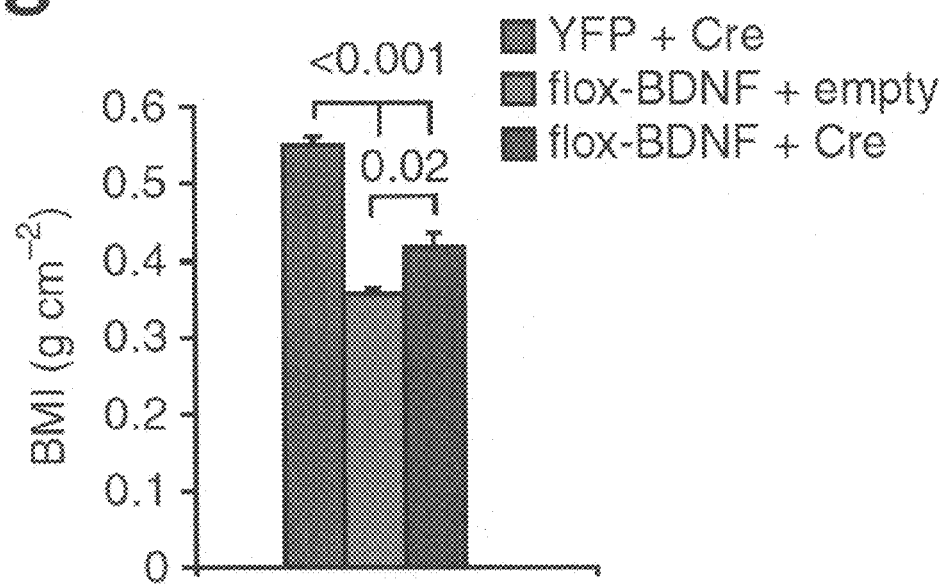
Figure 5H:
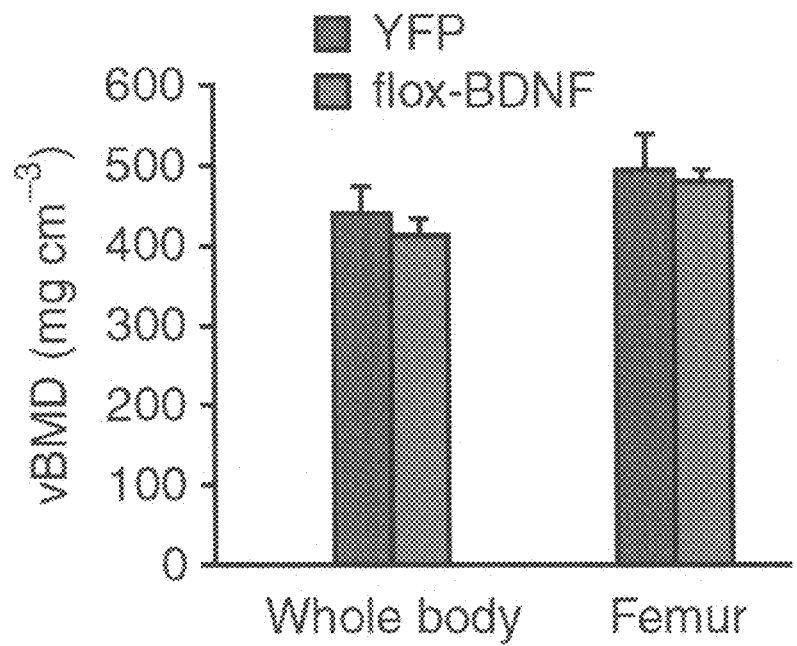

At the end of the study, approximately 4 months after the first surgery, both groups of BDNF-expressing mice showed markedly lower body mass index than the YFP-expressing controls (FIG. 5g).

Because body weight influences bone density and is considered as a risk factor for fracture, we measured the bone mineral density of BDNF-expressing mice after considerable weight loss and found no difference in either the whole-body skeleton (excluding skull) or femur only (FIG. 5h), indicating a lack of adverse effect on bones after BDNF-induced weight loss.

Discussion of Example I

Clinical gene transfer should ideally include some regulatory control of therapeutic gene expression, particularly when constitutive expression of the transgene may be deleterious. Several pharmacological gene regulation technologies have been developed. The Tet regulatory system, based on the use of small molecules such as tetracycline or doxycycline, is the most widely used. However, problems include the basal leakiness of the system and the potential immunogenicity of the foreign proteins, in addition to the need to administer a pharmacological agent with its own attendant risks. A dimerizer-regulated approach such as the rapamycin-FK506-binding protein system allows tight control in vivo and is less likely to be immunogenic, because the key components of this system are derived from human proteins. However, the size limitation of the cloned sequences in rAAV requires splitting the regulatory system into two separate vectors. The use of two separate vectors is inefficient, owing to the need for double infection of the host cell. In addition, it remains a question whether the inducer drugs will be appropriate for the clinic.

Therefore, we constructed an autoregulatory system to control therapeutic gene expression, mimicking the body's natural molecular genetic feedback systems.

Here we show the efficacy of such an approach using BDNF as the therapeutic gene, with weight loss and fat depletion as the physiological readout and an AGRP promoter-driven microRNA cassette as the regulatory agent. All of the components of this system can be packaged into a single rAAV vector for efficient delivery. To evaluate the regulation efficacy in vivo, we used a very high dose of the vector in db/db mice. The unchecked overexpression of BDNF led to marked weight loss, decrease of adiposity and improvement in serum metabolic parameters. However, the weight of mice receiving BDNF coupled with scrambled microRNA continued to drop (over 45% by 3 weeks after AAV injection) and showed no sign of stabilization, ultimately requiring us to euthanize the mice. Moreover, the BDNF-treated mice with severe weight loss and fat depletion, including the wild-type mice on NCD and the db/db mice, both treated with the nonregulated BDNF vectors, had a hyperactive phenotype, and their immunocompetence was compromised (data not shown). In contrast, the body weight of mice receiving an identical dose of the autoregulatory vector, in which the constitutive BDNF cassette was coupled with a physiologically responsive inhibitory microRNA construct, had a more gradual weight loss without any behavioral hyperactivity. The weight loss of these mice reached ~20% by 3 weeks after injection and then plateaued throughout the entire 11-week duration of the experiment.

It is possible that by using experimental mice housed and fed in a tightly controlled laboratory environment, we can titrate the dose of vector to lead to the desirable weight loss without overshoot. However, in a clinical setting, diet and activity may vary unpredictably and from day to day. The efficacy of all current antiobesity approaches is compromised by an inability to mandate both a controlled lifestyle and energy-related activities, as well as by noncompliance to any given diet. Moreover, although repeat dosing is possible in gene therapy, every neurosurgical procedure carries with it some risk, and one of the major advantages of rAAV-mediated gene therapy is the potential for long-term, if not permanent, treatment of a disorder after a single intervention.

The present invention enables a single dosing to which every obese individual could respond and yet adapts and autoregulates regardless of an individual's diet and lifestyle. The marked alleviation of obesity that we observed was associated with loss of liver steatosis, improvement in insulin sensitivity and glucose tolerance, and reversal of hyperleptinemia and lipid dyslipidemia.

In another aspect, the invention can be also used with other molecular intervention studies in which expression of any given functional transgene is self-regulated by a microRNA driven by promoters activated, in turn, by the physiological changes induced by the transgene of interest.

These data, in two obesity and diabetes models, show the potency and long-term efficacy of hypothalamic gene transfer of BDNF. Both suppression of food intake and heightening of energy expenditure contribute to the weight loss of db/db mice receiving BDNF, although the increase in energy expenditure of both basal metabolism and spontaneous activity seems more noteworthy, given that BDNF-overexpressing wild-type mice fed with either NCD or HFD (while weight remained normal) did not change food intake.

Our data, though, are consistent with previous reports that have shown that BDNF has a more potent effect on appetite in obese mice. For example, chronic administration of BDNF protein substantially suppressed food intake in mice with DIO but not those fed on a standard diet. In addition, acute or chronic administration of BDNF protein led to a marked decrease in food intake in genetic obesity models, including yellow agouti mice and db/db mice. This selective effect on appetite suppression in obese mice is believed by the inventors herein to be explained by the basal pattern of anorexic and/or orexigenic signaling in the hypothalamus before BDNF treatment. The orexigenic Agrp and Npy mRNA levels were approximately sixfold and threefold higher in db/db mice than in wild-type mice, respectively, whereas the level of anorexic Pomc was 30% lower (FIG. 9b).

The hyperphagia associated with these obesity models (genetic or diet-induced obesity) reveals the appetite-suppressing effect of BDNF gene therapy that is not apparent in euphagic mice. We also showed that genes encoding proteins involved in energy expenditure, such as Ucps, were considerably upregulated in the liver and WAT of BDNF-expressing mice. Moreover, the comprehensive analysis of gene expression in hypothalamus, liver and fat provides further insights into the potential mechanisms underlying the hypothalamic BDNF regulation of energy balance. For example hypothalamic Crh expression was consistently increased in all of the models we used and, accompanied by the increase in physical activity, showing a potential pathway of BDNF regulation of the hypothalamus-pituitary-adrenal axis, food intake and energy expenditure.

In addition, WAT seems to be a primary peripheral organ responsive to hypothalamic BDNF, with not only the display of much smaller adipocytes but also substantial differences in the expression profile of adipokines and genes involved in lipid metabolism and mitochondrion activity. The WAT reduction was primarily due to a reduction in cell size without much impact on cellular viability, as shown by lack of adipocyte apoptosis (data not shown) and reversible weight gain when the BDNF transgene was knocked out by expression of Cre.

Thus, described herein are several strategies to achieve potent and safe gene therapy for obesity and related metabolic syndromes with AAV-BDNF vectors, including dose adjustment, an autoregulatory negative feedback system using RNAi coupled to transgene-induced physiological changes and, finally, a definitive knockout via delivery of a second, rescue vector.

Long-term observation of mice receiving these therapeutic vectors in both DIO and diabetic genetic models showed improved general health, metabolic parameters and physical activity with no adverse impact on bone density or disturbance in circadian rhythm or home cage activity. The combination of these strategies will further strengthen the safety of this gene therapy approach and provide potent therapeutics for morbid obesity.

EXAMPLE II

Vectors for Delivery of the Heterologous Protein

We developed vectors containing two cassettes, one cassette expresses BDNF driven by a constitutive promoter CBA, the other cassette expresses miR-BDNF driven by AGRP484.

Both transgene and the microRNA inhibiting the same transgene can thus be delivered by a single virus. The constitutive promoter CBA is much stronger than AGRP484. Therefore, the transgene BDNF can achieve high level expression in hypothalamus and lead to weight loss and associated physiological changes. Also, in certain embodiments, a weaker promoter including cellular promoters could also be used to drive the BDNF, since in the obese state the AGRP promoter is dialed right down, but is activated when weight is lost, so at target weight the AGRP promoter could be stronger than the promoter driving the BDNF.

These strong changes can activate AGRP484 to express more microRNA and subsequently tamper down the very high level of BDNF and provide a negative feedback like regulation of transgene expression responsive to physiological changes.

AAV vectors were injected into 3 groups of db/db mice which were leptin receptor defective, obese and diabetic. Mice when receiving YFP control virus continued to gain weight while receiving BDNF plus scramble microRNA lost weight dramatically and their weight continued to drop till sacrifice. On the contrary, mice when given the BDNF plus AGRP-miR-BDNF, lost weight significantly but stabilized between 3 to 4 weeks after injection.

The vectors can be any vector suitable for delivering the nucleic acid encoding a heterologous protein to a host cell at the target site. The term "vector" as used herein refers to any genetic element, such as a plasmid, phage, transposon, cosmid, chromosome, artificial chromosome, virus, virion, non-viral vectors including polymers, liposomes and various non-viral chemical complexes, and the like. Thus, the term includes cloning and expression vehicles, as well as viral vectors.

In one embodiment, the invention uses adeno-associated viral vectors. AAV vectors can be constructed using known techniques to provide at least the operatively linked components of control elements including a transcriptional initiation region, a exogenous nucleic acid molecule, a transcriptional termination region and at least one post-transcriptional regulatory sequence. The control elements are selected to be functional in the targeted cell. The resulting construct which contains the operatively linked components is flanked at the 5' and 3' region with functional AAV ITR sequences.

The nucleotide sequences of AAV ITR regions are known. The AAV ITRs are regions found at each end of the AAV genome which function together in cis as origins of DNA replication and as packaging signals for the viral genome. AAV ITRs, together with the AAV rep coding region, provide for the efficient excision and rescue from, and integration of a nucleotide sequence interposed between two flanking ITRs into a mammalian cell genome. The ITR sequences for AAV-2 are described, for example by Kotin et al. (1994) Human Gene Therapy 5:793-801; Berns "Parvoviridae and their Replication" in Fundamental Virology, 2nd Edition, (B. N. Fields and D. M. Knipe, eds.) The AAV-2 ITR have 145 nucleotides. The terminal 125 nucleotides of each ITR form palindromic hairpin (HP) structures that serve as primers for AAV DNA replication. Each ITR also contains a stretch of 20 nucleotides, designated the D sequence, which is not involved in hairpin structure formation. (See e.g., Wang et al. (1998) J. Virol. 72: 5472-5480 and Wang et al. (1997) J. Virol. 71: 3077-3082). Regions of the inverted terminal repeats (ITR) are designated as A, B, C, A' and D at the 5'-end of the sequences and as D, A', B/C, C/B and A at the 3'-end of the sequences. The site between these regions is referred to as the terminal resolution site, which serves as a cleavage site in the ITRs. For example, the Rep 78 and Rep 68 possess a number of biochemical activities which include binding the viral inverted terminal repeats (ITRs), nicking at the terminal resolution site, and helicase activity. (See e.g., Kotin (1994) Hum. Gene Therap. 5:793-801 and Muzycza et al. (1992) 158:97-129).

The skilled artisan will appreciate that AAV ITR's can be modified using standard molecular biology techniques. Accordingly, AAV ITR's used in the vectors of the invention need not have a wild-type nucleotide sequence, and may be altered, e.g., by the insertion, deletion or substitution of nucleotides. Additionally, AAV ITR's may be derived from any of several AAV serotypes, including but not limited to, AAV-1, AAV-2, AAV-3, AAV-4, AAV-5, AAV-6, AAVX7, and the like. Furthermore, 5' and 3' ITR's which flank a selected nucleotide sequence in an AAV expression vector need not necessarily be identical or derived from the same AAV serotype or isolate, so long as the ITR's function as intended, i.e., to allow for excision and replication of the bounded nucleotide sequence of interest when AAV rep gene products are present in the cell.

It is to be understood that, in certain embodiments, the AAV vector genome can be single stranded containing the ITRs which flank the genome; and in other embodiments, can be double stranded so-called "self-complementary" (sc)AAV which also have ITRs flanking the genome by one ITR which is altered. In one embodiment, there is a deletion in the D-region of one of the ITRs which prevents rep-mediated nicking of the newly synthesized rAAV genome enabling efficient production and packaging of dimeric, double-stranded rAAV genomes into recombinant sc particles.

The AAV rep coding region refers to a region of the AAV genome which encodes the replication proteins of the virus which are required to replicate the viral genome and to insert the viral genome into a host genome during latent infection (Muzyczka, (1992) Current Topics in Microbiol. and Immunol.; Bems, "Parvoviridae and their Replication" in Fundamental Virology, 2d ed., (B. N. Fields and D. M. Knipe, eds.). The term also includes functional homologues thereof such as the human herpesvirus 6 (HHV-6) rep gene which is also known to mediate AAV-2 DNA replication. The rep coding region, as used herein, can be derived from any viral serotype. The region need not include all of the wild-type genes but may be altered, e.g., by the insertion, deletion or substitution of nucleotides, so long as the rep genes function as intended.

The AAV cap coding region refers to a region of the AAV genome which encodes the coat proteins of the virus which are required for packaging the viral genome. The AAV cap coding region, as used herein, can be derived from any AAV serotype. The region need not include all of the wild-type cap genes but may be altered, e.g., by the insertion, deletion or substitution of nucleotides, so long as the genes provide for sufficient packaging functions when present in a host cell along with an AAV vector.

The AAV vectors can be derived from one or more adeno-associated viruses, including without limitation, AAV-1, AAV-2, AAV-3, AAV-4, AAV-5, AAV76, AAV-7, AAV-8, AVV-9, AVV-10. It is to be understood that, in certain embodiments, the AAV vector(s) can include AAV clades isolated from human and non-human primates including recombinants or combinations and chimerics of such.

The AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

The vectors can be produced using "AAV helper functions" or "helpers" which refer to AAV-derived coding sequences that can be expressed to provide AAV gene products that, in turn, function in trans for productive AAV replication. Thus, AAV helper functions include the rep and cap regions. The rep expression products have been shown to possess many functions, including, among others: recognition, binding and nicking of the AAV origin of DNA replication; DNA helicase activity; and modulation of transcription from AAV (or other heterologous) promoters. The cap expression products supply necessary packaging functions. AAV helper functions are used herein to complement AAV functions in trans that are missing from AAV vectors.

An AAV helper construct refers generally to a nucleic acid molecule that includes nucleotide sequences which provide AAV functions. These AAV functions include the rep and cap coding regions that are replaced by a nucleotide sequence of interest in an AAV delivery vector. AAV helper constructs are commonly used to provide transient expression of AAV rep and/or cap genes to complement missing AAV functions that are necessary for lytic AAV replication; however, all previous helper constructs lack AAV ITRs and can neither replicate nor package themselves. AAV helper constructs can be in the form of a plasmid, phage, transposon, cosmid, virus, or virion. A number of other vectors have been described which encode Rep and/or Cap expression products. See, e.g., U.S. Pat. No. 5,139,941. The helper constructs of present invention include at least one copy of AAV ITR or functional equivalent to make it competent for AAV replication and rescue.

It may also be necessary to provide "accessory functions" which refer to non-AAV derived viral and/or cellular functions upon which AAV is dependent for its replication (Carter, (1990) "Adeno-Associated Virus Helper Functions," in CRC Handbook of Parvoviruses, vol. I (P. Tijssen, ed.)). Thus, the term captures DNAs, RNAs and protein that are required for AAV replication, including those moieties involved in activation of AAV gene transcription, stage specific AAV mRNA splicing, AAV DNA replication, synthesis of Cap expression products and AAV capsid assembly. Viral-based accessory functions can be derived from any of the known helper viruses such as adenovirus, herpesvirus (other than herpes simplex virus type-1) and vaccinia virus.

Accessory functions can be provided by "accessory function vector" which refer generally to a nucleic acid molecule that includes nucleotide sequences providing accessory functions. An accessory function vector can be transfected into a suitable host cell, wherein the vector is then capable of supporting AAV virion production in the host cell. Expressly excluded from the term are infectious viral particles as they exist in nature, such as adenovirus, herpesvirus or vaccinia virus particles. Thus, accessory function vectors can be in the form of a plasmid, phage, transposon, cosmid or virus that has been modified from its naturally occurring form.

The skilled artisan can appreciate that regulatory sequences can often be provided from commonly used promoters derived from viruses such as, polyoma, Adenovirus 2, cytomegalovirus and Simian Virus 40. Use of viral regulatory elements to direct expression of the protein can allow for high level constitutive expression of the protein in a variety of host cells. Ubiquitously expressing promoters can also be used include, for example, the early cytomegalovirus promoter Boshart et al. (1985) Cell 41:521-530, herpesvirus thymidine kinase (HSV-TK) promoter (McKnight et al. (1984) Cell 37: 253-262), beta-actin promoters (e.g., the human .beta.-actin promoter as described by Ng et al. (1985) Mol. Cell Biol. 5: 2720-2732) and colony stimulating factor-1 (CSF-1) promoter (Ladner et al. (1987) EMBO J. 6: 2693-2698).

Alternatively, the regulatory sequences of the AAV vector can direct expression of the transgene preferentially in a particular cell type, i.e., tissue-specific regulatory elements can be used. Non-limiting examples of tissue-specific promoters which can be used include, central nervous system (CNS) specific promoters such as, neuron-specific promoters (e.g., the neurofilament promoter; Byrne and Ruddle (1989) Proc. Natl. Acad. Sci. USA 86:5473-5477) and glial specific promoters (Morii et al. (1991) Biochem. Biophys Res. Commun. 175: 185-191).

The AAV vector harboring the transgene flanked by AAV ITRs, can be constructed by directly inserting the transgene into an AAV genome which has had the major AAV open reading frames ("ORFs") excised therefrom. Other portions of the AAV genome can also be deleted, as long as a sufficient portion of the ITRs remain to allow for replication and packaging functions. These constructs can be designed using techniques well known in the art. (See, e.g., Lebkowski et al. (1988) Molec. Cell. Biol. 8:3988-3996; Vincent et al. (1990) Vaccines 90 (Cold Spring Harbor Laboratory Press); Carter (1992) Current Opinion in Biotechnology 3:533-539; Muzyczka (1992) Current Topics in Microbiol. and Immunol. 158: 97-129; Kotin (1994) Human Gene Therapy 5:793-801; Shelling et al. (1994) Gene Therapy 1: 165-169; and Zhou et al. (1994) J. Exp. Med. 179:1867-1875).

Several AAV vectors are available from the American Type Culture Collection ("ATCC") under Accession Numbers 53222, 53223, 53224, 53225 and 53226.

The AAV vectors can be transfected into a host cell with a helper function, e.g., a helper function plasmid (See Section II) and/or accessory functions to produce recombinant AAV virions (rAAV). Recombinant AAV virions (rAAV) refer to an infectious, replication-defective virus composed of an AAV protein shell encapsidating a nucleotide sequence encoding a therapeutic protein that is flanked on both sides by AAV ITRs. A number of transfection techniques are generally known in the art. See, e.g., Graham et al. (1973) Virology, 52:456, Sambrook et al. (1989) Molecular Cloning, a laboratory manual, Cold Spring Harbor Laboratories, N.Y., Davis et al. (1986) Basic Methods in Molecular Biology, Elsevier, and Chu et al. (1981) Gene 13:197. Particularly suitable transfection methods include calcium phosphate co-precipitation (Graham et al. (1973) Virol. 52:456-467), direct micro-injection into cultured cells (Capecchi (1980) Cell 22:479-488), electroporation (Shigekawa et al. (1988) BioTechniques 6:742-751), liposome mediated gene transfer (Mannino et al. (1988) BioTechniques 6:682-690), lipid-mediated transduction (Felgner et al. (1987) Proc. Natl. Acad. Sci. USA 84:7413-7417), and nucleic acid delivery using high-velocity microprojectiles (Klein et al. (1987) Nature 327:70-73).

Suitable host cells for producing recombinant AAV virions include, but are not limited to, microorganisms, yeast cells, insect cells, and mammalian cells, that can be, or have been, used as recipients of a exogenous nucleic acid molecule. Thus, a "host cell" as used herein generally refers to a cell which has been transfected with an exogenous nucleic acid molecule. The host cell includes any eukaryotic cell or cell line so long as the cell or cell line is not incompatible with the protein to be expressed, the selection system chosen or the fermentation system employed.

In one embodiment, cells from the stable human cell line, 293 (readily available through, e.g., the ATCC under Accession No. ATCC CRL1573) are especially useful. Particularly, the human cell line 293, which is a human embryonic kidney cell line that has been transformed with adenovirus type-5 DNA fragments (Graham et al. (1977) J. Gen. Virol. 36:59), and expresses the adenoviral EIA and E1B genes (Aiello et al. (1979) Virology 94:460). The 293 cell line is readily transfected, and provides a particularly convenient platform in which to produce recombinant AAV virions.

For example, FIG. 13a shows the pAM/CBA-NPY-WPRE-BGH plasmid map, and FIG. 13b shows the pAM/CBA-NPY-WPRE-BGH nucleotide sequence [SEQ ID NO:1]. FIG. 13c shows the CAG-BDNF-HA-WPRE sequence [SEQ ID NO:2].

FIG. 14 shows two targeting sequences with the highest scores (Invitrogene RNAi Design Tool) were selected and cloned into the Block-iT PolII miR RNAi expression vector: WPRE 74: CTATGTGGACGCTGCTTTA [SEQ ID NO:3], and WPRE155: TCCTGGTTTGTCTCTTTAT [SEQ ID NO:4]. In in vitro experiments, both miR constructs inhibited BDNF expression by at least 90% when co-transfected with the HA-BDNF-WPRE plasmid, as confirmed by ELISA for BDNF. miR-WPRE74 was chosen to construct the autoregulatory plasmid shown.

FIG. 15: The mRNA for human BDNF [SEQ ID NO:5].

FIG. 16: The mRNA for human trkB [SEQ ID NO:6].

FIG. 17: DNA sequence and gene structure of human AGRP [SEQ ID NO:7].

FIG. 18: DNA sequence for woodchuck post-transcriptional regulatory element (WPRE) [SEQ ID NO:8].

EXAMPLE III

Delivery of the Heterologous Protein to the Target Site

The vectors carrying the nucleic acid encoding at least one heterologous protein can be precisely delivered into specific sites of the central nervous system, and in particular the brain, using stereotactic microinjection techniques. For example, the subject being treated can be placed within a stereotactic frame base (MRI-compatible) and then imaged using high resolution MRI to determine the three-dimensional positioning of the particular region to be treated. The MRI images can then be transferred to a computer having the appropriate stereotactic software, and a number of images are used to determine a target site and trajectory for pharmacological agent microinjection. The software translates the trajectory into three-dimensional coordinates that are precisely registered for the stereotactic frame. In the case of intracranial delivery, the skull will be exposed, burr holes will be drilled above the entry site, and the stereotactic apparatus used to position the needle and ensure implantation at a predetermined depth. The pharmacological agent can be delivered to regions, such as the cells of the spinal cord, brainstem, or brain that are associated with the disease or disorder. For example, target regions can include the medulla, pons, and midbrain, cerebellum, diencephalons (e.g., thalamus, hypothalamus), telencephalon (e.g., corpus stratium, cerebral cortex, or within the cortex, the occipital, temporal, parietal or frontal lobes), or combinations, thereof.

One particular route of delivery is an approach via the ventricles, with or without an endoscope, typically via the lateral ventricle, through to the third ventricle which lies immediately adjacent to the hypothalamus. Another approach is transnasally, typically transphenoidally, in which a direct approach through the nasal sinuses to the base of the brain, and then a device inserted to deliver the vector directly through this skull base approach into the hypothalamus. Still another approach can be to deliver the vector simply into the ventricles with sufficient hypothalamic expression obtained to induce weight loss.

EXAMPLE IV

Delivery of Therapeutic Agents, Pharmaceutical Compositions and Pharmaceutical Administration The therapeutic agents of the invention can be incorporated into pharmaceutical compositions suitable for administration to a subject. Typically, the pharmaceutical composition comprises the vector of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular). In one embodiment, the vector is administered by intravenous infusion or injection. In another embodiment, the vector is administered by intramuscular, by subcutaneous injection, or perorally.

In the most preferred embodiment, the vector is delivered to a specific location using stereotactic delivery.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antigen, antibody or antibody portion) in the required amount in an appropriate solvent with one or a combination of ingredients enumerated above, as required, followed by filtered sterilization.

Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The vector of the present invention can be administered by a variety of methods known in the art. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

The pharmaceutical compositions of the invention may include a "therapeutically effective amount" or a "prophylactically effective amount" of the vectors of the invention. A "therapeutically effective amount" refers to an amount effective, at dosages and for periods of time necessary, to achieve the desired therapeutic result. A therapeutically effective amount of the vector may vary according to factors such as the disease state, age, sex, and weight of the individual, and the ability of the vector to elicit a desired response in the individual. A therapeutically effective amount is also one in which any toxic or detrimental effects of the vector are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

While the invention has been described with reference to various and preferred embodiments, it should be understood by those skilled in the art that various changes may be made and equivalents may be substituted for elements thereof with-

What is claimed is:

1. A gene therapy particle comprising:
a first expression cassette comprised of a heterologous promoter operatively linked to a nucleotide coding sequence (cDNA) encoding a brain derived neurotrophic factor (BDNF) which is linked to WPRE; and, at least a second expression cassette comprised of cDNA AGRP484 nt 568-1051 in SEQ ID NO:7) linked to miR-Bdnf which is, in turn, linked to WPRE74 having SEQ ID NO:3.

2. The gene therapy particle of claim 1, wherein the gene therapy particle further comprises an adeno-associated viral vector, lentiviral vector or adenoviral vector.

3. A gene therapy particle comprising:
a first expression cassette comprised of a heterologous promoter operatively linked to a nucleotide coding sequence (cDNA) encoding a brain derived neurotrophic factor (BDNF) which is linked to WPRE; and
at least a second expression cassette comprised of cDNA AGRP484 (nt 586-1051 in SEQ ID NO: 7) linked to miR-Bdnf which is, in turn, linked to WPRE74 having SEQ ID NO: 3.

4. The gene therapy particle of claim 3, wherein the adeno-associated viral vector is AAV-2, or a modified form of AAV-2 with an altered tropism.

5. The gene therapy particle of claim 3, wherein the AAV nucleotide sequences are derived from AAV serotype 1 (AAV-1).

6. The gene therapy particle of claim 1, wherein the BDNF is a human BDNF.

7. A pharmaceutical composition comprising the gene therapy particle of claim 1, in a biocompatible pharmaceutical carrier.

8. The gene therapy particle of claim 1, wherein the heterologous promoter is chicken β-actin (CBA).

9. The gene therapy particle of claim 1, wherein the promoter of the first expression cassette includes a constitutive promoter.

10. The gene therapy particle of claim 1, wherein the miR-Bdnf comprises SEQ ID NO: 9.

11. The gene therapy particle of claim 1, wherein the BDNF is flanked by two loxP sites (flox-BDNF), wherein the BDNF is capable of being subsequently knocked out by a second viral vector delivering Cre recombinase.

12. A nucleic acid molecule comprising: an expression cassette comprising a heterologous promoter operatively linked to a nucleotide coding sequence (cDNA) encoding a brain derived neurotrophic factor (BDNF) linked to WPRE, and a post-transcriptional regulatory element comprised of cDNA AGRP484 (nt 568-1051 in SEQ ID NO: 7) linked to miR-BDNF which is linked to WPRE74 having SEQ ID NO: 3.

13. The nucleic acid molecule of claim 12, wherein the promoter is chicken β-actin (CBA).

14. The nucleic acid molecule of claim 12, wherein the BDNF is a human BDNF.

15. The nucleic acid molecule of claim 12, wherein the BDNF is flanked by two loxP sites (flox-BDNF), wherein the BDNF is capable of being subsequently knocked out by a second viral vector delivering Cre recombinase.

16. A pharmaceutical composition comprising the nucleic acid molecule of claim 12, in a biocompatible pharmaceutical carrier.

17. The nucleic acid molecule of claim 12, wherein the miR-Bdnf comprises SEQ ID NO: 9.

* * * * *

SEQUENCE LISTING

<160> NUMBER OF SEQ ID NOS: 12

<210> SEQ ID NO 1
<211> LENGTH: 5641
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
tagctgcgcg ctcgctcgct cactgaggcc gcccgggcaa agcccgggcg tcgggcgacc      60
tttggtcgcc cggcctcagt gagcgagcga gcgcgcagag agggagtggc caactccatc     120
actaggggtt ccttgtagtt aatgattaac ccgccatgct acttatctac gtagccatgc     180
tctaggtacc attgacgtca ataatgacgt atgttcccat agtaacgcca atagggactt     240
tccattgacg tcaatgggtg gactatttac ggtaaactgc ccacttggca gtacatcaag     300
tgtatcatat gccaagtacg ccccctattg acgtcaatga cggtaaatgg cccgcctggc     360
attatgccca gtacatgacc ttatgggact ttcctacttg gcagtacatc tacgtattag     420
tcatcgctat taccatggtc gaggtgagcc ccacgttctg cttcactctc cccatctccc     480 cccctcccc accccaatt ttgtatttat ttattttta attatttgt gcagcgatgg     540 gggcgggggg gggggggggg cgcgcgccag gcggggcggg gcgggcgag gggcggggcg     600 gggcgaggcg gagaggtgcg gcggcagcca atcagagcgg cgcgctccga aagtttcctt     660
ttatggcgag gcggcggcgg cggcgccct ataaaaagcg aagcgcgcgg cgggcgggag     720
tcgctgcgac gctgccttcg ccccgtgccc cgctccgccg ccgcctcgcg ccgcccgccc     780
cggctctgac tgaccgcgtt actcccacag gtgagcgggc gggacggccc ttctcctccg     840
ggctgtaatt agcgcttggt ttaatgacgg cttgtttctt ttctgtggct gcgtgaaagc     900
cttgaggggc tccgggaggg ccctttgtgc ggggggagcg gctcggggct gtccgcgggg     960
ggacggctgc cttcgggggg gacggggcag ggcggggttc ggcttctggc gtgtgaccgg    1020
cggctctaga gcctctgcta accatgttca tgccttcttc ttttttcctac agctcctggg    1080 caacgtgctg gttattgtgc tgtctcatca ttttggcaaa gaattggatc cgccatgcta    1140
ggtaacaagc gactggggct gtccggactg accctcgccc tgtccctgct cgtgtgcctg    1200
ggtgcgctgg ccgaggcgta cccctccaag ccggacaacc cggcgagga cgcaccagcg    1260 gaggacatgg ccagatacta ctcagcgctg cgacactaca tcaacctcat caccaggcag    1320
agatatggaa aacgatctag cccagagaca ctgatttcag acctcttgat gagagaaagc    1380
acagaaaatg ttcccagaac tcggcttgaa gaccctgcaa tgtggtgaga attcgatatc    1440
aagcttatcg ataatcaacc tctggattac aaaatttgtg aaagattgac tggtattctt    1500
aactatgttg ctccttttac gctatgtgga tacgctgctt taatgccttt gtatcatgct    1560
attgcttccc gtatggcttt cattttctcc tccttgtata aatcctggtt gctgtctctt    1620
tatgaggagt tgtggcccgt tgtcaggcaa cgtggcgtgg tgtgcactgt gtttgctgac    1680 gcaacccca ctggttgggg cattgccacc acctgtcagc tcctttccgg gactttcgct    1740 ttcccctcc ctattgccac ggcggaactc atcgccgcct gccttgcccg ctgctggaca    1800
```

```
ggggctcggc tgttgggcac tgacaattcc gtggtgttgt cggggaaatc atcgtccttt    1860
ccttggctgc tcgcctgtgt tgccacctgg attctgcgcg ggacgtcctt ctgctacgtc    1920
ccttcggccc tcaatccagc ggaccttcct tcccgcggcc tgctgccggc tctgcggcct    1980
cttccgcgtc ttcgccttcg ccctcagacg agtcggatct ccctttgggc cgcctccccg    2040
catcgatacc gtcgactcgc tgatcagcct cgactgtgcc ttctagttgc cagccatctg    2100
ttgtttgccc ctccccgtg ccttccttga ccctggaagg tgccactccc actgtccttt    2160
cctaataaaa tgaggaaatt gcatcgcatt gtctgagtag gtgtcattct attctggggg    2220
gtggggtggg gcaggacagc aagggggagg attgggaaga caatagcagg catgctgggg    2280
atgcggtggg ctctatggct tctgaggcgg aaagaaccag ctgggctcg  actagagcat    2340
ggctacgtag ataagtagca tggcgggtta atcattaact acaaggaacc cctagtgatg    2400
gagttggcca ctccctctct gcgcgctcgc tcgctcactg aggccgggcg accaaaggtc    2460
gcccgacgcc cgggctttgc ccgggcggcc tcagtgagcg agcgagcgcg cagagctttt    2520
tgcaaaagcc taggcctcca aaaaagcctc ctcactactt ctggaatagc tcagaggccg    2580
aggcggcctc ggcctctgca taaataaaaa aaattagtca gccatggggc ggagaatggg    2640
cggaactggg cggagttagg ggcgggatgg gcggagttag gggcgggact atggttgctg    2700
actaattgag atgcatgctt tgcatacttc tgcctgctgg ggagcctggg gactttccac    2760
acctggttgc tgactaattg agatgcatgc tttgcatact tctgcctgct ggggagcctg    2820
gggactttcc acaccctaac tgacacacat tccacagctg cattaatgaa tcggccaacg    2880
cgcggggaga ggcggtttgc gtattgggcg ctcttccgct tcctcgctca ctgactcgct    2940
gcgctcggtc gttcggctgc ggcgagcggt atcagctcac tcaaaggcgg taatacggtt    3000
atccacagaa tcaggggata acgcaggaaa gaacatgtga gcaaaaggcc agcaaaaggc    3060
caggaaccgt aaaaaggccg cgttgctggc gtttttccat aggctccgcc cccctgacga    3120
gcatcacaaa aatcgacgct caagtcagag gtggcgaaac ccgacaggac tataaagata    3180
ccaggcgttt ccccctggaa gctccctcgt gcgctctcct gttccgaccc tgccgcttac    3240
cggatacctg tccgccttc  tcccttcggg aagcgtggcg ctttctcata gctcacgctg    3300
taggtatctc agttcggtgt aggtcgttcg ctccaagctg ggctgtgtgc acgaaccccc    3360
cgttcagccc gaccgctgcg ccttatccgg taactatcgt cttgagtcca acccggtaag    3420
acacgactta tcgccactgg cagcagccac tggtaacagg attagcagag cgaggtatgt    3480
aggcggtgct acagagttct tgaagtggtg gcctaactac ggctacacta gaagaacagt    3540
atttggtatc tgcgctctgc tgaagccagt taccttcgga aaaagagttg gtagctcttg    3600
atccggcaaa caaccaccg  ctggtagcgg tggttttttt gtttgcaagc agcagattac    3660
gcgcagaaaa aaaggatctc aagaagatcc tttgatcttt tctacggggt ctgacgctca    3720
gtggaacgaa aactcacgtt aagggatttt ggtcatgaga ttatcaaaaa ggatcttcac    3780
ctagatcctt ttaaattaaa aatgaagttt taaatcaatc taaagtatat atgagtaaac    3840
ttggtctgac agttaccaat gcttaatcag tgaggcacct atctcagcga tctgtctatt    3900
tcgttcatcc atagttgcct gactccccgt cgtgtagata actacgatac gggagggctt    3960
accatctggc cccagtgctg caatgatacc gcgagaccca cgctcaccgg ctccagattt    4020
atcagcaata aaccagccag ccggaagggc cgagcgcaga agtggtcctg caactttatc    4080
cgcctccatc cagtctatta attgttgccg ggaagctaga gtaagtagtt cgccagttaa    4140
tagtttgcgc aacgttgttg ccattgctac aggcatcgtg gtgtcacgct cgtcgtttgg    4200
```

```
tatggcttca ttcagctccg gttcccaacg atcaaggcga gttacatgat ccccatgtt    4260 gtgcaaaaaa gcggttagct ccttcggtcc tccgatcgtt gtcagaagta agttggccgc    4320
agtgttatca ctcatggtta tggcagcact gcataattct cttactgtca tgccatccgt    4380
aagatgcttt tctgtgactg gtgagtactc aaccaagtca ttctgagaat agtgtatgcg    4440
gcgaccgagt tgctcttgcc cggcgtcaat acgggataat accgcgccac atagcagaac    4500
tttaaaagtg ctcatcattg gaaaacgttc ttcggggcga aaactctcaa ggatcttacc    4560
gctgttgaga tccagttcga tgtaacccac tcgtgcaccc aactgatctt cagcatcttt    4620
tactttcacc agcgtttctg ggtgagcaaa acaggaagg caaatgccg caaaaaggg      4680 aataagggcg acacggaaat gttgaatact catactcttc cttttcaat attattgaag    4740 catttatcag ggttattgtc tcatgagcgg atacatattt gaatgtattt agaaaaataa    4800
acaaataggg gttccgcgca catttccccg aaaagtgcca cctgacgtct aagaaaccat    4860
tattatcatg acattaacct ataaaaatag gcgtatcacg aggccctttc gtctcgcgcg    4920
tttcggtgat gacggtgaaa acctctgaca catgcagctc ccggagacgg tcacagcttg    4980
tctgtaagcg gatgccggga gcagacaagc ccgtcagggc gcgtcagcgg gtgttggcgg    5040
gtgtcggggc tggcttaact atgcggcatc agagcagatt gtactgagag tgcaccattc    5100
gacgctctcc cttatgcgac tcctgcatta ggaagcagcc cagtagtagg ttgaggccgt    5160
tgagcaccgc cgccgcaagg aatggtgcat gcaaggagat ggcgcccaac agtccccgg    5220 ccacggggcc tgccaccata cccacgccga acaagcgct catgagcccg aagtggcgag    5280
cccgatcttc cccatcggtg atgtcggcga tataggcgcc agcaaccgca cctgtggcgc    5340
cggtgatgcc ggccacgatg cgtccggcgt agaggatctg gctagcgatg accctgctga    5400
ttggttcgct gaccatttcc gggtgcggga cggcgttacc agaaactcag aaggttcgtc    5460
caaccaaacc gactctgacg gcagtttacg agagagatga tagggtctgc ttcagtaagc    5520
cagatgctac acaattaggc ttgtacatat tgtcgttaga acgcggctac aattaataca    5580
taaccttatg tatcatacac atacgattta ggtgacacta tagaatacac ggaattaatt    5640
c                                                                   5641
```

<210> SEQ ID NO 2
<211> LENGTH: 2365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
cattgacgtc aataatgacg tatgttccca tagtaacgcc aatagggact ttccattgac      60
gtcaatgggt ggactattta cggtaaactg cccacttggc agtacatcaa gtgtatcata    120
tgccaagtac gccccctatt gacgtcaatg acggtaaatg gcccgcctgg cattatgccc    180
agtacatgac cttatgggac tttcctactt ggcagtacat ctacgtatta gtcatcgcta    240
ttaccatggt cgaggtgagc cccacgttct gcttcactct ccccatctcc cccccctccc    300 caccccaat tttgtattta tttattttt aattattttg tgcagcgatg ggggcggggg     360 ggggggggg gcgcgcgcca ggcggggcgg gcggggcga ggggcggggc ggggcgaggc     420
ggagaggtgc ggcggcagcc aatcagagcg gcgcgctccg aaagtttcct tttatgcga    480 ggcggcggcg gcggcggccc tataaaaagc gaagcgcgcg gcgggcggga gtcgctgcga    540
```

```
cgctgccttc gccccgtgcc ccgctccgcc gccgcctcgc gccgcccgcc ccggctctga    600
ctgaccgcgt tactcccaca ggtgagcggg cgggacggcc cttctcctcc gggctgtaat    660
tagcgcttgg tttaatgacg gcttgtttct tttctgtggc tgcgtgaaag ccttgagggg    720
ctccgggagg gccctttgtg cggggggagc ggctcggggc tgtccgcggg gggacggctg    780
ccttcggggg ggacggggca gggcggggtt cggcttctgg cgtgtgaccg gcggctctag    840
agcctctgct aaccatgttc atgccttctt cttttttccta cagctcctgg gcaacgtgct    900
ggttattgtg ctgtctcatc attttggcaa agaattggat ccactcgagt ggagctcgcg    960
actagtcgat tcgaattcgg cttgtgatga ccatccttt ccttactatg gttatttcat    1020
actttggttg catgaaggct gcccccatga agaagcaaa catccgagga caaggtggct    1080
tggcctaccc aggtgtgcgg acccatggga ctctggagag cgtgaatggg cccaaggcag    1140
gttcaagagg cttgacatca ttggctgaca cttcgaaca cgtgatagaa gagctgttgg    1200
atgaggacca gaaagttcgg cccaatgaag aaaacaataa ggacgcagac ttgtacacgt    1260
ccagggtgat gctcagtagt caagtgcctt ggagcctcc tcttctcttt ctgctggagg    1320
aatacaaaaa ttacctagat gctgcaaaca tgtccatgag ggtccggcgc cactctgacc    1380
ctgcccgccg aggggagctg agcgtgtgtg acagtattag tgagtgggta acggcggcag    1440
acaaaaagac tgcagtggac atgtcgggcg ggacggtcac agtccttgaa aaggtccctg    1500
tatcaaaagg ccaactgaag caatacttct acgagaccaa gtgcaatccc atgggttaca    1560
caaaagaagg ctgcagggc atagacaaaa ggcattggaa ctcccagtgc cgaactaccc    1620
agtcgtacgt gcgggcccctt accatggata gcaaaagag aattggctgg cgattcataa    1680
ggatagacac ttcttgtgta tgtacattga ccattaaaag gggaagatat ccgtatgatg    1740
ttcctgatta ttgagaattc gatatcaagc ttatcgataa tcaacctctg gattacaaaa    1800
tttgtgaaag attgactggt attcttaact atgttgctcc ttttacgcta tgtggatacg    1860
ctgctttaat gcctttgtat catgctattg cttcccgtat ggctttcatt ttctcctcct    1920
tgtataaatc ctggttgctg tctctttatg aggagttgtg gcccgttgtc aggcaacgtg    1980
gcgtggtgtg cactgtgttt gctgacgcaa cccccactgg ttggggcatt gccaccacct    2040
gtcagctcct ttccgggact ttcgctttcc cctccctat tgccacgcg gaactcatcg    2100 ccgcctgcct tgcccgctgc tggacagggg ctcggctgtt gggcactgac aattccgtgg    2160
tgttgtcggg gaaatcatcg tccttccctt ggctgctcgc ctgtgttgcc acctggattc    2220
tgcgcgggac gtccttctgc tacgtccctt cggccctcaa tccagcggac cttccttccc    2280
gcggcctgct gccggctctg cggcctcttc cgcgtcttcg ccttcgccct cagacgagtc    2340
ggatctccct ttgggccgcc tcccc                                          2365
```

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctatgtggac gctgcttta                                                 19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
tcctggtttg tctctttat                                                    19

<210> SEQ ID NO 5
<211> LENGTH: 4755
<212> TYPE: DNA
<213> ORGANISM: Homo sapiens

<400> SEQUENCE: 5
cacacacaca cacacacaca gagagaacat ctctagtaaa agaaaagtt gagctttctt        60 agctagatgt gtgtattagc cagaaaaagc caaggagtga agggttttag agaactggag      120
gagataaagt ggagtctgca tatgggaggc atttgaaatg gacttaaatg tcttttaat       180 gctgactttt tcagttttct ccttaccaga cacattgttt tcatgacatt agccccaggc      240
atagacacat cattaaaatg aacatgtcaa aaatgatttt ctgtttagaa ataagcaaaa      300
cattttcagt tgtgaccacc caggtgtaga ataaagaaca gtggaattgg gagccctgag      360
ttctaacata aactttcttc atgacataag gcaagtcttc tatggccttt ggtttcctta     420
cctgtaaaac aggatggctc aatgaaatta tctttcttct ttgctataat agagtatctc     480
tgtgggaaga ggaaaaaaaa agtcaattta aaggctcctt atagttcccc aactgctgtt      540
ttattgtgct attcatgcct agacatcaca tagctagaaa ggcccatcag acccctcagg     600
ccactgctgt tcctgtcaca cattcctgca aaggaccatg ttgctaactt gaaaaaaatt     660
actattaatt acacttgcag ttgttgctta gtaacattta tgattttgtg tttctcgtga    720
cagcatgagc agagatcatt aaaaattaaa cttacaaagc tgctaaagtg ggaagaagga    780
gaacttgaag ccacaatttt tgcacttgct tagaagccat ctaatctcag gttatatgct    840
agatcttggg ggcaaacact gcatgtctct ggtttatatt aaaccacata cagcacacta   900
ctgacactga tttgtgtctg gtgcagctgg agtttatcac caagacataa aaaaaccttg   960
accctgcaga atggcctgga attacaatca gatgggccac atggcatccc ggtgaaagaa  1020
agccctaacc agtttttctgt cttgtttctg cttctctccct acagttccac caggtgagaa  1080
gagtgatgac catccttttc cttactatgg ttatttcata ctttggttgc atgaaggctg   1140 ccccccatgaa agaagcaaac atccgaggac aaggtggctt ggcctaccca ggtgtgcgga   1200 cccatggac tctggagagc gtgaatgggc ccaaggcagg ttcaagaggc ttgacatcat    1260
tggctgacac tttcgaacac gtgatagaag agctgttgga tgaggaccag aaagttcggc   1320
ccaatgaaga aaacaataag gacgcagact tgtacacgtc cagggtgatg ctcagtagtc   1380
aagtgccttt ggagcctcct cttctctttc tgctggagga atacaaaaat tacctagatg   1440
ctgcaaacat gtccatgagg gtccggcgcc actctgaccc tgcccgccga ggggagctga  1500
gcgtgtgtga cagtattagt gagtgggtaa cggcggcaga caaaagact gcagtggaca    1560 tgtcgggcgg gacggtcaca gtccttgaaa aggtccctgt atcaaaaggc caactgaagc   1620
aatacttcta cgagaccaag tgcaatccca tgggttacac aaaagaaggc tgcaggggca   1680
tagacaaaag gcattggaac tcccagtgcc gaactaccca gtcgtacgtg cgggccctta   1740
ccatggatag caaaaagaga attggctggc gattcataag gatagacact tcttgtgtat   1800

-continued

```
gtacattgac cattaaaagg ggaagatagt ggatttatgt tgtatagatt agattatatt    1860
gagacaaaaa ttatctattt gtatatatac ataacagggt aaattattca gttaagaaaa    1920
aaataatttt atgaactgca tgtataaatg aagtttatac agtacagtgg ttctacaatc    1980
tatttattgg acatgtccat gaccagaagg gaaacagtca tttgcgcaca acttaaaaag    2040
tctgcattac attccttgat aatgttgtgg tttgttgccg ttgccaagaa ctgaaaacat    2100
aaaaagttaa aaaaaataat aaattgcatg ctgctttaat tgtgaattga taataaactg    2160
tcctctttca gaaaacagaa aaaacacac acacacacaa caaaaatttg aaccaaaaca     2220
ttccgtttac attttagaca gtaagtatct tcgttcttgt tagtactata tctgttttac    2280
tgcttttaac ttctgatagc gttggaatta aaacaatgtc aaggtgctgt tgtcattgct    2340
ttactggctt aggggatggg ggatgggggg tatatttttg tttgttttgt gttttttttt    2400
cgtttgtttg ttttgttttt tagttcccac agggagtaga gatggggaaa gaattcctac    2460
aatatatatt ctggctgata aaagatacat ttgtatgttg tgaagatgtt tgcaatatcg    2520
atcagatgac tagaaagtga ataaaaatta aggcaactga acaaaaaaat gctcacactc    2580
cacatcccgt gatgcacctc ccaggccccg ctcattcttt gggcgttggt cagagtaagc    2640
tgcttttgac ggaaggacct atgtttgctc agaaacacatt ctttccccccc ctccccctct   2700 ggtctcctct ttgttttgtt ttaaggaaga aaaatcagtt gcgcgttctg aaatatttta    2760
ccactgctgt gaacaagtga acacattgtg tcacatcatg acactcgtat aagcatggag    2820
aacagtgatt tttttttaga acagaaaaca acaaaaaata accccaaaat gaagattatt    2880
ttttatgagg agtgaacatt tgggtaaatc atggctaagc ttaaaaaaaa ctcatggtga    2940
ggcttaacaa tgtcttgtaa gcaaaaggta gagccctgta tcaacccaga aacacctaga    3000
tcagaacagg aatccacatt gccagtgaca tgagactgaa cagccaaatg gaggctatgt    3060
ggagttggca ttgcatttac cggcagtgcg ggaggaattt ctgagtggcc atcccaaggt    3120
ctaggtggag gtggggcatg gtatttgaga cattccaaaa cgaaggcctc tgaaggaccc    3180
ttcagaggtg gctctggaat gacatgtgtc aagctgcttg gacctcgtgc tttaagtgcc    3240
tacattatct aactgtgctc aagaggttct cgactggagg accacactca agccgactta    3300
tgcccaccat cccacctctg gataattttg cataaaattg gattagcctg gagcaggttg    3360
ggagccaaat gtggcatttg tgatcatgag attgatgcaa tgagatagaa gatgtttgct    3420
acctgaacac ttattgcttt gaaactagac ttgaggaaac cagggtttat cttttgagaa    3480
cttttggtaa gggaaaaggg aacaggaaaa gaaaccccaa actcaggccg aatgatcaag    3540
gggacccata ggaaatcttg tccagagaca agacttcggg aaggtgtctg gacattcaga    3600
acaccaagac ttgaaggtgc cttgctcaat ggaagaggcc aggacagagc tgacaaaatt    3660
ttgctcccca gtgaaggcca cagcaacctt ctgcccatcc tgtctgttca tggagagggt    3720
ccctgcctca cctctgccat tttgggttag gagaagtcaa gttgggagcc tgaaatagtg    3780
gttcttggaa aaatggatcc ccagtgaaaa ctagagctct aagcccattc agcccatttc    3840
acacctgaaa atgttagtga tcaccacttg gaccagcatc cttaagtatc agaaagcccc    3900
aagcaattgc tgcatcttag tagggtgagg gataagcaaa agaggatgtt caccataacc    3960
caggaatgaa gataccatca gcaaagaatt tcaatttgtt cagtctttca tttagagcta    4020
gtctttcaca gtaccatctg aatacctctt tgaaagaagg aagactttac gtagtgtaga    4080
tttgttttgt gttgttgaa aatattatct ttgtaattat ttttaatatg taaggaatgc    4140
ttggaatatc tgctatatgt caactttatg cagcttcctt ttgagggaca aatttaaaac    4200
```

| | |
|---|---:|
| aaacaacccc ccatcacaaa cttaaaggat tgcaagggcc agatctgtta agtggtttca | 4260 |
| taggagacac atccagcaat tgtgtggtca gtggctcttt tacccaataa gatacatcac | 4320 |
| agtcacatgc ttgatggttt atgttgacct aagatttatt ttgttaaaat ctctctctgt | 4380 |
| tgtgttcgtt cttgttctgt tttgttttgt tttttaaagt cttgctgtgg tctcttttgtg | 4440 |
| gcagaagtgt ttcatgcatg gcagcaggcc tgttgctttt ttatggcgat tcccattgaa | 4500 |
| aatgtaagta aatgtctgtg gccttgttct ctctatggta aagatattat tcaccatgta | 4560 |
| aaacaaaaaa caatatttat tgtatttag tatatttata taattatgtt attgaaaaaa | 4620 |
| attggcatta aaacttaacc gcatcagaac ctattgtaaa tacaagttct atttaagtgt | 4680 |
| actaattaac atataatata tgttttaaat atagaatttt taatgttttt aaatatattt | 4740 |
| tcaaagtaca taaaa | 4755 |

<210> SEQ ID NO 6
<211> LENGTH: 5608
<212> TYPE: DNA
<213> ORGANISM: Homo sapiens

<400> SEQUENCE: 6

| | |
|---|---:|
| aagacggatt ctcagacaag gcttgcaaat gccccgcagc catcatttaa ctgcacccgc | 60 |
| agaatagtta cggtttgtca cccgaccctc ccggatcgcc taatttgtcc ctagtgagac | 120 |
| cccgaggctc tgcccgcgcc tggcttcttc gtagctggat gcatatcgtg ctccgggcag | 180 |
| cgcgggcgca gggcacgcgt tcgcgcacac cctagcacac atgaacacgc gcaagagctg | 240 |
| aaccaagcac ggtttccatt tcaaaaaggg agacagcctc taccgcgatt gtagaagaga | 300 |
| ctgtggtgtg aattagggac cgggaggcgt cgaacggagg aacggttcat cttagagact | 360 |
| aatttctgg agtttctgcc cctgctctgc gtcagccctc acgtcacttc gccagcagta | 420 |
| gcagaggcgg cggcggcggc tcccggaatt gggttggagc aggagcctcg ctggctgctt | 480 |
| cgctcgcgct ctacgcgctc agtccccggc ggtagcagga gcctggaccc aggcgccgcc | 540 |
| ggcgggcgtg aggcgccgga cccggcctc gaggtgcata ccggaccccc attcgcatct | 600 |
| aacaaggaat ctgcgcccca gagagtcccg ggagcgccgc cggtcggtgc ccggcgcgcc | 660 |
| gggccatgca gcgacggccg ccgcggagct ccgagcagcg gtagcgcccc cctgtaaagc | 720 |
| ggttcgctat gccggggcca ctgtgaaccc tgccgcctgc cggaacactc ttcgctccgg | 780 |
| accagctcag cctctgataa gctggactcg gcacgcccgc aacaagcacc gaggagttaa | 840 |
| gagagccgca agcgcaggga aggcctcccc gcacgggtgg gggaaagcgg ccggtgcagc | 900 |
| gcggggacag gcactcgggc tggcactggc tgctagggat gtcgtcctgg ataaggtggc | 960 |
| atggacccgc catggcgcgg ctctgggggct tctgctggct ggttgtgggc ttctggaggg | 1020 |
| ccgctttcgc ctgtcccacg tcctgcaaat gcagtgcctc tcggatctgg tgcagcgacc | 1080 |
| cttctcctgg catcgtggca tttccgagat tggagcctaa cagtgtagat cctgagaaca | 1140 |
| tcaccgaaat tttcatcgca aaccagaaaa ggttagaaat catcaacgaa gatgatgttg | 1200 |
| aagcttatgt gggactgaga atctgacaa ttgtggattc tggattaaaa tttgtggctc | 1260 |
| ataaagcatt tctgaaaaac agcaacctgc agcacatcaa ttttacccga acaaactga | 1320 |
| cgagtttgtc taggaaacat ttccgtcacc ttgacttgtc tgaactgatc ctggtgggca | 1380 |
| atccatttac atgctcctgt gacattatgt ggatcaagac tctccaagag gctaaatcca | 1440 |
| gtccagacac tcaggatttg tactgcctga atgaaagcag caagaatatt cccctggcaa | 1500 |
| acctgcagat acccaattgt ggtttgccat ctgcaaatct ggccgcacct aacctcactg | 1560 |

-continued

```
tggaggaagg aaagtctatc acattatcct gtagtgtggc aggtgatccg gttcctaata    1620
tgtattggga tgttggtaac ctggtttcca acatatgaa tgaaacaagc cacacacagg     1680
gctccttaag gataactaac atttcatccg atgacagtgg gaagcagatc tcttgtgtgg    1740
cggaaaatct tgtaggagaa gatcaagatt ctgtcaacct cactgtgcat tttgcaccaa    1800
ctatcacatt tctcgaatct ccaacctcag accaccactg gtgcattcca ttcactgtga    1860
aaggcaaccc caaaccagcg cttcagtggt tctataacgg ggcaatattg aatgagtcca    1920
aatacatctg tactaaaata catgttacca atcacacgga gtaccacggc tgcctccagc    1980
tggataatcc cactcacatg aacaatgggg actacactct aatagccaag aatgagtatg    2040
ggaaggatga gaaacagatt tctgctcact tcatgggctg gcctggaatt gacgatggtg    2100
caaacccaaa ttatcctgat gtaatttatg aagattatgg aactgcagcg aatgacatcg    2160
gggacaccac gaacagaagt aatgaaatcc cttccacaga cgtcactgat aaaaccggtc    2220
gggaacatct ctcggtctat gctgtggtgg tgattgcgtc tgtggtggga ttttgccttt    2280
tggtaatgct gtttctgctt aagttggcaa gacactccaa gtttggcatg aaagatttct    2340
catggtttgg atttgggaaa gtaaaatcaa gacaaggtgt tggcccagcc tccgttatca    2400
gcaatgatga tgactctgcc agcccactcc atcacatctc caatgggagt aacactccat    2460
cttcttcgga aggtggccca gatgctgtca ttattggaat gaccaagatc cctgtcattg    2520
aaaatcccca gtactttggc atcaccaaca gtcagctcaa gccagacaca tttgttcagc    2580
acatcaagcg acataacatt gttctgaaaa gggagctagg cgaaggagcc tttggaaaag    2640
tgttcctagc tgaatgctat aacctctgtc ctgagcagga caagatcttg gtggcagtga    2700
agacgctgaa ggatgccagt gacaatgcac gcaaggactt ccaccgtgag gccgagctcc    2760
tgaccaacct ccagcatgag cacatcgtca agttctatgg cgtctgcgtg gagggcgacc    2820
ccctcatcat ggtctttgag tacatgaagc atgggggacct caacaagttc ctcagggcac    2880
acggccctga tgccgtgctg atggctgagg caacccgcc cacggaactg acgcagtcgc    2940
agatgctgca tatagcccag cagatcgccg cgggcatggt ctacctggcg tcccagcact    3000
tcgtgcaccg cgatttggcc accaggaact gcctggtcgg ggagaacttg ctggtgaaaa    3060
tcggggactt tgggatgtcc cgggacgtgt acagcactga ctactacagg gtcggtggcc    3120
acacaatgct gcccattcgc tggatgcctc cagagagcat catgtacagg aaattcacga    3180
cggaaagcga cgtctggagc ctgggggtcg tgttgtggga gattttcacc tatggcaaac    3240
agccctggta ccagctgtca aacaatgagg tgatagagtg tatcactcag ggccgagtcc    3300
tgcagcgacc ccgcacgtgc ccccaggagg tgtatgagct gatgctgggg tgctggcagc    3360
gagagcccca catgaggaag aacatcaagg gcatccatac cctccttcag aacttggcca    3420
aggcatctcc ggtctacctg gacattctag gctagggccc ttttccccag accgatcctt    3480
cccaacgtac tcctcagacg ggctgagagg atgaacatct tttaactgcc gctgaggcc     3540
accaagctgc tctccttcac tctgacagta ttaacatcaa agactccgag aagctctcga    3600
gggaagcagt gtgtacttct tcatccatag acacagtatt gacttctttt tggcattatc    3660
tctttctctc tttccatctc ccttggttgt tccttttttct tttttttaaat tttcttttttc    3720
ttttttttttt cgtcttccct gcttcacgat tcttacccctt tcttttgaat caatctggct   3780
tctgcattac tattaactct gcatagacaa aggccttaac aaacgtaatt tgttatatca    3840
gcagacactc cagtttgccc accacaacta acaatgcctt gttgtattcc tgcctttgat    3900
gtggatgaaa aaagggaaa acaaatattt cacttaaact ttgtcacttc tgctgtacag     3960
```

| | |
|---|---|
| atatcgagag tttctatgga ttcacttcta tttatttatt attattactg ttcttattgt | 4020 |
| ttttggatgg cttaagcctg tgtataaaaa agaaaacttg tgttcaatct gtgaagcctt | 4080 |
| tatctatggg agattaaaac cagagagaaa gaagatttat tatgaaccgc aatatgggag | 4140 |
| gaacaaagac aaccactggg atcagctggt gtcagtccct acttaggaaa tactcagcaa | 4200 |
| ctgttagctg ggaagaatgt attcggcacc ttcccctgag gacctttctg aggagtaaaa | 4260 |
| agactactgg cctctgtgcc atggatgatt cttttcccat caccagaaat gatagcgtgc | 4320 |
| agtagagagc aaagatggct tccgtgagac acaagatggc gcatagtgtg ctcggacaca | 4380 |
| gttttgtctt cgtaggttgt gatgatagca ctggttttgt tctcaagcgc tatccacaga | 4440 |
| accttttgtca acttcagttg aaaagaggtg gattcatgtc cagagctcat ttcggggtca | 4500 |
| ggtgggaaag ccaagaactt ggaaaagata agacaagcta taaattcgga ggcaagtttc | 4560 |
| ttttacaatg aacttttcag atctcacttc cctccgaccc ctaacttcca tgcccacccg | 4620 |
| tcctttaac tgtgcaagca aaattgtgca tggtcttcgt cgattaatac cttgtgtgca | 4680 |
| gacactactg ctccagacgt cgtttccctg ataggtagac cagatccata aaaaggtatg | 4740 |
| acttatacaa ttaggggaag ctaatggagt ttattagctg agtatcaatg tctctgcgtt | 4800 |
| gtacggtggt gatgggtttt aatgaatatg daccctgaag cctggaaatc ctcatccacg | 4860 |
| tcgaacccac aggactgtgg gaagggcaga atcaatccct aagggaaagg aaacctcacc | 4920 |
| ctgagggcat cacatgcact catgttcagt gtacacaggt caagtccctt gctctgggct | 4980 |
| ctagttggga gagtggtttc attccaagtg tactccattg tcagtatgct gttttgtttt | 5040 |
| ccttcactcc attcaaaaag tcaaaataca aaatttggca cagcatgcca acgggaggct | 5100 |
| gtgcccagac caagcactgg aagtgtgctt ctaggcatag tcattggttt tgcaaaaaga | 5160 |
| gggctcaaat ttaaatagaa atttacagct atttgaatgg tcagatatac caagaaagaa | 5220 |
| aaatatttct gttcctcaag aaaacttgct accctctgtg aggggaattt tgctaaactt | 5280 |
| gacatcttta taacatgagc cagattgaaa gggagtgatt tcattcatc ttaggtcatg | 5340 |
| ttatttcata tttgtttctg aaggtgcgat agctctgttt taggttttgc ttgcgcctgt | 5400 |
| taattactgg aacaccttat ttttcattaa aggctttgaa agccaattct caaaaattca | 5460 |
| aaagtgcaaa ttaacagaac aaaaggaaat ccagtagcaa ctgcagtcaa gcgagggagt | 5520 |
| tgacaagata aaccttacgt ccattcaagt tatatgctgg cctatgagag atgagagttg | 5580 |
| ggtcgtttgt tctctttgtt gatgatttt | 5608 |

<210> SEQ ID NO 7
<211> LENGTH: 1930
<212> TYPE: DNA
<213> ORGANISM: Homo sapiens
<220> FEATURE:
<221> NAME/KEY: modified_base
<222> LOCATION: (4)..(4)
<223> OTHER INFORMATION: a, c, g, t, unknown or other

<400> SEQUENCE: 7

| | |
|---|---|
| tttntttttt tcactgcctg tgccaccagt tgtgcactgg gccttgcgat cctctcaagc | 60 |
| tgattcagcc tgcatccttc ccagatggac acgtgtgtga taaacagctc tgcagtgggg | 120 |
| tgagggaagg caggggcagc agggtcctgt atgtcctgcc atctccacaa aagggcagtc | 180 |
| cttaccccag ccttgtgctg atgagaccag gcatagacag tcctgacgac acagggcgga | 240 |
| agggagcagc cattagtgct aatgaggcag gcggcctgaa agcttgtac tctgcagtgg | 300 |
| ctcgcccacc cagggaacag ttcgttctgt ttccttggct tccaggaacc ctaggcagaa | 360 |

| | |
|---|---|
| aggggtttgg ggacaggagc aggagtgggc ggtcttggag aaacctggag ggagaaaggg | 420 |
| agggaggac cagaaatgta gtcaggaggg cctaggattg gttaggtggg cttttccttc | 480 |
| cccctttccct ccaaagaaac ccaggttctg gttctgcacc taccctgcc caacagtggc | 540 |
| cattggccca tcacccgctc caatgtcctt gacccgaatt cttggaagca caggaaacaa | 600 |
| catgccacat aggggttgag taagcatctc tggggccaca aattaaatta gctttcagg | 660 |
| gccgcctgcc ttgttattgc taatggttct agccctgctc agctcctagg tccctgtcct | 720 |
| gtggaaattt gtggaccctg gcaccctct cttgctccca aatttttaatc ggctcctgga | 780 |
| aacctcaccc caaattggag ataggcactc ctcttgtaga acaaaaggct caggttcagg | 840 |
| gagtgagggc ctgaactgtg cccccaccct ccaggaaggg tccttcacgg cctggctgca | 900 |
| gggatcagtc acgtgtggcc cttcattagg ccctgccata taagccaagg gcacggggtg | 960 |
| gccgggaact ctctaggcaa gaatcccgga ggcagaggtg agtcctcagg ttgggcaggg | 1020 |
| actcctcctc tctgtggggt ctctatctgg gcacctagag gggactccaa ggataaggag | 1080 |
| ggactaagtg gtacatcttc ctgctgagcc aaggccatgct gaccgcagcg gtgctgagct | 1140 |
| gtgccctgct gctggcactg cctgccacgc gaggagccca gatgggcttg gcccccatgg | 1200 |
| agggcatcag aaggcctgac caggccctgc tcccagagct cccaggtcag tgtgagcaag | 1260 |
| ggtgggactg ggcggggcct gaataccctc tggccacaaa tagtctcccc tggcataaac | 1320 |
| cctctttctc ccttcccaaa ccctcccctg ggaggtgggt gctttgtgca tgggggttcc | 1380 |
| tgccctcaca tcctctgccc caggcctggg cctgcgggcc ccactgaaga agacaactgc | 1440 |
| agaacaggca gaagaggatc tgttgcagga ggctcaggcc ttggcagagg taactgctca | 1500 |
| gggaaaaggg taaggtggtg gcccttggga ggggcattg ggtattagct cctctcccca | 1560 |
| gctccaaact ccctcaccag cgacgacact accgaccacc ccttcccatg ctccactgcc | 1620 |
| atcctgcaca ggttgggaca ggtaagatcc ctggatctgt ctttagaggc ctgtgctggt | 1680 |
| tccccacccc tgcaggtact agacctgcag gaccgcgagc ccgctcctc acgtcgctgc | 1740 |
| gtaaggctgc atgagtcctg cctgggacag caggtgcctt gctgtgaccc atgtgccacg | 1800 |
| tgctactgcc gcttcttcaa tgccttctgc tactgccgca agctgggtac tgccatgaat | 1860 |
| ccctgcagcc gcacctagct ggccaacgtc agggtcgggg caaggaaact cgaataaagg | 1920 |
| atgggaccaa | 1930 |

<210> SEQ ID NO 8
<211> LENGTH: 594
<212> TYPE: DNA
<213> ORGANISM: Unknown
<220> FEATURE:
<223> OTHER INFORMATION: Description of Unknown: Woodchuck
      post-transcriptional regulatory element polynucleotide

<400> SEQUENCE: 8

| | |
|---|---|
| ataatcaacc tctggattac aaaatttgtg aaagattgac tggtattctt aactatgttg | 60 |
| ctccttttac gctatgtgga tacgctgctt taatgccttt gtatcatgct attgcttccc | 120 |
| gtatggcttt catttctcc tccttgtata aatcctggtt gctgtctctt tatgaggagt | 180 |
| tgtggcccgt tgtcaggcaa cgtggcgtgg tgtgcactgt gtttgctgac gcaaccccca | 240 |
| ctggttgggg cattgccacc acctgtcagc tcctttccgg gactttcgct ttccccctcc | 300 |
| ctattgccac ggcggaactc atcgccgcct gccttgcccg ctgctggaca ggggctcggc | 360 |
| tgttgggcac tgacaattcc gtggtgttgt cggggaaatc atcgtccttt ccttggctgc | 420 |

```
tcgcctgtgt tgccacctgg attctgcgcg ggacgtcctt ctgctacgtc ccttcggccc      480
tcaatccagc ggaccttcct tcccgcggcc tgctgccggc tctgcggcct cttccgcgtc      540
ttcgccttcg ccctcagacg agtcggatct cccttttggg cgcctccccg catc            594
```

```
<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aatactgtca cacacgctca g                                                 21

<210> SEQ ID NO 10
<211> LENGTH: 247
<212> TYPE: PRT
<213> ORGANISM: Homo sapiens

<400> SEQUENCE: 10
```

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Arg Gly Arg
                245

```
<210> SEQ ID NO 11
<211> LENGTH: 838
<212> TYPE: PRT
<213> ORGANISM: Homo sapiens

<400> SEQUENCE: 11

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
    210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
    290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asn Pro Thr
            340                 345                 350

His Met Asn Asn Gly Asp Tyr Thr Leu Ile Ala Lys Asn Glu Tyr Gly
        355                 360                 365

Lys Asp Glu Lys Gln Ile Ser Ala His Phe Met Gly Trp Pro Gly Ile
    370                 375                 380
```

```
Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
            405                 410                 415

Ile Pro Ser Thr Asp Val Thr Asp Lys Thr Gly Arg Glu His Leu Ser
            420                 425                 430

Val Tyr Ala Val Val Val Ile Ala Ser Val Val Gly Phe Cys Leu Leu
            435                 440                 445

Val Met Leu Phe Leu Leu Lys Leu Ala Arg His Ser Lys Phe Gly Met
    450                 455                 460

Lys Asp Phe Ser Trp Phe Gly Phe Gly Lys Val Lys Ser Arg Gln Gly
465                 470                 475                 480

Val Gly Pro Ala Ser Val Ile Ser Asn Asp Asp Ser Ala Ser Pro
                485                 490                 495

Leu His His Ile Ser Asn Gly Ser Asn Thr Pro Ser Ser Glu Gly
                500                 505                 510

Gly Pro Asp Ala Val Ile Ile Gly Met Thr Lys Ile Pro Val Ile Glu
    515                 520                 525

Asn Pro Gln Tyr Phe Gly Ile Thr Asn Ser Gln Leu Lys Pro Asp Thr
530                 535                 540

Phe Val Gln His Ile Lys Arg His Asn Ile Val Leu Lys Arg Glu Leu
545                 550                 555                 560

Gly Glu Gly Ala Phe Gly Lys Val Phe Leu Ala Glu Cys Tyr Asn Leu
                565                 570                 575

Cys Pro Glu Gln Asp Lys Ile Leu Val Ala Val Lys Thr Leu Lys Asp
                580                 585                 590

Ala Ser Asp Asn Ala Arg Lys Asp Phe His Arg Glu Ala Glu Leu Leu
    595                 600                 605

Thr Asn Leu Gln His Glu His Ile Val Lys Phe Tyr Gly Val Cys Val
    610                 615                 620

Glu Gly Asp Pro Leu Ile Met Val Phe Glu Tyr Met Lys His Gly Asp
625                 630                 635                 640

Leu Asn Lys Phe Leu Arg Ala His Gly Pro Asp Ala Val Leu Met Ala
                645                 650                 655

Glu Gly Asn Pro Pro Thr Glu Leu Thr Gln Ser Gln Met Leu His Ile
                660                 665                 670

Ala Gln Gln Ile Ala Ala Gly Met Val Tyr Leu Ala Ser Gln His Phe
                675                 680                 685

Val His Arg Asp Leu Ala Thr Arg Asn Cys Leu Val Gly Glu Asn Leu
    690                 695                 700

Leu Val Lys Ile Gly Asp Phe Gly Met Ser Arg Asp Val Tyr Ser Thr
705                 710                 715                 720

Asp Tyr Tyr Arg Val Gly Gly His Thr Met Leu Pro Ile Arg Trp Met
                725                 730                 735

Pro Pro Glu Ser Ile Met Tyr Arg Lys Phe Thr Thr Glu Ser Asp Val
                740                 745                 750

Trp Ser Leu Gly Val Val Leu Trp Glu Ile Phe Thr Tyr Gly Lys Gln
                755                 760                 765

Pro Trp Tyr Gln Leu Ser Asn Asn Glu Val Ile Glu Cys Ile Thr Gln
                770                 775                 780

Gly Arg Val Leu Gln Arg Pro Arg Thr Cys Pro Gln Glu Val Tyr Glu
785                 790                 795                 800
```

```
<210> SEQ ID NO 12
<211> LENGTH: 132
<212> TYPE: PRT
<213> ORGANISM: Homo sapiens

<400> SEQUENCE: 12

Met Leu Thr Ala Ala Val Leu Ser Cys Ala Leu Leu Ala Leu Pro
1               5                   10                  15

Ala Thr Arg Gly Ala Gln Met Gly Leu Ala Pro Met Glu Gly Ile Arg
            20                  25                  30

Arg Pro Asp Gln Ala Leu Leu Pro Glu Leu Pro Gly Leu Gly Leu Arg
            35                  40                  45

Ala Pro Leu Lys Lys Thr Thr Ala Glu Gln Ala Glu Glu Asp Leu Leu
        50                  55                  60

Gln Glu Ala Gln Ala Leu Ala Glu Val Leu Asp Leu Gln Asp Arg Glu
65                  70                  75                  80

Pro Arg Ser Ser Arg Arg Cys Val Arg Leu His Glu Ser Cys Leu Gly
                85                  90                  95

Gln Gln Val Pro Cys Cys Asp Pro Cys Ala Thr Cys Tyr Cys Arg Phe
            100                 105                 110

Phe Asn Ala Phe Cys Tyr Cys Arg Lys Leu Gly Thr Ala Met Asn Pro
            115                 120                 125

Cys Ser Arg Thr
            130
```